(12) United States Patent
Schwarz

(10) Patent No.: US 12,274,494 B2
(45) Date of Patent: *Apr. 15, 2025

(54) TREATMENT DEVICE

(71) Applicant: BTL HEALTHCARE TECHNOLOGIES A.S., Prague (CZ)

(72) Inventor: Tomás Schwarz, Prague (CZ)

(73) Assignee: BTL Healthcare Technologies A.S., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/435,322

(22) Filed: Feb. 7, 2024

(65) Prior Publication Data

US 2024/0252239 A1 Aug. 1, 2024

Related U.S. Application Data

(63) Continuation of application No. 17/498,610, filed on Oct. 11, 2021, now Pat. No. 11,896,299, which is a
(Continued)

(51) Int. Cl.
*A61B 18/18* (2006.01)
*A61B 18/00* (2006.01)
(Continued)

(52) U.S. Cl.
CPC .............. *A61B 18/18* (2013.01); *A61F 13/64* (2013.01); *A61F 13/66* (2013.01);
(Continued)

(58) Field of Classification Search
CPC .......... A61B 18/18; A61B 2018/00005; A61B 2018/00172; A61B 2018/00273;
(Continued)

(56) References Cited

U.S. PATENT DOCUMENTS

| 1,050,280 A | 1/1913 | Ferdinand |
| 1,068,831 A | 7/1913 | Vandoran |

(Continued)

FOREIGN PATENT DOCUMENTS

| AU | 747678 B2 | 5/2002 |
| AU | 2011265424 B2 | 7/2014 |

(Continued)

OTHER PUBLICATIONS

Busso, M. and Denkova, R., "Efficacy of High Intensity Focused Electro-Magnetic (HIFEM) Field Therapy When Used for Non-Invasive Buttocks Augmentation and Lifting: A Clinical Study" American Society for Laser Medicine and Surgery Abstracts, 382 (2018).

(Continued)

*Primary Examiner* — Mark W. Bockelman
(74) *Attorney, Agent, or Firm* — Riverside Law LLP

(57) ABSTRACT

A method of treating tissue of a patient uses a device including a mother case, a belt, at least one treatment unit and at least two applicators. The treatment method may include attaching first and second applicators to the belt at a working distance to the patient's surface, and providing different treatment energy to the first applicator and the second applicator. A treatment pattern is created by the applicators providing the different treatment energies. The hardware pattern or positions of the applicators on the belt may be changed before and/or during the treatment. The hardware pattern may be based on selected treatment effect and body part.

20 Claims, 14 Drawing Sheets

Related U.S. Application Data continuation of application No. 15/678,915, filed on Aug. 16, 2017, now Pat. No. 11,141,219.

(60) Provisional application No. 62/375,796, filed on Aug. 16, 2016.

(51) Int. Cl.
*A61F 13/64* (2006.01)
*A61F 13/66* (2006.01)

(52) U.S. Cl.
CPC ............... *A61B 2018/00005* (2013.01); *A61B 2018/00172* (2013.01); *A61B 2018/00273* (2013.01); *A61B 2018/00464* (2013.01); *A61B 2018/00654* (2013.01); *A61B 2018/00916* (2013.01); *A61B 2018/00958* (2013.01); *A61B 2018/00988* (2013.01); *A61B 2018/00994* (2013.01)

(58) Field of Classification Search
CPC ........... A61B 2018/00464; A61B 2018/00654; A61B 2018/00916; A61B 2018/00958; A61B 2018/00988; A61B 2018/00994; A61B 18/14; A61B 2018/0047; A61F 13/64; A61F 13/66; A61F 7/02; A61F 2007/0022; A61F 2007/0027; A61F 2007/0031; A61F 2007/0034; A61F 2007/004; A61F 2007/0041; A61F 2007/0228; A61F 2007/029; A61N 2005/0626; A61N 2005/0645; A61N 1/0452; A61N 1/0484; A61N 1/328; A61N 1/40; A61N 2/002; A61N 5/0616; A61N 7/00; A61N 7/02; A61N 2007/0008; A61N 2007/0034

See application file for complete search history.

(56) References Cited

U.S. PATENT DOCUMENTS

| | | |
|---|---|---|
| 1,973,387 A | 9/1934 | Neymann |
| 2,021,676 A | 11/1935 | Wood |
| 3,163,161 A | 12/1964 | Courtin |
| 3,566,877 A | 3/1971 | Smith |
| 3,658,051 A | 4/1972 | MacLean |
| 3,709,228 A | 1/1973 | Barker |
| 3,841,306 A | 10/1974 | Hallgren |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry |
| 4,143,661 A | 3/1979 | Laforge |
| 4,197,851 A | 4/1980 | Fellus |
| 4,237,898 A | 12/1980 | Whalley |
| 4,261,364 A | 4/1981 | Haddad |
| 4,305,115 A | 12/1981 | Armitage |
| 4,315,503 A | 2/1982 | Ryaby |
| 4,392,040 A | 7/1983 | Rand |
| 4,454,883 A | 6/1984 | Fellus |
| 4,456,001 A | 6/1984 | Pescatore |
| 4,550,714 A | 11/1985 | Talish |
| 4,556,056 A | 12/1985 | Fischer |
| 4,665,898 A | 5/1987 | Costa |
| 4,674,482 A | 6/1987 | Waltonen |
| 4,674,505 A | 6/1987 | Pauli |
| 4,723,536 A | 2/1988 | Rauscher |
| 4,850,959 A | 7/1989 | Findl |
| 4,889,526 A | 12/1989 | Rauscher |
| 4,957,480 A | 9/1990 | Mornings |
| 4,989,604 A | 2/1991 | Fang |
| 4,993,413 A | 2/1991 | McLeod |
| 5,061,234 A | 10/1991 | Chaney |
| 5,067,940 A | 11/1991 | Liboff |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson |
| 5,199,951 A | 4/1993 | Spears |
| 5,246,438 A | 9/1993 | Langberg |
| 5,334,181 A | 8/1994 | Rubinsky |
| 5,339,217 A | 8/1994 | Cohen |
| 5,344,384 A | 9/1994 | Ostrow |
| 5,401,233 A | 3/1995 | Erickson |
| 5,415,617 A | 5/1995 | Kraus |
| 5,419,344 A | 5/1995 | Dewitt |
| 5,433,737 A | 7/1995 | Aimone |
| 5,433,740 A | 7/1995 | Yamaguchi |
| 5,562,706 A | 10/1996 | Lauterbach |
| 5,584,863 A | 12/1996 | Rauch |
| 5,620,463 A | 4/1997 | Drolet |
| 5,660,836 A | 8/1997 | Knowlton |
| 5,674,218 A | 10/1997 | Rubinsky |
| 5,690,692 A | 11/1997 | Fleming |
| 5,691,873 A | 11/1997 | Masaki |
| 5,718,662 A | 2/1998 | Jalinous |
| 5,720,773 A | 2/1998 | Lopez-Claros |
| 5,725,471 A | 3/1998 | Davey |
| 5,755,753 A | 5/1998 | Knowlton |
| 5,766,124 A | 6/1998 | Polson |
| 5,769,778 A | 6/1998 | Abrams |
| 5,782,743 A | 7/1998 | Russell |
| 5,807,232 A | 9/1998 | Espinoza |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa |
| 6,017,337 A | 1/2000 | Pira |
| 6,032,675 A | 3/2000 | Rubinsky |
| 6,038,485 A | 3/2000 | Axelgaard |
| 6,042,531 A | 3/2000 | Holcomb |
| 6,047,215 A | 4/2000 | McClure |
| 6,050,994 A | 4/2000 | Sherman |
| 6,063,108 A | 5/2000 | Salansky |
| 6,067,474 A | 5/2000 | Schulman |
| 6,086,525 A | 7/2000 | Davey |
| 6,094,599 A | 7/2000 | Bingham |
| 6,099,459 A | 8/2000 | Jacobson |
| 6,099,523 A | 8/2000 | Kim |
| 6,117,066 A | 9/2000 | Abrams |
| 6,132,361 A | 10/2000 | Epstein |
| 6,141,985 A | 11/2000 | Cluzeau |
| 6,155,966 A | 12/2000 | Parker |
| 6,161,757 A | 12/2000 | Morris |
| 6,179,769 B1 | 1/2001 | Ishikawa |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa |
| 6,246,905 B1 | 6/2001 | Mogul |
| 6,255,815 B1 | 7/2001 | Davey |
| 6,261,301 B1 | 7/2001 | Knesch |
| 6,273,862 B1 | 8/2001 | Privitera |
| 6,273,884 B1 | 8/2001 | Altshuler |
| 6,280,376 B1 | 8/2001 | Holcomb |
| 6,282,448 B1 | 8/2001 | Katz |
| D447,806 S | 9/2001 | Davey |
| 6,311,090 B1 | 10/2001 | Knowlton |
| 6,324,430 B1 | 11/2001 | Zarinetchi |
| 6,324,432 B1 | 11/2001 | Rigaux |
| 6,334,069 B1 | 12/2001 | George |
| 6,334,074 B1 | 12/2001 | Spertell |
| 6,350,276 B1 | 2/2002 | Knowlton |
| 6,366,814 B1 | 4/2002 | Boveja |
| 6,402,678 B1 | 6/2002 | Fischell |
| 6,413,255 B1 | 7/2002 | Stern |
| 6,418,345 B1 | 7/2002 | Tepper |
| 6,424,864 B1 | 7/2002 | Matsuura |
| 6,425,852 B1 | 7/2002 | Epstein |

(56) References Cited

U.S. PATENT DOCUMENTS

| | | |
|---|---|---|
| 6,443,883 B1 | 9/2002 | Ostrow |
| 6,445,955 B1 | 9/2002 | Michelson |
| 6,447,440 B1 | 9/2002 | Markoll |
| 6,453,202 B1 | 9/2002 | Knowlton |
| 6,461,375 B1 | 10/2002 | Baudry |
| 6,491,620 B1 | 12/2002 | Davey |
| 6,500,110 B1 | 12/2002 | Davey |
| 6,520,903 B1 | 2/2003 | Yamashiro |
| 6,527,694 B1 | 3/2003 | Ishikawa |
| 6,527,695 B1 | 3/2003 | Davey |
| 6,537,197 B1 | 3/2003 | Ruohonen |
| 6,569,078 B2 | 5/2003 | Ishikawa |
| 6,591,138 B1 | 7/2003 | Fischell |
| 6,605,080 B1 | 8/2003 | Altshuler |
| 6,635,053 B1 | 10/2003 | Lalonde |
| 6,658,301 B2 | 12/2003 | Loeb |
| 6,662,054 B2 | 12/2003 | Kreindel |
| 6,663,556 B2 | 12/2003 | Barker |
| 6,663,659 B2 | 12/2003 | McDaniel |
| 6,701,185 B2 | 3/2004 | Burnett |
| 6,702,808 B1 | 3/2004 | Kreindel |
| 6,713,733 B2 | 3/2004 | Kochman |
| 6,735,481 B1 | 5/2004 | Bingham |
| 6,738,667 B2 | 5/2004 | Deno |
| 6,749,624 B2 | 6/2004 | Knowlton |
| 6,827,681 B2 | 12/2004 | Tanner |
| 6,849,040 B2 | 2/2005 | Ruohonen |
| 6,860,852 B2 | 3/2005 | Schoenenberger |
| 6,871,099 B1 | 3/2005 | Whitehurst |
| 6,879,859 B1 | 4/2005 | Boveja |
| 6,889,090 B2 | 5/2005 | Kreindel |
| 6,920,883 B2 | 7/2005 | Bessette |
| 6,926,660 B2 | 8/2005 | Miller |
| 6,939,287 B1 | 9/2005 | Ardizzone |
| 6,939,344 B2 | 9/2005 | Kreindel |
| 6,960,202 B2 | 11/2005 | Cluzeau |
| 6,990,427 B2 | 1/2006 | Kirsch |
| 7,008,370 B2 | 3/2006 | Tanner |
| 7,024,239 B2 | 4/2006 | George |
| 7,030,764 B2 | 4/2006 | Smith |
| 7,041,100 B2 | 5/2006 | Kreindel |
| 7,083,580 B2 | 8/2006 | Bernabei |
| 7,104,947 B2 | 9/2006 | Riehl |
| 7,153,256 B2 | 12/2006 | Riehl |
| 7,186,209 B2 | 3/2007 | Jacobson |
| 7,211,082 B2 | 5/2007 | Hall |
| 7,217,265 B2 | 5/2007 | Hennings |
| 7,238,183 B2 | 7/2007 | Kreindel |
| 7,276,020 B2 | 10/2007 | Becker |
| 7,276,058 B2 | 10/2007 | Altshuler |
| 7,294,101 B2 | 11/2007 | Fischell |
| 7,309,309 B2 | 12/2007 | Wang |
| 7,318,821 B2 | 1/2008 | Lalonde |
| 7,320,664 B2 | 1/2008 | Riehl |
| 7,351,252 B2 | 4/2008 | Altshuler |
| 7,367,341 B2 | 5/2008 | Anderson |
| 7,367,936 B2 | 5/2008 | Myers |
| 7,369,895 B2 | 5/2008 | Hurtado |
| 7,372,271 B2 | 5/2008 | Roozen |
| 7,376,460 B2 | 5/2008 | Bernabei |
| 7,396,326 B2 | 7/2008 | Kenneth |
| 7,407,478 B2 | 8/2008 | Zangen |
| 7,494,458 B2 | 2/2009 | Fischell |
| 7,496,401 B2 | 2/2009 | Bernabei |
| 7,520,848 B2 | 4/2009 | Schneider |
| 7,520,849 B1 | 4/2009 | Simon |
| 7,520,875 B2 | 4/2009 | Bernabei |
| 7,532,926 B2 | 5/2009 | Bernabei |
| 7,560,058 B2 | 7/2009 | Riehl |
| 7,571,003 B2 | 8/2009 | Pozzato |
| 7,591,776 B2 | 9/2009 | Phillips |
| 7,601,115 B2 | 10/2009 | Riehl |
| 7,601,116 B2 | 10/2009 | Fischell |
| 7,608,035 B2 | 10/2009 | Farone |
| 7,614,996 B2 | 11/2009 | Riehl |
| 7,618,429 B2 | 11/2009 | Mulholland |
| 7,630,774 B2 | 12/2009 | Karni |
| 7,643,883 B2 | 1/2010 | Kreindel |
| 7,651,459 B2 | 1/2010 | Cameron |
| 7,697,998 B2 | 4/2010 | Axelgaard |
| 7,697,999 B2 | 4/2010 | Axelgaard |
| 7,699,768 B2 | 4/2010 | Kishawi |
| 7,706,885 B2 | 4/2010 | Farone |
| 7,711,431 B2 | 5/2010 | Tanner |
| 7,740,574 B2 | 6/2010 | Pilla |
| 7,744,523 B2 | 6/2010 | Epstein |
| 7,753,836 B2 | 7/2010 | Peterchev |
| 7,783,348 B2 | 8/2010 | Gill |
| 7,785,358 B2 | 8/2010 | Lach |
| 7,824,324 B2 | 11/2010 | Riehl |
| 7,854,232 B2 | 12/2010 | Aho |
| 7,854,754 B2 | 12/2010 | Ting |
| 7,857,746 B2 | 12/2010 | Riehl |
| 7,857,775 B2 | 12/2010 | Rosenberg |
| 7,901,373 B2 | 3/2011 | Tavger |
| 7,909,786 B2 | 3/2011 | Bonnefin |
| 7,914,469 B2 | 3/2011 | Torbati |
| 7,925,066 B2 | 4/2011 | Ruohonen |
| 7,945,321 B2 | 5/2011 | Bernabei |
| 7,946,973 B2 | 5/2011 | Peterchev |
| 7,953,500 B2 | 5/2011 | Bingham |
| 7,963,903 B2 | 6/2011 | Ghiron |
| 7,976,451 B2 | 7/2011 | Zangen |
| 7,981,146 B2 | 7/2011 | Korb |
| 7,998,053 B2 | 8/2011 | Aho |
| 8,029,432 B2 | 10/2011 | Dennis |
| 8,035,385 B2 | 10/2011 | Tomiha |
| 8,052,591 B2 | 11/2011 | Mishelevich |
| RE43,007 E | 12/2011 | Lalonde |
| 8,088,058 B2 | 1/2012 | Juliana |
| 8,105,254 B2 | 1/2012 | Guantera |
| 8,118,722 B2 | 2/2012 | Riehl |
| 8,128,549 B2 | 3/2012 | Testani |
| 8,133,191 B2 | 3/2012 | Rosenberg |
| 8,137,258 B1 | 3/2012 | Dennis |
| 8,137,259 B1 | 3/2012 | Dennis |
| 8,170,643 B2 | 5/2012 | Turner |
| 8,172,835 B2 | 5/2012 | Leyh |
| 8,177,702 B2 | 5/2012 | Riehl |
| 8,192,474 B2 | 6/2012 | Levinson |
| 8,204,446 B2 | 6/2012 | Scheer |
| 8,246,529 B2 | 8/2012 | Riehl |
| 8,251,986 B2 | 8/2012 | Chornenky |
| 8,262,556 B2 | 9/2012 | Fischell |
| 8,265,763 B2 | 9/2012 | Fahey |
| 8,265,910 B2 | 9/2012 | Mishelevich |
| 8,267,850 B2 | 9/2012 | Schneider |
| 8,271,090 B1 | 9/2012 | Hartman |
| 8,275,442 B2 | 9/2012 | Allison |
| 8,277,371 B2 | 10/2012 | Zangen |
| 8,285,390 B2 | 10/2012 | Levinson |
| 8,303,478 B2 | 11/2012 | Lebosse |
| 8,335,566 B2 | 12/2012 | Mueller |
| 8,337,539 B2 | 12/2012 | Ting |
| 8,366,756 B2 | 2/2013 | Tucek |
| 8,376,825 B2 | 2/2013 | Guinn |
| 8,376,925 B1 | 2/2013 | Dennis |
| 8,388,510 B2 | 3/2013 | Zangen |
| 8,428,735 B2 | 4/2013 | Littlewood |
| 8,454,591 B2 | 6/2013 | Leyh |
| 8,457,751 B2 | 6/2013 | Pozzato |
| 8,465,408 B2 | 6/2013 | Phillips |
| 8,475,354 B2 | 7/2013 | Phillips |
| 8,480,554 B2 | 7/2013 | Phillips |
| 8,493,286 B1 | 7/2013 | Agrama |
| 8,506,468 B2 | 8/2013 | Ghiron |
| 8,517,908 B2 | 8/2013 | Riehl |
| 8,523,753 B2 | 9/2013 | Schneider |
| 8,523,927 B2 | 9/2013 | Levinson |
| 8,548,599 B2 | 10/2013 | Zarsky |
| 8,565,888 B2 | 10/2013 | Buhlmann |
| 8,579,953 B1 | 11/2013 | Dunbar |
| 8,585,568 B2 | 11/2013 | Phillips |
| 8,585,617 B2 | 11/2013 | Mashiach |

(56) References Cited

U.S. PATENT DOCUMENTS

| | | |
|---|---|---|
| 8,588,930 B2 | 11/2013 | Diubaldi |
| 8,593,245 B2 | 11/2013 | Zeng |
| 8,603,073 B2 | 12/2013 | Allison |
| 8,608,634 B2 | 12/2013 | Zangen |
| 8,641,710 B2 | 2/2014 | Doty |
| 8,646,239 B2 | 2/2014 | Rulon |
| 8,657,731 B2 | 2/2014 | Riehl |
| 8,666,492 B2 | 3/2014 | Muller |
| 8,676,338 B2 | 3/2014 | Levinson |
| 8,684,901 B1 | 4/2014 | Zabara |
| 8,700,176 B2 | 4/2014 | Azar |
| 8,702,774 B2 | 4/2014 | Baker |
| 8,721,572 B1 | 5/2014 | Linder |
| 8,723,628 B2 | 5/2014 | Mishelevich |
| 8,725,270 B2 | 5/2014 | Towe |
| 8,740,765 B1 | 6/2014 | Fischell |
| 8,768,454 B2 | 7/2014 | Sham |
| 8,771,163 B2 | 7/2014 | Zangen |
| 8,771,326 B2 | 7/2014 | Myeong |
| 8,777,831 B2 | 7/2014 | Aho |
| 8,788,044 B2 | 7/2014 | John |
| 8,788,060 B2 | 7/2014 | Nebrigic |
| 8,795,148 B2 | 8/2014 | Schneider |
| 8,801,589 B2 | 8/2014 | Peterchev |
| 8,825,166 B2 | 9/2014 | John |
| 8,834,547 B2 | 9/2014 | Anderson |
| 8,840,608 B2 | 9/2014 | Anderson |
| 8,845,508 B2 | 9/2014 | Schneider |
| 8,864,641 B2 | 10/2014 | Riehl |
| 8,868,177 B2 | 10/2014 | Simon |
| 8,870,737 B2 | 10/2014 | Phillips |
| 8,888,672 B2 | 11/2014 | Phillips |
| 8,888,673 B2 | 11/2014 | Phillips |
| 8,906,009 B2 | 12/2014 | Nebrigic |
| 8,909,342 B2 | 12/2014 | Lozano |
| 8,915,948 B2 | 12/2014 | Altshuler |
| 8,926,490 B2 | 1/2015 | Phillips |
| 8,932,338 B2 | 1/2015 | Lim |
| 8,956,273 B2 | 2/2015 | Mishelevich |
| 8,956,274 B2 | 2/2015 | Schneider |
| 8,961,386 B2 | 2/2015 | Phillips |
| 8,979,727 B2 | 3/2015 | Ron Edoute |
| 8,985,331 B2 | 3/2015 | Guenter |
| 8,998,791 B2 | 4/2015 | Ron Edoute |
| 9,002,477 B2 | 4/2015 | Burnett |
| 9,008,793 B1 | 4/2015 | Cosman, Sr. |
| 9,015,057 B2 | 4/2015 | Phillips |
| 9,028,469 B2 | 5/2015 | Jones |
| 9,031,659 B2 | 5/2015 | Campbell |
| 9,033,861 B2 | 5/2015 | Fischell |
| 9,037,247 B2 | 5/2015 | Simon |
| 9,044,595 B2 | 6/2015 | Araya |
| 9,061,128 B2 | 6/2015 | Hall |
| 9,067,052 B2 | 6/2015 | Moses |
| 9,072,891 B1 | 7/2015 | Rao |
| 9,078,634 B2 | 7/2015 | Gonzales |
| 9,089,719 B2 | 7/2015 | Simon |
| 9,101,524 B2 | 8/2015 | Aghion |
| 9,132,031 B2 | 9/2015 | Levinson |
| 9,144,513 B2 | 9/2015 | Paulson |
| 9,149,650 B2 | 10/2015 | Shanks |
| 9,168,096 B2 | 10/2015 | Kreindel |
| 9,233,207 B2 | 1/2016 | Polyakov |
| 9,233,257 B1 | 1/2016 | Zabara |
| 9,254,395 B1 | 2/2016 | Shambayati |
| 9,261,574 B2 | 2/2016 | Boskamp |
| 9,265,690 B2 | 2/2016 | Kriksunov |
| 9,308,120 B2 | 4/2016 | Anderson |
| 9,314,368 B2 | 4/2016 | Allison |
| 9,326,910 B2 | 5/2016 | Eckhouse |
| 9,339,641 B2 | 5/2016 | Rajguru |
| 9,358,068 B2 | 6/2016 | Schomacker |
| 9,358,149 B2 | 6/2016 | Anderson |
| 9,375,345 B2 | 6/2016 | Levinson |
| 9,387,339 B2 | 7/2016 | Sham |
| 9,398,975 B2 | 7/2016 | Müller et al. |
| 9,408,745 B2 | 8/2016 | Levinson |
| 9,414,759 B2 | 8/2016 | Lang |
| 9,415,217 B2 * | 8/2016 | Chen ............ A61N 1/0452 |
| 9,433,797 B2 | 9/2016 | Pilla |
| 9,439,805 B2 | 9/2016 | Gonzales |
| 9,446,258 B1 | 9/2016 | Schwarz |
| 9,468,774 B2 | 10/2016 | Zárský |
| 9,526,912 B1 | 12/2016 | Fischell |
| 9,532,832 B2 | 1/2017 | Ron Edoute |
| 9,545,523 B2 | 1/2017 | Nanda |
| 9,550,067 B1 | 1/2017 | Fischell |
| 9,561,357 B2 | 2/2017 | Hall |
| 9,561,384 B1 | 2/2017 | Fischell |
| 9,586,048 B2 | 3/2017 | Ternes |
| 9,586,057 B2 | 3/2017 | Ladman |
| 9,596,920 B2 | 3/2017 | Shalev |
| 9,597,225 B1 | 3/2017 | Guerrieri |
| 9,610,429 B2 | 4/2017 | Harris |
| 9,610,459 B2 | 4/2017 | Burnett |
| 9,615,854 B2 | 4/2017 | Matsushita |
| 9,636,516 B2 | 5/2017 | Schwarz |
| 9,636,519 B2 | 5/2017 | Ladman |
| 9,649,220 B2 | 5/2017 | Anderson |
| 9,655,770 B2 | 5/2017 | Levinson |
| 9,675,800 B2 | 6/2017 | Li |
| 9,675,815 B1 | 6/2017 | Fischell |
| 9,694,194 B2 | 7/2017 | Ron Edoute |
| 9,707,121 B2 | 7/2017 | Hyde |
| 9,713,567 B2 | 7/2017 | Guantera |
| 9,724,533 B1 | 8/2017 | Fischell |
| 9,737,238 B2 | 8/2017 | Wright |
| 9,737,434 B2 | 8/2017 | Allison |
| 9,757,584 B2 | 9/2017 | Burnett |
| 9,782,324 B2 | 10/2017 | Crunick |
| 9,814,897 B2 | 11/2017 | Ron Edoute |
| 9,844,460 B2 | 12/2017 | Weber |
| 9,844,461 B2 | 12/2017 | Levinson |
| 9,849,299 B2 | 12/2017 | Sham |
| 9,849,302 B1 | 12/2017 | Fischell |
| 9,855,166 B2 | 1/2018 | Anderson |
| 9,861,421 B2 | 1/2018 | O'Neil |
| 9,861,520 B2 | 1/2018 | Baker |
| 9,867,996 B2 | 1/2018 | Zarsky |
| 9,901,743 B2 | 2/2018 | Ron Edoute |
| 9,919,161 B2 | 3/2018 | Schwarz |
| 9,937,358 B2 | 4/2018 | Schwarz |
| 9,962,553 B2 | 5/2018 | Schwarz |
| 9,968,797 B2 | 5/2018 | Sham |
| 9,974,519 B1 | 5/2018 | Schwarz |
| 9,974,684 B2 | 5/2018 | Anderson |
| 9,980,765 B2 | 5/2018 | Avram |
| 9,981,143 B2 | 5/2018 | Ron Edoute |
| 9,999,780 B2 | 6/2018 | Weyh |
| 10,029,112 B1 | 7/2018 | Fischell |
| 10,037,867 B2 | 7/2018 | Godyak |
| 10,039,929 B1 | 8/2018 | Schwarz |
| 10,080,906 B2 | 9/2018 | Schwarz |
| 10,092,346 B2 | 10/2018 | Levinson |
| 10,111,770 B2 | 10/2018 | Harris |
| 10,111,774 B2 | 10/2018 | Gonzales |
| 10,124,187 B2 | 11/2018 | Schwarz |
| 10,183,172 B2 | 1/2019 | Ghiron |
| 10,195,010 B2 | 2/2019 | Sanders |
| 10,195,427 B2 | 2/2019 | Kent |
| 10,195,453 B2 | 2/2019 | Schwarz |
| 10,195,454 B2 | 2/2019 | Yamashiro |
| 10,195,456 B2 | 2/2019 | Cabrerizo |
| 10,201,380 B2 | 2/2019 | Debenedictis |
| 10,245,439 B1 | 4/2019 | Schwarz |
| 10,271,900 B2 | 4/2019 | Marchitto |
| 10,279,185 B2 | 5/2019 | Meadows |
| 10,342,988 B2 | 7/2019 | Midorikawa |
| 10,363,419 B2 | 7/2019 | Simon |
| 10,413,745 B2 | 9/2019 | Riehl |
| 10,463,869 B2 | 11/2019 | Ron Edoute |
| 10,471,269 B1 | 11/2019 | Schwarz |
| 10,471,271 B1 | 11/2019 | John |
| 10,478,588 B2 | 11/2019 | Walpole |

(56) References Cited

U.S. PATENT DOCUMENTS

| | | | |
|---|---|---|---|
| 10,478,633 B2 | 11/2019 | Schwarz | |
| 10,478,634 B2 | 11/2019 | Schwarz | |
| 10,493,293 B2 | 12/2019 | Schwarz | |
| 10,518,098 B2 | 12/2019 | Hong | |
| 10,549,109 B2 | 2/2020 | Schwarz | |
| 10,549,110 B1 | 2/2020 | Schwarz | |
| 10,556,121 B2 | 2/2020 | Gurfein | |
| 10,556,122 B1 | 2/2020 | Schwarz | |
| 10,569,094 B2 | 2/2020 | Schwarz | |
| 10,569,095 B1 | 2/2020 | Schwarz | |
| 10,583,287 B2 | 3/2020 | Schwarz | |
| 10,589,117 B1 | 3/2020 | Fischell | |
| 10,596,366 B2 | 3/2020 | Sama | |
| 10,596,386 B2 | 3/2020 | Schwarz | |
| 10,610,696 B1 | 4/2020 | Peled | |
| 10,632,321 B2 | 4/2020 | Schwarz | |
| 10,639,490 B2 | 5/2020 | Simon | |
| 10,661,093 B2 | 5/2020 | Ron Edoute | |
| 10,668,282 B2 * | 6/2020 | Chen | A61N 1/36034 |
| 10,675,819 B2 | 6/2020 | Li | |
| 10,688,310 B2 | 6/2020 | Schwarz | |
| 10,695,575 B1 | 6/2020 | Schwarz | |
| 10,695,576 B2 | 6/2020 | Schwarz | |
| 10,709,894 B2 | 7/2020 | Schwarz | |
| 10,709,895 B2 | 7/2020 | Schwarz | |
| 10,773,094 B1 | 9/2020 | Rzasa | |
| 10,806,943 B2 | 10/2020 | Sokolowski | |
| 10,821,295 B1 | 11/2020 | Schwarz | |
| 10,835,418 B1 | 11/2020 | Darbandi | |
| 10,849,784 B2 | 12/2020 | Jurna | |
| 10,898,710 B1 | 1/2021 | Sanderford | |
| 10,946,195 B2 | 3/2021 | Strohl | |
| 11,141,219 B1 | 10/2021 | Schwarz | |
| 11,185,690 B2 | 11/2021 | Schwarz | |
| 11,207,540 B2 | 12/2021 | Zangen | |
| 11,247,039 B2 | 2/2022 | Schwarz | |
| 11,247,063 B2 | 2/2022 | Schwarz | |
| 11,266,850 B2 | 3/2022 | Prouza | |
| 11,266,852 B2 | 3/2022 | Schwarz | |
| 11,278,732 B2 | 3/2022 | Casalino | |
| 11,351,361 B2 * | 6/2022 | Chen | A61N 1/36034 |
| 11,420,061 B2 | 8/2022 | Caparso | |
| 11,464,994 B2 | 10/2022 | Schwarz | |
| 11,478,638 B2 | 10/2022 | Toong | |
| 11,484,263 B2 | 11/2022 | Leaper | |
| 11,484,725 B2 | 11/2022 | Schwarz | |
| 11,484,727 B2 | 11/2022 | Schwarz | |
| 11,529,514 B2 | 12/2022 | Bolea | |
| 11,534,619 B2 | 12/2022 | Schwarz | |
| 11,607,556 B2 | 3/2023 | Schwarz | |
| 11,672,999 B1 | 6/2023 | John | |
| 11,691,024 B2 | 7/2023 | Schwarz | |
| 11,724,101 B2 * | 8/2023 | Chen | A61N 1/0484 607/59 |
| 11,779,767 B1 | 10/2023 | John | |
| 11,794,029 B2 | 10/2023 | Schwarz | |
| 11,806,528 B2 | 11/2023 | Schwarz | |
| 12,121,722 B2 * | 10/2024 | Chen | A61N 1/0484 |
| 2001/0018547 A1 | 8/2001 | Mechlenburg | |
| 2001/0031906 A1 | 10/2001 | Ishikawa | |
| 2002/0010414 A1 | 1/2002 | Coston | |
| 2002/0049483 A1 | 4/2002 | Knowlton | |
| 2002/0082466 A1 | 6/2002 | Han | |
| 2002/0103411 A1 | 8/2002 | Bailey | |
| 2002/0128686 A1 | 9/2002 | Minogue | |
| 2002/0143365 A1 | 10/2002 | Herbst | |
| 2002/0143373 A1 | 10/2002 | Courtnage | |
| 2002/0160436 A1 | 10/2002 | Markov | |
| 2002/0165590 A1 | 11/2002 | Crowe | |
| 2002/0193709 A1 | 12/2002 | Bolze | |
| 2003/0028072 A1 | 2/2003 | Fischell | |
| 2003/0032900 A1 | 2/2003 | Ella | |
| 2003/0032950 A1 | 2/2003 | Altshuler | |
| 2003/0050527 A1 | 3/2003 | Fox | |
| 2003/0056281 A1 | 3/2003 | Hasegawa | |
| 2003/0074037 A1 | 4/2003 | Moore | |
| 2003/0078646 A1 | 4/2003 | Axelgaard | |
| 2003/0093133 A1 | 5/2003 | Crowe | |
| 2003/0130711 A1 | 7/2003 | Pearson | |
| 2003/0134545 A1 | 7/2003 | McAdams | |
| 2003/0139789 A1 | 7/2003 | Tvinnereim | |
| 2003/0149451 A1 | 8/2003 | Chomenky | |
| 2003/0153958 A1 | 8/2003 | Yamazaki | |
| 2003/0158585 A1 | 8/2003 | Burnett | |
| 2003/0216729 A1 | 11/2003 | Marchitto | |
| 2003/0220635 A1 | 11/2003 | Knowlton | |
| 2003/0220674 A1 | 11/2003 | Anderson | |
| 2003/0236487 A1 | 12/2003 | Knowlton | |
| 2004/0015163 A1 | 1/2004 | Buysse | |
| 2004/0034346 A1 | 2/2004 | Stern | |
| 2004/0039279 A1 | 2/2004 | Ruohonen | |
| 2004/0073079 A1 | 4/2004 | Altshuler | |
| 2004/0077977 A1 | 4/2004 | Ella | |
| 2004/0093042 A1 | 5/2004 | Altshuler | |
| 2004/0102768 A1 | 5/2004 | Cluzeau | |
| 2004/0162583 A1 | 8/2004 | Bingham | |
| 2004/0193000 A1 | 9/2004 | Riehl | |
| 2004/0193003 A1 | 9/2004 | Mechlenburg | |
| 2004/0206365 A1 | 10/2004 | Knowlton | |
| 2004/0210214 A1 | 10/2004 | Knowlton | |
| 2004/0210282 A1 | 10/2004 | Flock | |
| 2004/0210287 A1 | 10/2004 | Greene | |
| 2004/0230226 A1 | 11/2004 | Bingham | |
| 2004/0260210 A1 | 12/2004 | Ella | |
| 2005/0004632 A1 | 1/2005 | Benedict | |
| 2005/0038313 A1 | 2/2005 | Ardizzone | |
| 2005/0049543 A1 | 3/2005 | Anderson | |
| 2005/0075701 A1 | 4/2005 | Shafer | |
| 2005/0075702 A1 | 4/2005 | Shafer | |
| 2005/0085866 A1 | 4/2005 | Tehrani | |
| 2005/0085874 A1 | 4/2005 | Davis | |
| 2005/0090814 A1 | 4/2005 | Lalonde | |
| 2005/0107656 A1 | 5/2005 | Jang | |
| 2005/0134193 A1 | 6/2005 | Myers | |
| 2005/0148808 A1 | 7/2005 | Cameron | |
| 2005/0177203 A1 | 8/2005 | Brighton | |
| 2005/0187599 A1 | 8/2005 | Sharkey | |
| 2005/0203504 A1 | 9/2005 | Wham | |
| 2005/0215987 A1 | 9/2005 | Slatkine | |
| 2005/0216062 A1 | 9/2005 | Herbst | |
| 2005/0228210 A1 | 10/2005 | Muntermann | |
| 2005/0251120 A1 | 11/2005 | Anderson | |
| 2005/0251229 A1 | 11/2005 | Pilla | |
| 2006/0004244 A1 | 1/2006 | Phillips | |
| 2006/0020236 A1 | 1/2006 | Ben-Nun | |
| 2006/0036300 A1 | 2/2006 | Kreindel | |
| 2006/0064082 A1 | 3/2006 | Bonutti | |
| 2006/0069420 A1 | 3/2006 | Rademacher | |
| 2006/0094924 A1 | 5/2006 | Riehl | |
| 2006/0100550 A1 | 5/2006 | Schultheiss | |
| 2006/0100552 A1 | 5/2006 | Schultheiss | |
| 2006/0106375 A1 | 5/2006 | Werneth | |
| 2006/0152301 A1 | 7/2006 | Rohwedder | |
| 2006/0183252 A1 | 8/2006 | Lee | |
| 2006/0184214 A1 | 8/2006 | McDaniel | |
| 2006/0187607 A1 | 8/2006 | Mo | |
| 2006/0195168 A1 | 8/2006 | Dunbar | |
| 2006/0199992 A1 | 9/2006 | Eisenberg | |
| 2006/0206103 A1 | 9/2006 | Altshuler | |
| 2006/0206180 A1 | 9/2006 | Alcidi | |
| 2006/0229487 A1 | 10/2006 | Goodwin | |
| 2006/0253176 A1 | 11/2006 | Caruso | |
| 2006/0259102 A1 | 11/2006 | Slatkine | |
| 2006/0271028 A1 | 11/2006 | Altshuler | |
| 2006/0287566 A1 | 12/2006 | Zangen | |
| 2006/0293719 A1 | 12/2006 | Naghavi | |
| 2007/0010766 A1 | 1/2007 | Gil | |
| 2007/0010861 A1 | 1/2007 | Anderson | |
| 2007/0015951 A1 | 1/2007 | Culhane | |
| 2007/0016274 A1 | 1/2007 | Boveja | |
| 2007/0027411 A1 | 2/2007 | Ella | |
| 2007/0083237 A1 | 4/2007 | Teruel | |
| 2007/0088413 A1 | 4/2007 | Weber | |
| 2007/0088419 A1 | 4/2007 | Fiorina | |

(56) References Cited

U.S. PATENT DOCUMENTS

| | | |
|---|---|---|
| 2007/0100195 A1 | 5/2007 | Goodwin |
| 2007/0135811 A1 | 6/2007 | Hooven |
| 2007/0142886 A1 | 6/2007 | Fischell |
| 2007/0173749 A1 | 7/2007 | Williams |
| 2007/0173805 A1 | 7/2007 | Weinberg |
| 2007/0179534 A1 | 8/2007 | Firlik |
| 2007/0198071 A1 | 8/2007 | Ting |
| 2007/0232966 A1 | 10/2007 | Applebaum |
| 2007/0239080 A1 | 10/2007 | Schaden |
| 2007/0244530 A1 | 10/2007 | Ren |
| 2007/0255085 A1 | 11/2007 | Kishawi |
| 2007/0255355 A1 | 11/2007 | Altshuler |
| 2007/0255362 A1 | 11/2007 | Levinson |
| 2007/0260107 A1 | 11/2007 | Mishelevich |
| 2007/0270795 A1 | 11/2007 | Francischelli |
| 2007/0270924 A1 | 11/2007 | McCann |
| 2007/0270925 A1 | 11/2007 | Levinson |
| 2007/0282156 A1 | 12/2007 | Konings |
| 2007/0293911 A1 | 12/2007 | Crowe |
| 2007/0293918 A1 | 12/2007 | Thompson |
| 2008/0009885 A1 | 1/2008 | Del Giglio |
| 2008/0046053 A1 | 2/2008 | Wagner |
| 2008/0077201 A1 | 3/2008 | Levinson |
| 2008/0077202 A1 | 3/2008 | Levinson |
| 2008/0077211 A1 | 3/2008 | Levinson |
| 2008/0082094 A1 | 4/2008 | McPherson |
| 2008/0082153 A1 | 4/2008 | Gadsby |
| 2008/0103565 A1 | 5/2008 | Altshuler |
| 2008/0114199 A1 | 5/2008 | Riehl |
| 2008/0114423 A1 | 5/2008 | Grenon |
| 2008/0132971 A1 | 6/2008 | Pille |
| 2008/0139871 A1 | 6/2008 | Muntermann |
| 2008/0146865 A1 | 6/2008 | Muntermann |
| 2008/0161636 A1 | 7/2008 | Hurme |
| 2008/0167585 A1 | 7/2008 | Khen |
| 2008/0177128 A1 | 7/2008 | Riehl |
| 2008/0183251 A1 | 7/2008 | Azar |
| 2008/0183252 A1 | 7/2008 | Khen |
| 2008/0188915 A1 | 8/2008 | Mills |
| 2008/0195181 A1 | 8/2008 | Cole |
| 2008/0200749 A1 | 8/2008 | Zheng |
| 2008/0200778 A1 | 8/2008 | Taskinen |
| 2008/0228520 A1 | 9/2008 | Day |
| 2008/0234534 A1 | 9/2008 | Mikas |
| 2008/0234609 A1 | 9/2008 | Kreindel |
| 2008/0249350 A1 | 10/2008 | Marchitto |
| 2008/0255572 A1 | 10/2008 | Zeller |
| 2008/0255637 A1 | 10/2008 | Oishi |
| 2008/0262287 A1 | 10/2008 | Dussau |
| 2008/0262574 A1 | 10/2008 | Briefs |
| 2008/0275289 A1 | 11/2008 | Olree |
| 2008/0287839 A1 | 11/2008 | Rosen |
| 2008/0287948 A1 | 11/2008 | Newton |
| 2008/0288035 A1 | 11/2008 | Gill |
| 2008/0306325 A1 | 12/2008 | Burnett |
| 2008/0306326 A1 | 12/2008 | Epstein |
| 2008/0312647 A1 | 12/2008 | Knopp |
| 2009/0005631 A1 | 1/2009 | Simenhaus |
| 2009/0018384 A1 | 1/2009 | Boyden |
| 2009/0018623 A1 | 1/2009 | Levinson |
| 2009/0018624 A1 | 1/2009 | Levinson |
| 2009/0018625 A1 | 1/2009 | Levinson |
| 2009/0018626 A1 | 1/2009 | Levinson |
| 2009/0018627 A1 | 1/2009 | Levinson |
| 2009/0018628 A1 | 1/2009 | Burns |
| 2009/0024192 A1 | 1/2009 | Mulholland |
| 2009/0024193 A1 | 1/2009 | Altshuler |
| 2009/0030352 A1 | 1/2009 | Schultheiss |
| 2009/0036803 A1 | 2/2009 | Warlick |
| 2009/0036938 A1 | 2/2009 | Shipley |
| 2009/0036958 A1 | 2/2009 | Mehta |
| 2009/0043185 A1 | 2/2009 | McAdams |
| 2009/0043188 A1 | 2/2009 | Rauscher |
| 2009/0043293 A1 | 2/2009 | Pankratov |
| 2009/0062885 A1 | 3/2009 | Brighton |
| 2009/0093740 A1 | 4/2009 | Helgeson |
| 2009/0099405 A1 | 4/2009 | Schneider |
| 2009/0108969 A1 | 4/2009 | Sims |
| 2009/0118722 A1 | 5/2009 | Ebbers |
| 2009/0118790 A1 | 5/2009 | Van Herk |
| 2009/0149300 A1 | 6/2009 | Chen |
| 2009/0149925 A1 | 6/2009 | MacDonald |
| 2009/0149929 A1 | 6/2009 | Levinson |
| 2009/0149930 A1 | 6/2009 | Schenck |
| 2009/0156958 A1 | 6/2009 | Mehta |
| 2009/0163761 A1 | 6/2009 | Culhane |
| 2009/0198144 A1 | 8/2009 | Phillips |
| 2009/0209840 A1 | 8/2009 | Axelgaard |
| 2009/0221938 A1 | 9/2009 | Rosenberg |
| 2009/0227830 A1 | 9/2009 | Pillutla |
| 2009/0227831 A1 | 9/2009 | Burnett |
| 2009/0234423 A1 | 9/2009 | Vetanze |
| 2009/0240096 A1 | 9/2009 | Riehl |
| 2009/0248004 A1 | 10/2009 | Altshuler |
| 2009/0254007 A1 | 10/2009 | Schultheiss |
| 2009/0254154 A1 | 10/2009 | De Taboada |
| 2009/0270945 A1 | 10/2009 | Markoll |
| 2009/0281464 A1 | 11/2009 | Cioanta |
| 2009/0284339 A1 | 11/2009 | Choi |
| 2009/0306648 A1 | 12/2009 | Podhajsky |
| 2009/0326528 A1 | 12/2009 | Karni |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0016850 A1 | 1/2010 | Ron Edoute |
| 2010/0030298 A1 | 2/2010 | Martens |
| 2010/0036191 A1 | 2/2010 | Walter |
| 2010/0036368 A1 | 2/2010 | England |
| 2010/0049188 A1 | 2/2010 | Nelson |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0106064 A1 | 4/2010 | Kreindel |
| 2010/0121131 A1 | 5/2010 | Mathes |
| 2010/0130945 A1 | 5/2010 | Laniado |
| 2010/0137760 A1 | 6/2010 | Schulz |
| 2010/0145399 A1 | 6/2010 | Johari |
| 2010/0152522 A1 | 6/2010 | Roth |
| 2010/0152824 A1 | 6/2010 | Allison |
| 2010/0160712 A1 | 6/2010 | Burnett |
| 2010/0168501 A1 | 7/2010 | Burnett |
| 2010/0179372 A1 | 7/2010 | Glassman |
| 2010/0179373 A1 | 7/2010 | Pille |
| 2010/0185042 A1 | 7/2010 | Schneider |
| 2010/0197993 A1 | 8/2010 | Vasishta |
| 2010/0210894 A1 | 8/2010 | Pascual-Leone |
| 2010/0217253 A1 | 8/2010 | Mehta |
| 2010/0222629 A1 | 9/2010 | Burnett |
| 2010/0228075 A1 | 9/2010 | Lu |
| 2010/0228250 A1 | 9/2010 | Brogna |
| 2010/0256438 A1 | 10/2010 | Mishelevich |
| 2010/0256439 A1 | 10/2010 | Schneider |
| 2010/0261992 A1 | 10/2010 | Axelgaard |
| 2010/0274327 A1 | 10/2010 | Carroll |
| 2010/0274329 A1 | 10/2010 | Bradley |
| 2010/0280582 A1 | 11/2010 | Baker |
| 2010/0286470 A1 | 11/2010 | Schneider |
| 2010/0286691 A1 | 11/2010 | Kerr |
| 2010/0298623 A1 | 11/2010 | Mishelevich |
| 2010/0309689 A1 | 12/2010 | Coulson |
| 2010/0315225 A1 | 12/2010 | Teague |
| 2010/0324611 A1 | 12/2010 | Deming |
| 2010/0331602 A1 | 12/2010 | Mishelevich |
| 2010/0331603 A1 | 12/2010 | Szecsi |
| 2010/0331604 A1 | 12/2010 | Okamoto |
| 2011/0004261 A1 | 1/2011 | Sham |
| 2011/0007745 A1 | 1/2011 | Schultz |
| 2011/0009737 A1 | 1/2011 | Manstein |
| 2011/0015464 A1 | 1/2011 | Riehl |
| 2011/0021863 A1 | 1/2011 | Burnett |
| 2011/0046432 A1 | 2/2011 | Simon |
| 2011/0046523 A1 | 2/2011 | Altshuler |

(56) References Cited

U.S. PATENT DOCUMENTS

| | | |
|---|---|---|
| 2011/0060179 A1 | 3/2011 | Aho |
| 2011/0065976 A1 | 3/2011 | Chornenky |
| 2011/0066216 A1 | 3/2011 | Ting |
| 2011/0077451 A1 | 3/2011 | Marchitto |
| 2011/0081333 A1 | 4/2011 | Shantha |
| 2011/0082383 A1 | 4/2011 | Cory |
| 2011/0087312 A1 | 4/2011 | Shanks |
| 2011/0105826 A1 | 5/2011 | Mishelevich |
| 2011/0112520 A1 | 5/2011 | Michael |
| 2011/0118722 A1 | 5/2011 | Lischinsky |
| 2011/0125203 A1 | 5/2011 | Simon |
| 2011/0125213 A1 | 5/2011 | Simon |
| 2011/0130618 A1 | 6/2011 | Ron Edoute |
| 2011/0130713 A1 | 6/2011 | Dufay |
| 2011/0130796 A1 | 6/2011 | Louise |
| 2011/0152967 A1 | 6/2011 | Simon |
| 2011/0172735 A1 | 7/2011 | Johari |
| 2011/0172752 A1 | 7/2011 | Bingham |
| 2011/0190569 A1 | 8/2011 | Simon |
| 2011/0196438 A1 | 8/2011 | Mnozil |
| 2011/0202058 A1 | 8/2011 | Eder |
| 2011/0207988 A1 | 8/2011 | Ruohonen |
| 2011/0208182 A1 | 8/2011 | Szasz |
| 2011/0218464 A1 | 9/2011 | Iger |
| 2011/0224761 A1 | 9/2011 | Manstein |
| 2011/0237921 A1 | 9/2011 | Askin, III |
| 2011/0238050 A1 | 9/2011 | Allison |
| 2011/0238051 A1 | 9/2011 | Levinson |
| 2011/0245900 A1 | 10/2011 | Turner |
| 2011/0263925 A1 | 10/2011 | Bratton |
| 2011/0273251 A1 | 11/2011 | Mishelevich |
| 2011/0275881 A1 | 11/2011 | Aho |
| 2011/0275927 A1 | 11/2011 | Wagner |
| 2011/0276108 A1 | 11/2011 | Crowe |
| 2011/0295160 A1 | 12/2011 | Hart |
| 2011/0300079 A1 | 12/2011 | Martens |
| 2011/0306905 A1 | 12/2011 | Novak |
| 2011/0306943 A1 | 12/2011 | Dunbar |
| 2011/0319700 A1 | 12/2011 | Schneider |
| 2012/0016177 A1 | 1/2012 | Mishelevich |
| 2012/0016359 A1 | 1/2012 | Podhajsky |
| 2012/0022518 A1 | 1/2012 | Levinson |
| 2012/0029264 A1 | 2/2012 | Roth |
| 2012/0029394 A1 | 2/2012 | Babaev |
| 2012/0035608 A1 | 2/2012 | Marchitto |
| 2012/0046598 A1 | 2/2012 | Kardos |
| 2012/0046653 A1 | 2/2012 | Welches |
| 2012/0053449 A1 | 3/2012 | Moses |
| 2012/0101326 A1 | 4/2012 | Simon |
| 2012/0101366 A1 | 4/2012 | Ruohonen |
| 2012/0108883 A1 | 5/2012 | Peterchev |
| 2012/0108884 A1 | 5/2012 | Bechler |
| 2012/0109241 A1 | 5/2012 | Rauscher |
| 2012/0116271 A1 | 5/2012 | Caruso |
| 2012/0150079 A1 | 6/2012 | Rosenberg |
| 2012/0157747 A1 | 6/2012 | Rybski |
| 2012/0158100 A1 | 6/2012 | Schomacker |
| 2012/0172653 A1 | 7/2012 | Chornenky |
| 2012/0191018 A1 | 7/2012 | Willeford |
| 2012/0195100 A1 | 8/2012 | Saitoh |
| 2012/0197361 A1 | 8/2012 | Gonzales |
| 2012/0203054 A1 | 8/2012 | Riehl |
| 2012/0215210 A1 | 8/2012 | Brown |
| 2012/0226139 A1 | 9/2012 | Peyman |
| 2012/0226272 A1 | 9/2012 | Chernov |
| 2012/0226330 A1 | 9/2012 | Kolen |
| 2012/0239120 A1 | 9/2012 | Karni |
| 2012/0239123 A1 | 9/2012 | Weber |
| 2012/0240940 A1 | 9/2012 | Paraschac |
| 2012/0245483 A1 | 9/2012 | Lundqvist |
| 2012/0253098 A1 | 10/2012 | George |
| 2012/0259382 A1 | 10/2012 | Trier |
| 2012/0265111 A1 | 10/2012 | Glenzer |
| 2012/0271206 A1 | 10/2012 | Shalev |
| 2012/0271294 A1 | 10/2012 | Barthe |
| 2012/0277587 A1 | 11/2012 | Adanny |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider |
| 2012/0310311 A1 | 12/2012 | Elkah |
| 2012/0323232 A1 | 12/2012 | Wolf |
| 2012/0330090 A1 | 12/2012 | Sham |
| 2013/0006039 A1 | 1/2013 | Sadler |
| 2013/0012755 A1 | 1/2013 | Slayton |
| 2013/0030239 A1 | 1/2013 | Weyh |
| 2013/0035680 A1 | 2/2013 | Ben-Haim |
| 2013/0035745 A1 | 2/2013 | Ahmed |
| 2013/0053620 A1 | 2/2013 | Susedik |
| 2013/0066309 A1 | 3/2013 | Levinson |
| 2013/0072925 A1 | 3/2013 | Ben-Haim |
| 2013/0072930 A1 | 3/2013 | Ben-Haim |
| 2013/0079684 A1 | 3/2013 | Rosen |
| 2013/0085317 A1 | 4/2013 | Feinstein |
| 2013/0096363 A1 | 4/2013 | Schneider |
| 2013/0103127 A1 | 4/2013 | Mueller |
| 2013/0116758 A1 | 5/2013 | Levinson |
| 2013/0116759 A1 | 5/2013 | Levinson |
| 2013/0123568 A1 | 5/2013 | Hamilton |
| 2013/0123629 A1 | 5/2013 | Rosenberg |
| 2013/0123764 A1 | 5/2013 | Zarsky |
| 2013/0123765 A1 | 5/2013 | Zarsky |
| 2013/0131764 A1 | 5/2013 | Grove |
| 2013/0137918 A1 | 5/2013 | Phillips |
| 2013/0144106 A1 | 6/2013 | Phillips |
| 2013/0144280 A1 | 6/2013 | Eckhouse |
| 2013/0150651 A1 | 6/2013 | Phillips |
| 2013/0150653 A1 | 6/2013 | Borsody |
| 2013/0158440 A1 | 6/2013 | Allison |
| 2013/0158634 A1 | 6/2013 | Ron Edoute |
| 2013/0158636 A1 | 6/2013 | Ting |
| 2013/0172959 A1 | 7/2013 | Azoulay |
| 2013/0178693 A1 | 7/2013 | Neuvonen |
| 2013/0178764 A1 | 7/2013 | Eckhouse |
| 2013/0184693 A1 | 7/2013 | Neev |
| 2013/0190744 A1 | 7/2013 | Avram |
| 2013/0238043 A1 | 9/2013 | Beardall |
| 2013/0238061 A1 | 9/2013 | Ron Edoute |
| 2013/0238062 A1 | 9/2013 | Ron Edoute |
| 2013/0245731 A1 | 9/2013 | Allison |
| 2013/0253384 A1 | 9/2013 | Anderson |
| 2013/0253493 A1 | 9/2013 | Anderson |
| 2013/0253494 A1 | 9/2013 | Anderson |
| 2013/0253495 A1 | 9/2013 | Anderson |
| 2013/0253496 A1 | 9/2013 | Anderson |
| 2013/0261374 A1 | 10/2013 | Elder |
| 2013/0261683 A1 | 10/2013 | Soikum |
| 2013/0267759 A1 | 10/2013 | Jin |
| 2013/0267760 A1 | 10/2013 | Jin |
| 2013/0267943 A1 | 10/2013 | Hancock |
| 2013/0289433 A1 | 10/2013 | Jin |
| 2013/0303904 A1 | 11/2013 | Barthe |
| 2013/0304159 A1 | 11/2013 | Simon |
| 2013/0317281 A1 | 11/2013 | Schneider |
| 2013/0317282 A1 | 11/2013 | Ron Edoute |
| 2013/0331637 A1 | 12/2013 | Greff |
| 2013/0338424 A1 | 12/2013 | Pascual-Leone |
| 2013/0338483 A1 | 12/2013 | Neuvonen |
| 2014/0005645 A1 | 1/2014 | Ben-Haim |
| 2014/0005758 A1 | 1/2014 | Ben-Yehuda |
| 2014/0005759 A1 | 1/2014 | Fahey |
| 2014/0005760 A1 | 1/2014 | Levinson |
| 2014/0012064 A1 | 1/2014 | Riehl |
| 2014/0018767 A1 | 1/2014 | Harris |
| 2014/0025033 A1 | 1/2014 | Mirkov |
| 2014/0025142 A1 | 1/2014 | Zarksy |
| 2014/0046114 A1 | 2/2014 | Nishikawa |
| 2014/0046232 A1 | 2/2014 | Sham |
| 2014/0046339 A1 | 2/2014 | Bonutti |
| 2014/0046423 A1 | 2/2014 | Rajguru |
| 2014/0052029 A1 | 2/2014 | Khen |
| 2014/0066786 A1 | 3/2014 | Naghavi |
| 2014/0067025 A1 | 3/2014 | Levinson |
| 2014/0081069 A1 | 3/2014 | Tai |

(56) References Cited

U.S. PATENT DOCUMENTS

| | | |
|---|---|---|
| 2014/0081348 A1 | 3/2014 | Fischell |
| 2014/0081359 A1 | 3/2014 | Sand |
| 2014/0121446 A1 | 5/2014 | Phillips |
| 2014/0135565 A9 | 5/2014 | Schneider |
| 2014/0148870 A1 | 5/2014 | Burnett |
| 2014/0179980 A1 | 6/2014 | Phillips |
| 2014/0194958 A1 | 7/2014 | Chabal |
| 2014/0200388 A1 | 7/2014 | Schneider |
| 2014/0213844 A1 | 7/2014 | Pilla |
| 2014/0221725 A1 | 8/2014 | Mishelevich |
| 2014/0221990 A1 | 8/2014 | Kreindel |
| 2014/0228620 A1 | 8/2014 | Vasishta |
| 2014/0235926 A1 | 8/2014 | Zangen |
| 2014/0235927 A1 | 8/2014 | Zangen |
| 2014/0235928 A1 | 8/2014 | Zangen |
| 2014/0235929 A1 | 8/2014 | Rohan |
| 2014/0243933 A1 | 8/2014 | Ginggen |
| 2014/0249352 A1 | 9/2014 | Zangen |
| 2014/0249353 A1 | 9/2014 | Pesola |
| 2014/0249355 A1 | 9/2014 | Martinez |
| 2014/0249601 A1 | 9/2014 | Bachinski |
| 2014/0249609 A1 | 9/2014 | Zarsky |
| 2014/0257071 A1 | 9/2014 | Curran |
| 2014/0257145 A1 | 9/2014 | Emery |
| 2014/0257443 A1 | 9/2014 | Baker |
| 2014/0276248 A1 | 9/2014 | Hall |
| 2014/0276693 A1 | 9/2014 | Altshuler |
| 2014/0277219 A1 | 9/2014 | Nanda |
| 2014/0277302 A1 | 9/2014 | Weber |
| 2014/0303425 A1 | 10/2014 | Pilla |
| 2014/0303525 A1 | 10/2014 | Sitharaman |
| 2014/0303696 A1 | 10/2014 | Anderson |
| 2014/0303697 A1 | 10/2014 | Anderson |
| 2014/0309628 A1 | 10/2014 | Vaynberg |
| 2014/0316188 A1 | 10/2014 | Peterchev |
| 2014/0316310 A1 | 10/2014 | Ackermann |
| 2014/0316393 A1 | 10/2014 | Levinson |
| 2014/0316485 A1 | 10/2014 | Ackermann |
| 2014/0324120 A1 | 10/2014 | Bogie |
| 2014/0330067 A1 | 11/2014 | Jordan |
| 2014/0336545 A1 | 11/2014 | Bonutti |
| 2014/0336721 A1 | 11/2014 | Simon |
| 2014/0342428 A1 | 11/2014 | Goodwin |
| 2014/0343351 A1 | 11/2014 | Tojo |
| 2014/0350438 A1 | 11/2014 | Papirov |
| 2014/0357935 A1 | 12/2014 | Ilmoniemi |
| 2014/0364841 A1 | 12/2014 | Kornstein |
| 2014/0371515 A1 | 12/2014 | John |
| 2014/0371812 A1 | 12/2014 | Ackermann |
| 2014/0378875 A1 | 12/2014 | Ron Edoute |
| 2015/0005569 A1 | 1/2015 | Missoli |
| 2015/0005759 A1 | 1/2015 | Welches |
| 2015/0018667 A1 | 1/2015 | Radman |
| 2015/0018692 A1 | 1/2015 | Neuvonen |
| 2015/0018910 A1 | 1/2015 | Chen |
| 2015/0025299 A1 | 1/2015 | Ron Edoute |
| 2015/0025545 A1 | 1/2015 | Grenon |
| 2015/0038768 A1 | 2/2015 | Saitoh |
| 2015/0080769 A1 | 3/2015 | Lotsch |
| 2015/0087888 A1 | 3/2015 | Hurme |
| 2015/0088105 A1 | 3/2015 | Fatemi |
| 2015/0094788 A1 | 4/2015 | Pierenkemper |
| 2015/0112118 A1 | 4/2015 | Mishelevich |
| 2015/0112412 A1 | 4/2015 | Anderson |
| 2015/0119849 A1 | 4/2015 | Aronhalt |
| 2015/0123661 A1 | 5/2015 | Yui |
| 2015/0126914 A1 | 5/2015 | Crunick |
| 2015/0127075 A1 | 5/2015 | Ward |
| 2015/0133717 A1 | 5/2015 | Ghiron |
| 2015/0133718 A1 | 5/2015 | Schneider |
| 2015/0140633 A1 | 5/2015 | Vladila |
| 2015/0141877 A1 | 5/2015 | Feldman |
| 2015/0148858 A1 | 5/2015 | Kaib |
| 2015/0151137 A1 | 6/2015 | Hynninen |
| 2015/0157873 A1 | 6/2015 | Sokolowski |
| 2015/0157874 A1 | 6/2015 | Aho |
| 2015/0165226 A1 | 6/2015 | Simon |
| 2015/0165232 A1 | 6/2015 | Altshuler |
| 2015/0165238 A1 | 6/2015 | Slayton |
| 2015/0174002 A1 | 6/2015 | Burbank |
| 2015/0190648 A1 | 7/2015 | Fischell |
| 2015/0196772 A1 | 7/2015 | Ghiron |
| 2015/0202454 A1 | 7/2015 | Burnett |
| 2015/0213724 A1 | 7/2015 | Shoshani |
| 2015/0216719 A1 | 8/2015 | Debenedictis |
| 2015/0216720 A1 | 8/2015 | Debenedictis |
| 2015/0216816 A1 | 8/2015 | O'Neil |
| 2015/0217127 A1 | 8/2015 | Fischell |
| 2015/0223975 A1 | 8/2015 | Anderson |
| 2015/0227680 A1 | 8/2015 | Mainkar |
| 2015/0238248 A1 | 8/2015 | Thompson |
| 2015/0238771 A1 | 8/2015 | Zársk |
| 2015/0246238 A1 | 9/2015 | Moses |
| 2015/0265830 A1 | 9/2015 | Simon |
| 2015/0265836 A1 | 9/2015 | Simon |
| 2015/0272776 A1 | 10/2015 | Gonzales |
| 2015/0283022 A1 | 10/2015 | Lee |
| 2015/0283025 A1 | 10/2015 | Ledany |
| 2015/0297909 A1 | 10/2015 | Peashock |
| 2015/0314133 A1 | 11/2015 | Yamashiro |
| 2015/0328077 A1 | 11/2015 | Levinson |
| 2015/0328475 A1 | 11/2015 | Kim |
| 2015/0342661 A1 | 12/2015 | Ron Edoute |
| 2015/0342780 A1 | 12/2015 | Levinson |
| 2015/0360045 A1 | 12/2015 | Fischell |
| 2015/0367141 A1 | 12/2015 | Goetz |
| 2015/0375005 A1 | 12/2015 | Segal |
| 2016/0001092 A1 | 1/2016 | Solehmainen |
| 2016/0008619 A1 | 1/2016 | Pell |
| 2016/0015588 A1 | 1/2016 | Tamiya |
| 2016/0015995 A1 | 1/2016 | Leung |
| 2016/0016013 A1 | 1/2016 | Capelli |
| 2016/0020070 A1 | 1/2016 | Kim |
| 2016/0022349 A1 | 1/2016 | Woloszko |
| 2016/0030763 A1 | 2/2016 | Midorikawa |
| 2016/0038183 A1 | 2/2016 | Ignon |
| 2016/0045755 A1 | 2/2016 | Chun |
| 2016/0051401 A1 | 2/2016 | Yee |
| 2016/0051827 A1 | 2/2016 | Ron Edoute |
| 2016/0059027 A1 | 3/2016 | Zangen |
| 2016/0066977 A1 | 3/2016 | Neal, II |
| 2016/0066994 A1 | 3/2016 | Shanks |
| 2016/0067516 A1 | 3/2016 | Schneider |
| 2016/0067517 A1 | 3/2016 | Burnett |
| 2016/0067518 A1 | 3/2016 | Mishelevich |
| 2016/0082290 A1 | 3/2016 | Hart |
| 2016/0086458 A1 | 3/2016 | Biggs |
| 2016/0089550 A1 | 3/2016 | Debenedictis |
| 2016/0096032 A9 | 4/2016 | Schneider |
| 2016/0100977 A1 | 4/2016 | Lee |
| 2016/0106982 A1 | 4/2016 | Cakmak |
| 2016/0106994 A1 | 4/2016 | Crosby |
| 2016/0106995 A1 | 4/2016 | Järnefelt |
| 2016/0114181 A1 | 4/2016 | Vaynberg |
| 2016/0121112 A1 | 5/2016 | Azar |
| 2016/0121118 A1 | 5/2016 | Franke |
| 2016/0129273 A1 | 5/2016 | Park |
| 2016/0129274 A1 | 5/2016 | Park |
| 2016/0136462 A1 | 5/2016 | Lewis, Jr. |
| 2016/0150494 A1 | 5/2016 | Tabet |
| 2016/0151637 A1 | 6/2016 | Abe |
| 2016/0158548 A1 | 6/2016 | Ackermann |
| 2016/0158571 A1 | 6/2016 | Goadsby |
| 2016/0158574 A1 | 6/2016 | Eckhouse |
| 2016/0175193 A1 | 6/2016 | Jung |
| 2016/0175605 A1 | 6/2016 | Borsody |
| 2016/0184601 A1 | 6/2016 | Gleich |
| 2016/0193006 A1 | 7/2016 | Azoulay |
| 2016/0193466 A1 | 7/2016 | Burnett |
| 2016/0206895 A1 | 7/2016 | Zangen |
| 2016/0206896 A1 | 7/2016 | Zangen |
| 2016/0213426 A1 | 7/2016 | Ben-Haim |
| 2016/0213924 A1 | 7/2016 | Coleman |
| 2016/0213943 A1 | 7/2016 | Mauger |

(56) References Cited

U.S. PATENT DOCUMENTS

| | | |
|---|---|---|
| 2016/0220834 A1 | 8/2016 | Schwarz |
| 2016/0220837 A1 | 8/2016 | Jin |
| 2016/0228698 A1 | 8/2016 | Horton |
| 2016/0236004 A1 | 8/2016 | Fischell |
| 2016/0243375 A1 | 8/2016 | Simon |
| 2016/0243376 A1 | 8/2016 | Phillips |
| 2016/0250494 A1 | 9/2016 | Sakaki |
| 2016/0256702 A1 | 9/2016 | Schwarz |
| 2016/0256703 A1 | 9/2016 | Schwarz |
| 2016/0270951 A1 | 9/2016 | Martins |
| 2016/0303393 A1 | 10/2016 | Riehl |
| 2016/0310756 A1 | 10/2016 | Boll |
| 2016/0317346 A1 | 11/2016 | Kovach |
| 2016/0317827 A1 | 11/2016 | Schwarz |
| 2016/0324684 A1 | 11/2016 | Levinson |
| 2016/0338900 A1 | 11/2016 | Khen |
| 2016/0339239 A1 | 11/2016 | Yoo |
| 2016/0346561 A1 | 12/2016 | Ron Edoute |
| 2016/0354035 A1 | 12/2016 | Reihl |
| 2016/0354237 A1 | 12/2016 | Gonzales |
| 2016/0361560 A1 | 12/2016 | Bean |
| 2016/0367795 A1 | 12/2016 | Ackermann |
| 2017/0001024 A1 | 1/2017 | Prouza |
| 2017/0001025 A1 | 1/2017 | Schwarz |
| 2017/0001026 A1 | 1/2017 | Schwarz |
| 2017/0001027 A1 | 1/2017 | Ladman |
| 2017/0001028 A1 | 1/2017 | Ladman |
| 2017/0001029 A1 | 1/2017 | Pribula |
| 2017/0001030 A1 | 1/2017 | Pribula |
| 2017/0007309 A1 | 1/2017 | Debenedictis |
| 2017/0021188 A1 | 1/2017 | Lu |
| 2017/0027595 A1 | 2/2017 | Bonutti |
| 2017/0027596 A1 | 2/2017 | Bonutti |
| 2017/0028166 A1 | 2/2017 | Walpole |
| 2017/0028212 A1 | 2/2017 | Roth |
| 2017/0036019 A1 | 2/2017 | Matsushita |
| 2017/0043177 A1 | 2/2017 | Ron Edoute |
| 2017/0049612 A1 | 2/2017 | Hussain |
| 2017/0050019 A1 | 2/2017 | Ron Edoute |
| 2017/0071790 A1 | 3/2017 | Grenon |
| 2017/0072212 A1 | 3/2017 | Ladman |
| 2017/0087009 A1 | 3/2017 | Badawi |
| 2017/0087373 A1 | 3/2017 | Schwarz |
| 2017/0100585 A1 | 4/2017 | Hall |
| 2017/0105869 A1 | 4/2017 | Frangineas, Jr. |
| 2017/0106201 A1 | 4/2017 | Schwarz |
| 2017/0106203 A1 | 4/2017 | Schneider |
| 2017/0113058 A1 | 4/2017 | Schneider |
| 2017/0120066 A1 | 5/2017 | Phillips |
| 2017/0120067 A1 | 5/2017 | Prouza |
| 2017/0136254 A1 | 5/2017 | Simon |
| 2017/0143958 A1 | 5/2017 | Shalev |
| 2017/0151436 A1 | 6/2017 | Flaherty |
| 2017/0151443 A1 | 6/2017 | Mishelevich |
| 2017/0156907 A1 | 6/2017 | Harris |
| 2017/0156973 A1 | 6/2017 | Hart |
| 2017/0157398 A1 | 6/2017 | Wong |
| 2017/0157430 A1 | 6/2017 | Cheatham, III |
| 2017/0165497 A1 | 6/2017 | Lu |
| 2017/0171666 A1 | 6/2017 | Biggs |
| 2017/0173347 A1 | 6/2017 | Schwarz |
| 2017/0182334 A1 | 6/2017 | Altshuler |
| 2017/0182335 A1 | 6/2017 | Altshuler |
| 2017/0189703 A1 | 7/2017 | Lei |
| 2017/0189707 A1 | 7/2017 | Zabara |
| 2017/0196731 A1 | 7/2017 | Debenedictis |
| 2017/0203117 A1 | 7/2017 | Biginton |
| 2017/0209708 A1 | 7/2017 | Schwarz |
| 2017/0232267 A1 | 8/2017 | Riehl |
| 2017/0239079 A1 | 8/2017 | Root |
| 2017/0239467 A1 | 8/2017 | Shalev |
| 2017/0259077 A1 | 9/2017 | Jin |
| 2017/0266460 A1 | 9/2017 | Upton |
| 2017/0280889 A1 | 10/2017 | Koch |
| 2017/0290708 A1 | 10/2017 | Rapp |
| 2017/0291036 A1 | 10/2017 | Pell |
| 2017/0296838 A1 | 10/2017 | Asahina |
| 2017/0304614 A1 | 10/2017 | Yoo |
| 2017/0304642 A1 | 10/2017 | Ron Edoute |
| 2017/0312536 A1 | 11/2017 | Phillips |
| 2017/0319378 A1 | 11/2017 | Anderson |
| 2017/0325992 A1 | 11/2017 | Debenedictis |
| 2017/0325993 A1 | 11/2017 | Jimenez Lozano |
| 2017/0326042 A1 | 11/2017 | Zeng |
| 2017/0326346 A1 | 11/2017 | Jimenez Lozano |
| 2017/0326357 A1 | 11/2017 | Sacristan |
| 2017/0326377 A1 | 11/2017 | Neuvonen |
| 2017/0333705 A1 | 11/2017 | Schwarz |
| 2017/0333725 A1 | 11/2017 | Hotani |
| 2017/0340884 A1 | 11/2017 | Franke |
| 2017/0340894 A1 | 11/2017 | Rohan |
| 2017/0348143 A1 | 12/2017 | Rosen |
| 2017/0348539 A1 | 12/2017 | Schwarz |
| 2017/0354530 A1 | 12/2017 | Shagdar |
| 2017/0354818 A1 | 12/2017 | De Toni |
| 2017/0361095 A1 | 12/2017 | Mueller |
| 2017/0368332 A1 | 12/2017 | Ackermann |
| 2017/0372006 A1 | 12/2017 | Mainkar |
| 2018/0000347 A1 | 1/2018 | Perez |
| 2018/0000533 A1 | 1/2018 | Boll |
| 2018/0001106 A1 | 1/2018 | Schwarz |
| 2018/0001107 A1 | 1/2018 | Schwarz |
| 2018/0021565 A1 | 1/2018 | Dar |
| 2018/0028831 A1 | 2/2018 | Ron Edoute |
| 2018/0036548 A1 | 2/2018 | Nusse |
| 2018/0043151 A1 | 2/2018 | Ejiri |
| 2018/0056083 A1 | 3/2018 | Jin |
| 2018/0064575 A1 | 3/2018 | Vaynberg |
| 2018/0064950 A1 | 3/2018 | Segal |
| 2018/0064952 A1 | 3/2018 | Zangen |
| 2018/0071544 A1 | 3/2018 | Ghiron |
| 2018/0071545 A1 | 3/2018 | Saitoh |
| 2018/0103991 A1 | 4/2018 | Linhart |
| 2018/0104484 A1 | 4/2018 | Ryaby |
| 2018/0104504 A1 | 4/2018 | Jin |
| 2018/0116905 A1 | 5/2018 | Capelli |
| 2018/0125416 A1 | 5/2018 | Schwarz |
| 2018/0126184 A1 | 5/2018 | Phillips |
| 2018/0133473 A1 | 5/2018 | Yoo |
| 2018/0133498 A1 | 5/2018 | Chornenky |
| 2018/0140860 A1 | 5/2018 | Ledany |
| 2018/0153736 A1 | 6/2018 | Mills |
| 2018/0153760 A1 | 6/2018 | Rosen |
| 2018/0154137 A1 | 6/2018 | Ackermann |
| 2018/0154165 A1 | 6/2018 | Schneider |
| 2018/0154188 A1 | 6/2018 | Altshuler |
| 2018/0161197 A1 | 6/2018 | Baker |
| 2018/0171327 A1 | 6/2018 | Goodwin |
| 2018/0177996 A1 | 6/2018 | Gozani |
| 2018/0178026 A1 | 6/2018 | Riehl |
| 2018/0185081 A1 | 7/2018 | O'Neil |
| 2018/0185189 A1 | 7/2018 | Weber |
| 2018/0200503 A1 | 7/2018 | Ryaby |
| 2018/0214300 A1 | 8/2018 | Anderson |
| 2018/0228646 A1 | 8/2018 | Gonzales |
| 2018/0229048 A1 | 8/2018 | Sikora |
| 2018/0229049 A1 | 8/2018 | Phillips |
| 2018/0236254 A1 | 8/2018 | Schwarz |
| 2018/0250056 A1 | 9/2018 | Avram |
| 2018/0250521 A1 | 9/2018 | Wölfel |
| 2018/0263677 A1 | 9/2018 | Hilton |
| 2018/0264245 A1 | 9/2018 | Edwards |
| 2018/0271767 A1 | 9/2018 | Jimenez Lozano |
| 2018/0280711 A1 | 10/2018 | Sekino |
| 2018/0289533 A1 | 10/2018 | Johnson |
| 2018/0296831 A1 | 10/2018 | Matsushita |
| 2018/0304079 A1 | 10/2018 | Kim |
| 2018/0310950 A1 | 11/2018 | Yee |
| 2018/0318597 A1 | 11/2018 | Simon |
| 2018/0325729 A1 | 11/2018 | Rynerson |
| 2018/0339151 A1 | 11/2018 | De Toni |
| 2018/0345012 A1 | 12/2018 | Schwarz |
| 2018/0345032 A1 | 12/2018 | Lu |
| 2018/0345833 A1 | 12/2018 | Gallagher |

(56) References Cited

U.S. PATENT DOCUMENTS

| | | |
|---|---|---|
| 2018/0353767 A1 | 12/2018 | Biginton |
| 2018/0361154 A1 | 12/2018 | Levin |
| 2018/0369062 A1 | 12/2018 | Khen |
| 2018/0369601 A1 | 12/2018 | Saitoh |
| 2019/0000524 A1 | 1/2019 | Rosen |
| 2019/0000529 A1 | 1/2019 | Kothare |
| 2019/0000663 A1 | 1/2019 | Anderson |
| 2019/0022392 A1 | 1/2019 | Franke |
| 2019/0029876 A1 | 1/2019 | Anderson |
| 2019/0030356 A1 | 1/2019 | Schwarz |
| 2019/0046810 A1 | 2/2019 | Carmeli |
| 2019/0053870 A1 | 2/2019 | Azoulay |
| 2019/0053871 A1 | 2/2019 | Moosmann |
| 2019/0053940 A1 | 2/2019 | Biser |
| 2019/0053941 A1 | 2/2019 | Samson |
| 2019/0053967 A1 | 2/2019 | Moosmann |
| 2019/0060659 A1 | 2/2019 | Ginhoux |
| 2019/0070428 A1 | 3/2019 | Phillips |
| 2019/0111255 A1 | 4/2019 | Errico |
| 2019/0111273 A1 | 4/2019 | Ghiron |
| 2019/0117965 A1 | 4/2019 | Iger |
| 2019/0125477 A1 | 5/2019 | Azoulay |
| 2019/0126036 A1 | 5/2019 | Franco-Obregon |
| 2019/0126041 A1 | 5/2019 | Kerselaers |
| 2019/0134414 A1 | 5/2019 | Prouza |
| 2019/0151655 A1 | 5/2019 | Hall |
| 2019/0160286 A1 | 5/2019 | Yang |
| 2019/0167978 A1 | 6/2019 | Ackermann |
| 2019/0168012 A1 | 6/2019 | Biginton |
| 2019/0183562 A1 | 6/2019 | Widgerow |
| 2019/0192219 A1 | 6/2019 | Kreindel |
| 2019/0192853 A1 | 6/2019 | Kim |
| 2019/0192872 A1 | 6/2019 | Schwarz |
| 2019/0192873 A1 | 6/2019 | Schwarz |
| 2019/0192874 A1 | 6/2019 | Shukla |
| 2019/0192875 A1 | 6/2019 | Schwarz |
| 2019/0201280 A1 | 7/2019 | Bak |
| 2019/0201705 A1 | 7/2019 | Schwarz |
| 2019/0201706 A1 | 7/2019 | Schwarz |
| 2019/0206545 A1 | 7/2019 | Mainkar |
| 2019/0209836 A1 | 7/2019 | Yakoub |
| 2019/0209856 A1 | 7/2019 | Segal |
| 2019/0217090 A1 | 7/2019 | Ryaby |
| 2019/0224490 A1 | 7/2019 | Goadsby |
| 2019/0247654 A1 | 8/2019 | Alyagon |
| 2019/0255346 A1 | 8/2019 | Ghiron |
| 2019/0269909 A1 | 9/2019 | Gozani |
| 2019/0269931 A1 | 9/2019 | Riehl |
| 2019/0275320 A1 | 9/2019 | Kim |
| 2019/0282804 A1 | 9/2019 | Ackermann |
| 2019/0290925 A1 | 9/2019 | Gellman |
| 2019/0290928 A1 | 9/2019 | Biginton |
| 2019/0299016 A1 | 10/2019 | Altman |
| 2019/0299018 A1 | 10/2019 | Chornenky |
| 2019/0314629 A1 | 10/2019 | Kreindel |
| 2019/0314638 A1 | 10/2019 | Kreindel |
| 2019/0328478 A1 | 10/2019 | Schuele |
| 2019/0329065 A1 | 10/2019 | Gandel |
| 2019/0336783 A1 | 11/2019 | Sokolowski |
| 2019/0344091 A1 | 11/2019 | Fischer |
| 2019/0350646 A1 | 11/2019 | Kreindel |
| 2019/0358465 A1 | 11/2019 | Segal |
| 2019/0358466 A1 | 11/2019 | Leung |
| 2019/0365462 A1 | 12/2019 | Casalino |
| 2019/0388697 A1 | 12/2019 | Pell |
| 2019/0388698 A1 | 12/2019 | Schwarz |
| 2020/0001103 A1 | 1/2020 | Schwarz |
| 2020/0016422 A1 | 1/2020 | Ron Edoute |
| 2020/0016423 A1 | 1/2020 | Ron Edoute |
| 2020/0030622 A1 | 1/2020 | Weyh |
| 2020/0037079 A1 | 1/2020 | Biggs |
| 2020/0037080 A1 | 1/2020 | Biggs |
| 2020/0038674 A1 | 2/2020 | John |
| 2020/0038675 A1 | 2/2020 | Neuvonen |
| 2020/0054395 A1 | 2/2020 | Marchitto |
| 2020/0054890 A1 | 2/2020 | Schwarz |
| 2020/0061385 A1 | 2/2020 | Schwarz |
| 2020/0061386 A1 | 2/2020 | Schwarz |
| 2020/0078212 A1 | 3/2020 | Seo |
| 2020/0078599 A1 | 3/2020 | Chen |
| 2020/0086134 A1 | 3/2020 | Johnson |
| 2020/0086314 A1 | 3/2020 | Wang |
| 2020/0093297 A1 | 3/2020 | Dennewald |
| 2020/0094066 A1 | 3/2020 | Heath |
| 2020/0100837 A1 | 4/2020 | Ben-Haim |
| 2020/0100932 A1 | 4/2020 | Hermanson |
| 2020/0101291 A1 | 4/2020 | Yakovlev |
| 2020/0101308 A1 | 4/2020 | Ilmoniemi |
| 2020/0108266 A1 | 4/2020 | Chou |
| 2020/0114160 A1 | 4/2020 | Blendermann |
| 2020/0121984 A1 | 4/2020 | Sama |
| 2020/0129759 A1 | 4/2020 | Schwarz |
| 2020/0138540 A1 | 5/2020 | Azoulay |
| 2020/0139106 A1* | 5/2020 | Chen ..................... H05B 6/105 |
| 2020/0139148 A1 | 5/2020 | Schwarz |
| 2020/0146881 A1 | 5/2020 | Linder |
| 2020/0155221 A1 | 5/2020 | Marchitto |
| 2020/0155866 A1 | 5/2020 | Lu |
| 2020/0163827 A1 | 5/2020 | Hart |
| 2020/0171297 A1 | 6/2020 | Kirson |
| 2020/0179691 A1* | 6/2020 | Chen ..................... A61N 1/0452 |
| 2020/0197696 A1 | 6/2020 | Nagel |
| 2020/0197717 A1 | 6/2020 | Ishikawa |
| 2020/0206522 A1 | 7/2020 | Riehl |
| 2020/0206524 A1 | 7/2020 | Katznelson |
| 2020/0222069 A1 | 7/2020 | Bonutti |
| 2020/0222708 A1 | 7/2020 | Simon |
| 2020/0230431 A1 | 7/2020 | Saitoh |
| 2020/0237424 A1 | 7/2020 | Hunziker |
| 2020/0238076 A1 | 7/2020 | Ackermann |
| 2020/0238098 A1 | 7/2020 | Chornenky |
| 2020/0246617 A1 | 8/2020 | Errico |
| 2020/0251203 A1 | 8/2020 | Mainkar |
| 2020/0269062 A1 | 8/2020 | Chou |
| 2020/0276435 A1 | 9/2020 | Ryaby |
| 2020/0281642 A1 | 9/2020 | Kreindel |
| 2020/0289837 A1 | 9/2020 | Lowin |
| 2020/0289838 A1 | 9/2020 | Schwarz |
| 2020/0306554 A1 | 10/2020 | Ron Edoute |
| 2020/0316379 A1 | 10/2020 | Yoo |
| 2020/0323680 A1 | 10/2020 | Hussain |
| 2020/0324133 A1 | 10/2020 | Schwarz |
| 2020/0330782 A1 | 10/2020 | Zabara |
| 2020/0353244 A1 | 11/2020 | Treen |
| 2020/0353273 A1 | 11/2020 | Yamazaki |
| 2020/0353274 A1 | 11/2020 | Zucco |
| 2020/0360681 A1 | 11/2020 | Ansari |
| 2020/0384281 A1 | 11/2020 | Lay |
| 2020/0398055 A1 | 12/2020 | Jin |
| 2020/0398070 A1 | 12/2020 | Flaherty |
| 2020/0406050 A1 | 12/2020 | Phillips |
| 2021/0001139 A1 | 12/2020 | Casanova |
| 2021/0007668 A1 | 1/2021 | Shukla |
| 2021/0008369 A1 | 1/2021 | Leaper |
| 2021/0008382 A1 | 1/2021 | Crosson |
| 2021/0022914 A1 | 1/2021 | Vaidya |
| 2021/0023364 A1 | 1/2021 | Badawi |
| 2021/0031040 A1 | 1/2021 | Shalev |
| 2021/0038891 A1 | 2/2021 | Franke |
| 2021/0038894 A1 | 2/2021 | Goldfarb |
| 2021/0052216 A1 | 2/2021 | Mowery |
| 2021/0052893 A1 | 2/2021 | Badawi |
| 2021/0052894 A1 | 2/2021 | Suri |
| 2021/0052911 A1 | 2/2021 | Sanderford |
| 2021/0093858 A1 | 2/2021 | Fischer |
| 2021/0093880 A1 | 4/2021 | Thakkar |
| 2021/0106429 A1 | 4/2021 | Zhong |
| 2021/0106842 A1 | 4/2021 | Pacca |
| 2021/0138232 A1 | 4/2021 | Zangen |
| 2021/0146119 A1 | 5/2021 | Paz |
| 2021/0146150 A1 | 5/2021 | Prouza |
| 2021/0146151 A1 | 5/2021 | Frangineas, Jr. |
| 2021/0162211 A1 | 5/2021 | Phillips |
| 2021/0162211 A1 | 6/2021 | Chase |

(56) References Cited

U.S. PATENT DOCUMENTS

| | | |
|---|---|---|
| 2021/0169682 A1 | 6/2021 | Alvarez |
| 2021/0170188 A1 | 6/2021 | Paulus |
| 2021/0178174 A1 | 6/2021 | Lowin |
| 2021/0187278 A1 | 6/2021 | Lu |
| 2021/0196197 A1 | 7/2021 | Leaper |
| 2021/0196957 A1 | 7/2021 | Yakovlev |
| 2021/0205131 A1 | 7/2021 | Grenon |
| 2021/0205631 A1 | 7/2021 | Ghiron |
| 2021/0212634 A1 | 7/2021 | Leaper |
| 2021/0213283 A1 | 7/2021 | Yoo |
| 2021/0219062 A1 | 7/2021 | Biggs |
| 2021/0228898 A1 | 7/2021 | Ghiron |
| 2021/0235901 A1 | 8/2021 | Dennewald |
| 2021/0236809 A1 | 8/2021 | Ackermann |
| 2021/0260369 A1 | 8/2021 | Steier |
| 2021/0260398 A1 | 8/2021 | Bilston |
| 2021/0268299 A1 | 9/2021 | Casalino |
| 2021/0268300 A1 | 9/2021 | Peled |
| 2021/0275747 A1 | 9/2021 | Sobel |
| 2021/0275825 A1 | 9/2021 | Kreindel |
| 2021/0283395 A1 | 9/2021 | Kreindel |
| 2021/0283412 A1 | 9/2021 | Neuvonen |
| 2021/0290969 A1 | 9/2021 | Shukla |
| 2021/0298817 A1 | 9/2021 | Schwarz |
| 2021/0299420 A1 | 9/2021 | Sobel |
| 2021/0299446 A1 | 9/2021 | Errico |
| 2021/0330102 A1 | 10/2021 | Monico |
| 2021/0330987 A1 | 10/2021 | Sun |
| 2021/0361938 A1 | 11/2021 | Gershonowitz |
| 2021/0361939 A1 | 11/2021 | Müller-Bruhn |
| 2021/0361964 A1 | 11/2021 | Pargger |
| 2021/0361965 A1 | 11/2021 | Yakobson |
| 2021/0361967 A1 | 11/2021 | Cohen |
| 2021/0369381 A1 | 12/2021 | Azoulay |
| 2021/0386992 A1 | 12/2021 | Simon |
| 2022/0001168 A1 | 1/2022 | Ko |
| 2022/0001175 A1 | 1/2022 | Ko |
| 2022/0003112 A1 | 1/2022 | Leach |
| 2022/0008741 A1 | 1/2022 | Chornenky |
| 2022/0015942 A1 | 1/2022 | Biser |
| 2022/0016413 A1 | 1/2022 | John |
| 2022/0023654 A1 | 1/2022 | Carmeli |
| 2022/0031408 A1 | 2/2022 | Cai |
| 2022/0032052 A1 | 2/2022 | Kent |
| 2022/0032079 A1 | 2/2022 | Riehl |
| 2022/0036584 A1 | 2/2022 | Sun |
| 2022/0037071 A1 | 2/2022 | Kim |
| 2022/0079811 A1 | 3/2022 | Kleinman Ben Tsvi |
| 2022/0080217 A1 | 3/2022 | Peterchev |
| 2022/0096146 A1 | 3/2022 | Vaynberg |
| 2022/0111223 A1 | 4/2022 | Taylor |
| 2022/0125546 A1 | 4/2022 | Azoulay |
| 2022/0126095 A1 | 4/2022 | Rajguru |
| 2022/0126109 A1 | 4/2022 | Katznelson |
| 2022/0152379 A1 | 5/2022 | Frangineas, Jr. |
| 2022/0152394 A1 | 5/2022 | Levin |
| 2022/0152409 A1 | 5/2022 | Frangineas, Jr. |
| 2022/0161042 A1 | 5/2022 | Lu |
| 2022/0161043 A1 | 5/2022 | Phillips |
| 2022/0161044 A1 | 5/2022 | Phillips |
| 2022/0168136 A1 | 6/2022 | Badawi |
| 2022/0168584 A1 | 6/2022 | Schwarz |
| 2022/0176101 A1 | 6/2022 | Ryaby |
| 2022/0176114 A1 | 6/2022 | Shalev |
| 2022/0176142 A1 | 6/2022 | Ghiron |
| 2022/0176144 A1 | 6/2022 | Velasco Valcke |
| 2022/0184379 A1 | 6/2022 | Lindenthaler |
| 2022/0184389 A1 | 6/2022 | Shalev |
| 2022/0184409 A1 | 6/2022 | Schwarz |
| 2022/0192580 A1 | 6/2022 | Toth |
| 2022/0193437 A1 | 6/2022 | Leung |
| 2022/0203112 A1 | 6/2022 | Iger |
| 2022/0211573 A1 | 7/2022 | Capelli |
| 2022/0212006 A1 | 7/2022 | Rondoni |
| 2022/0226645 A1 | 7/2022 | Shalev |
| 2022/0226646 A1 | 7/2022 | Shalev |
| 2022/0226647 A1 | 7/2022 | Shalev |
| 2022/0226648 A1 | 7/2022 | Shalev |
| 2022/0226649 A1 | 7/2022 | Shalev |
| 2022/0226662 A1 | 7/2022 | Casalino |
| 2022/0233851 A1 | 7/2022 | Shalev |
| 2022/0241107 A1 | 8/2022 | Kim |
| 2022/0241604 A1 | 8/2022 | Lee |
| 2022/0249836 A1 | 8/2022 | Schwarz |
| 2022/0280785 A1 | 9/2022 | Rynerson |
| 2022/0280799 A1 | 9/2022 | Altman |
| 2022/0288409 A1 | 9/2022 | Järnefelt |
| 2022/0362570 A1 | 11/2022 | Pemberton |
| 2022/0370006 A1 | 11/2022 | Zieger |
| 2022/0370814 A1 | 11/2022 | Epshtein |
| 2022/0370818 A1 | 11/2022 | Taylor |
| 2022/0378359 A1 | 12/2022 | Simon |
| 2022/0379114 A1 | 12/2022 | Kent |
| 2022/0395681 A1 | 12/2022 | Martinot |
| 2022/0401256 A1 | 12/2022 | Durand |
| 2023/0001181 A1 | 1/2023 | Paz |
| 2023/0001224 A1 | 1/2023 | Shukla |
| 2023/0013787 A1 | 1/2023 | Sitt |
| 2023/0079691 A1 | 3/2023 | Schwarz |
| 2023/0125236 A1 | 4/2023 | Sandell |
| 2023/0128482 A1 | 4/2023 | Gayes |
| 2023/0130856 A1 | 4/2023 | Sandell |
| 2023/0148962 A1 | 5/2023 | Leaper |
| 2023/0165721 A1 | 6/2023 | Kleinman Ben Tsvi |
| 2023/0191144 A1 | 6/2023 | Ko |
| 2023/0201589 A1 | 6/2023 | Schwarz |
| 2023/0201621 A1 | 6/2023 | Gries |
| 2023/0211171 A1 | 7/2023 | Gries |
| 2023/0211172 A1 | 7/2023 | Oliveros Maita |
| 2023/0218915 A1 | 7/2023 | Casalino |
| 2023/0240784 A1 | 8/2023 | Azoulay |
| 2023/0248989 A1 | 8/2023 | Gries |
| 2023/0285767 A1 | 9/2023 | Kim |
| 2023/0293354 A1 | 9/2023 | Rao |
| 2023/0293901 A1 | 9/2023 | Yun |
| 2023/0293903 A1 | 9/2023 | Järnefelt |
| 2023/0310878 A1 | 10/2023 | Yoon |
| 2023/0355967 A1 | 11/2023 | Kishi |
| 2023/0364413 A1 | 11/2023 | Michael |
| 2023/0372724 A1 | 11/2023 | Casalino |
| 2023/0381499 A1 | 11/2023 | Simon |
| 2023/0381504 A1 | 11/2023 | Yoo |
| 2023/0381507 A1 | 11/2023 | Errico |
| 2023/0381530 A1 | 11/2023 | Kim |
| 2023/0398352 A1 | 12/2023 | Errico |
| 2023/0405306 A1 | 12/2023 | Simon |
| 2023/0405319 A1 | 12/2023 | Simon |
| 2023/0414930 A1* | 12/2023 | Chen ................. A61N 1/3603 |
| 2023/0414960 A1 | 12/2023 | Ghiron |
| 2023/0414961 A1 | 12/2023 | Gries |
| 2024/0001110 A1 | 1/2024 | Ko |
| 2024/0001114 A1 | 1/2024 | Shalev |
| 2024/0009450 A1 | 1/2024 | Ko |
| 2024/0009476 A1 | 1/2024 | Krinke |
| 2024/0024692 A1 | 1/2024 | Khan |
| 2024/0024693 A1 | 1/2024 | Gonzalez |
| 2024/0042228 A1 | 2/2024 | Ghiron |

FOREIGN PATENT DOCUMENTS

| | | |
|---|---|---|
| AU | 2012200610 B2 | 7/2014 |
| AU | 2012244313 B2 | 11/2014 |
| AU | 2014203094 B2 | 7/2015 |
| AU | 2013207657 B2 | 11/2015 |
| BR | PI0701434 A2 | 11/2008 |
| BR | PI0812502 A2 | 6/2015 |
| BR | PI08125023 | 6/2015 |
| CA | 2484880 A1 | 4/2006 |
| CA | 2915928 A1 | 12/2014 |
| CA | 2845438 C | 2/2015 |
| CA | 2604112 C | 7/2016 |
| CA | 3019140 A1 | 10/2017 |
| CA | 3019410 A1 | 10/2017 |
| CA | 3023821 A1 | 11/2017 |

(56) References Cited

FOREIGN PATENT DOCUMENTS

| | | |
|---|---|---|
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 102847231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 206613045 U | 11/2017 |
| CN | 107613914 A | 1/2018 |
| CN | 108882992 A | 11/2018 |
| CN | 109310516 A | 2/2019 |
| CN | 208511024 U | 2/2019 |
| CN | 109865196 A | 6/2019 |
| CN | 110180083 A | 8/2019 |
| CN | 209221337 U | 8/2019 |
| CN | 209221338 U | 8/2019 |
| CN | 110339480 A | 10/2019 |
| CN | 210770219 U | 6/2020 |
| CN | 211357457 U | 8/2020 |
| CN | 111728712 A | 10/2020 |
| CN | 111840804 A | 10/2020 |
| CN | 112023270 A | 12/2020 |
| CN | 112221015 A | 1/2021 |
| CN | 212416683 U | 1/2021 |
| CN | 112472506 A | 3/2021 |
| CN | 112582159 A | 3/2021 |
| CN | 212700107 U | 3/2021 |
| CN | 113041500 A | 6/2021 |
| CN | 213432603 U | 6/2021 |
| CN | 214099374 U | 8/2021 |
| CN | 113499542 A | 10/2021 |
| CN | 113647936 A | 11/2021 |
| CN | 215081635 U | 12/2021 |
| CN | 215084285 U | 12/2021 |
| CN | 215309722 U | 12/2021 |
| CN | 216091887 U | 3/2022 |
| CN | 216169399 U | 4/2022 |
| CN | 216986082 U | 7/2022 |
| CN | 217526108 U | 10/2022 |
| CN | 115364376 A | 11/2022 |
| CN | 217908621 U | 11/2022 |
| CN | 115454185 A | 12/2022 |
| CN | 217960287 U | 12/2022 |
| CN | 218129587 U | 12/2022 |
| CN | 115591124 A | 1/2023 |
| CN | 115639868 A | 1/2023 |
| CN | 115645737 A | 1/2023 |
| CN | 115645748 A | 1/2023 |
| CN | 116328189 A | 6/2023 |
| CN | 219462335 U | 8/2023 |
| DE | 718637 C | 3/1942 |
| DE | 1118902 B | 12/1961 |
| DE | 2748780 A1 | 5/1978 |
| DE | 3205048 A1 | 8/1983 |
| DE | 3340974 A1 | 5/1985 |
| DE | 3610474 A1 | 10/1986 |
| DE | 3825165 A1 | 1/1990 |
| DE | 3340974 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102007044445 A1 | 3/2009 |
| DE | 202010005501 U1 | 8/2010 |
| DE | 102009023855 A1 | 12/2010 |
| DE | 102009049145 A1 | 4/2011 |
| DE | 102009050010 A1 | 5/2011 |
| DE | 102010004307 A1 | 7/2011 |
| DE | 102006024467 B4 | 4/2012 |
| DE | 102011014291 A1 | 9/2012 |
| DE | 102012220121 B3 | 9/2013 |
| DE | 102013211859 B4 | 7/2015 |
| DE | 102014001185 A1 | 7/2015 |
| DE | 102016116399 A1 | 3/2018 |
| DE | 202019100373 U1 | 3/2019 |
| DE | 102017125678 A1 | 5/2019 |
| DE | 202018106565 U1 | 10/2019 |
| DE | 202020100975 U1 | 3/2020 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0039206 B1 | 10/1984 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2069014 A2 | 6/2009 |
| EP | 1883447 B1 | 9/2009 |
| EP | 2139560 A1 | 1/2010 |
| EP | 2124800 B1 | 11/2010 |
| EP | 1917935 B1 | 1/2011 |
| EP | 2308559 A2 | 4/2011 |
| EP | 2139560 B1 | 5/2012 |
| EP | 2461765 A1 | 6/2012 |
| EP | 2564895 A1 | 3/2013 |
| EP | 1863569 B1 | 5/2013 |
| EP | 2069014 B1 | 6/2013 |
| EP | 1850781 B1 | 7/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 2878336 A1 | 6/2015 |
| EP | 2564894 B1 | 11/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3476433 A1 | 5/2019 |
| EP | 3479872 A1 | 5/2019 |
| EP | 3656442 A1 | 5/2020 |
| EP | 3666325 A1 | 6/2020 |
| EP | 3721939 A1 | 10/2020 |
| EP | 3744392 A1 | 12/2020 |
| EP | 3772362 A1 | 2/2021 |
| EP | 3988164 A1 | 4/2022 |
| EP | 3988165 A1 | 4/2022 |
| EP | 4046660 A1 | 8/2022 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 R1 | 10/2015 |
| ES | 2533145 B1 | 7/2016 |
| FR | 2970656 B1 | 6/2014 |
| FR | 3041881 A1 | 4/2017 |

(56) References Cited

FOREIGN PATENT DOCUMENTS

| | | |
|---|---|---|
| FR | 3061012 A1 | 6/2018 |
| FR | 3071395 A1 | 3/2019 |
| GB | 260116 A | 10/1926 |
| GB | 304587 A | 3/1930 |
| GB | 390500 A | 4/1933 |
| GB | 871672 A | 6/1961 |
| GB | 2176009 A | 12/1986 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2521609 A | 7/2015 |
| GB | 2549466 A | 10/2017 |
| GB | 2552004 A | 1/2018 |
| GB | 2552810 A | 2/2018 |
| GB | 2554043 A | 3/2018 |
| GB | 2555809 A | 5/2018 |
| GB | 2567872 A | 5/2019 |
| GB | 2568051 A | 5/2019 |
| GB | 2587392 A | 3/2021 |
| GB | 2591692 A | 8/2021 |
| GB | 2602603 A | 7/2022 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | S5541836 U | 3/1980 |
| JP | H07135376 A | 5/1995 |
| JP | H09276418 A | 10/1997 |
| JP | 2002513621 A | 5/2002 |
| JP | 2003085523 A | 3/2003 |
| JP | 2003305131 A | 10/2003 |
| JP | 2005245585 A | 9/2005 |
| JP | 2006130055 A | 5/2006 |
| JP | 4178762 B2 | 11/2008 |
| JP | 4324673 B2 | 9/2009 |
| JP | 2010504792 A | 2/2010 |
| JP | 2010063007 A | 3/2010 |
| JP | 2010207268 A | 9/2010 |
| JP | 2010533054 A | 10/2010 |
| JP | 2011194176 A | 10/2011 |
| JP | 4837723 B2 | 12/2011 |
| JP | 2013012285 A | 1/2013 |
| JP | 2013063285 A | 4/2013 |
| JP | 2013066597 A | 4/2013 |
| JP | 2013116271 A | 6/2013 |
| JP | 3192971 U | 9/2014 |
| JP | 2015208504 A | 11/2015 |
| JP | 2017070427 A | 4/2017 |
| JP | 2017518857 A | 7/2017 |
| JP | 2018501927 A | 1/2018 |
| JP | 2018018650 A | 2/2018 |
| JP | 2018187510 A | 11/2018 |
| JP | 2018534028 A | 11/2018 |
| KR | 20010095888 A | 11/2001 |
| KR | 200261417 Y1 | 3/2002 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 20100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 101275228 B1 | 6/2013 |
| KR | 20130072244 A | 7/2013 |
| KR | 101292289 B1 | 8/2013 |
| KR | 20130106977 A | 10/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |
| KR | 20150049386 A | 5/2015 |
| KR | 20150058102 A | 5/2015 |
| KR | 101539633 B1 | 7/2015 |
| KR | 20150079619 A | 7/2015 |
| KR | 20150106379 A | 9/2015 |
| KR | 101610762 B1 | 4/2016 |
| KR | 101650155 B1 | 8/2016 |
| KR | 101673182 B1 | 11/2016 |
| KR | 101702400 B1 | 2/2017 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 B1 | 1/2019 |
| KR | 20190005981 A | 1/2019 |
| KR | 101955542 B1 | 5/2019 |
| KR | 102000971 B1 | 7/2019 |
| KR | 20190001779 U | 7/2019 |
| KR | 102063730 B1 | 1/2020 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 102185926 B1 | 12/2020 |
| KR | 20210002973 A | 1/2021 |
| KR | 20210002974 A | 1/2021 |
| KR | 20210105758 A | 8/2021 |
| KR | 102315486 B1 | 10/2021 |
| KR | 20220012823 A | 2/2022 |
| KR | 20220012825 A | 2/2022 |
| KR | 20230045777 A | 4/2023 |
| KR | 20230046655 A | 4/2023 |
| KR | 20230064250 A | 5/2023 |
| KR | 20230094311 A | 6/2023 |
| KR | 20230094312 A | 6/2023 |
| KR | 20230094313 A | 6/2023 |
| KR | 20230134278 A | 9/2023 |
| KR | 20240012685 A | 1/2024 |
| KR | 20240013316 A | 1/2024 |
| MX | 2012012158 A | 4/2014 |
| NL | 7510644 A | 3/1977 |
| NL | 1037451 C2 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 2529471 C2 | 9/2014 |
| RU | 2596053 C2 | 8/2016 |
| RU | 2637104 C2 | 11/2017 |
| RU | 2645923 C2 | 2/2018 |
| SI | 24921 A | 8/2016 |
| TW | 510797 B | 11/2002 |
| TW | 200423986 A | 11/2004 |
| TW | 201825045 A | 7/2018 |
| WO | 9312835 A1 | 7/1993 |
| WO | 9521655 A1 | 8/1995 |
| WO | 9527533 A1 | 10/1995 |
| WO | 9932191 A1 | 7/1999 |
| WO | 0006251 A2 | 2/2000 |
| WO | 0013749 A1 | 3/2000 |
| WO | 0044346 A1 | 8/2000 |
| WO | 0107111 A2 | 2/2001 |

(56) References Cited

FOREIGN PATENT DOCUMENTS

| | | |
|---|---|---|
| WO | 0112089 A1 | 2/2001 |
| WO | 0193797 A2 | 12/2001 |
| WO | 0225675 A1 | 3/2002 |
| WO | 0226147 A1 | 4/2002 |
| WO | 0230511 A2 | 4/2002 |
| WO | 02096514 A1 | 12/2002 |
| WO | 03013334 A2 | 2/2003 |
| WO | 03075820 A1 | 9/2003 |
| WO | 03078596 A2 | 9/2003 |
| WO | 03079916 A1 | 10/2003 |
| WO | 03090863 A1 | 11/2003 |
| WO | 03103769 A1 | 12/2003 |
| WO | 2004078255 A1 | 9/2004 |
| WO | 2004080526 A2 | 9/2004 |
| WO | 2004080527 A2 | 9/2004 |
| WO | 2004087255 A1 | 10/2004 |
| WO | 2004095385 A2 | 11/2004 |
| WO | 2004095835 A1 | 11/2004 |
| WO | 2004096343 A2 | 11/2004 |
| WO | 2004108211 A1 | 12/2004 |
| WO | 2005032660 A1 | 4/2005 |
| WO | 2005044375 A1 | 5/2005 |
| WO | 2005049132 A1 | 6/2005 |
| WO | 2005061051 A2 | 7/2005 |
| WO | 2005065032 A2 | 7/2005 |
| WO | 2005102188 A1 | 11/2005 |
| WO | 2005105013 A2 | 11/2005 |
| WO | 2005107866 A1 | 11/2005 |
| WO | 2006034306 A2 | 3/2006 |
| WO | 2006050279 A2 | 5/2006 |
| WO | 2006061867 A1 | 6/2006 |
| WO | 2006077567 A1 | 7/2006 |
| WO | 2006077582 A2 | 7/2006 |
| WO | 2006115120 A1 | 11/2006 |
| WO | 2006116728 A2 | 11/2006 |
| WO | 2006133636 A1 | 12/2006 |
| WO | 2007005373 A1 | 1/2007 |
| WO | 2007011583 A1 | 1/2007 |
| WO | 2007051896 A1 | 5/2007 |
| WO | 2007096206 A1 | 8/2007 |
| WO | 2007140584 A1 | 12/2007 |
| WO | 2008012827 A2 | 1/2008 |
| WO | 2008049775 A1 | 5/2008 |
| WO | 2008060494 A2 | 5/2008 |
| WO | 2008063478 A1 | 5/2008 |
| WO | 2008085162 A1 | 7/2008 |
| WO | 2008109058 A1 | 9/2008 |
| WO | 2008124112 A1 | 10/2008 |
| WO | 2008127011 A2 | 10/2008 |
| WO | 2008145260 A2 | 12/2008 |
| WO | 2009011708 A1 | 1/2009 |
| WO | 2009013729 A2 | 1/2009 |
| WO | 2009036040 A1 | 3/2009 |
| WO | 2009042863 A1 | 4/2009 |
| WO | 2009044400 A2 | 4/2009 |
| WO | 2009045358 A1 | 4/2009 |
| WO | 2009047628 A2 | 4/2009 |
| WO | 2009083915 A2 | 7/2009 |
| WO | 2009127840 A1 | 10/2009 |
| WO | 2010007614 A2 | 1/2010 |
| WO | 2010022278 A1 | 2/2010 |
| WO | 2010007614 A3 | 5/2010 |
| WO | 2010095147 A2 | 8/2010 |
| WO | 2010129997 A1 | 11/2010 |
| WO | 2010135425 A1 | 11/2010 |
| WO | 2010139376 A1 | 12/2010 |
| WO | 2010151619 A2 | 12/2010 |
| WO | 2011011749 A1 | 1/2011 |
| WO | 2011016019 A1 | 2/2011 |
| WO | 2011021184 A1 | 2/2011 |
| WO | 2011045002 A1 | 4/2011 |
| WO | 2011053607 A1 | 5/2011 |
| WO | 2011058556 A2 | 5/2011 |
| WO | 2011058565 A2 | 5/2011 |
| WO | 2011085020 A1 | 7/2011 |
| WO | 2011137262 A1 | 11/2011 |
| WO | 2011156495 A2 | 12/2011 |
| WO | 2012005766 A1 | 1/2012 |
| WO | 2012024169 A2 | 2/2012 |
| WO | 2012029065 A2 | 3/2012 |
| WO | 2012033932 A2 | 3/2012 |
| WO | 2012040243 A1 | 3/2012 |
| WO | 2012052986 A2 | 4/2012 |
| WO | 2012033932 A3 | 6/2012 |
| WO | 2012073232 A1 | 6/2012 |
| WO | 2012102837 A1 | 8/2012 |
| WO | 2012103632 A1 | 8/2012 |
| WO | 2012106735 A2 | 8/2012 |
| WO | 2012119293 A1 | 9/2012 |
| WO | 2012138169 A2 | 10/2012 |
| WO | 2013021380 A1 | 2/2013 |
| WO | 2013026393 A1 | 2/2013 |
| WO | 2013035088 A1 | 3/2013 |
| WO | 2013074576 A2 | 5/2013 |
| WO | 2013098815 A1 | 7/2013 |
| WO | 2013121265 A1 | 8/2013 |
| WO | 2013131639 A1 | 9/2013 |
| WO | 2013191699 A1 | 12/2013 |
| WO | 2014004051 A2 | 1/2014 |
| WO | 2014009875 A1 | 1/2014 |
| WO | 2014016820 A2 | 1/2014 |
| WO | 2014031857 A2 | 2/2014 |
| WO | 2014049501 A1 | 4/2014 |
| WO | 2014109653 A1 | 7/2014 |
| WO | 2014137344 A1 | 9/2014 |
| WO | 2014141229 A1 | 9/2014 |
| WO | 2014149021 A2 | 9/2014 |
| WO | 2014151431 A2 | 9/2014 |
| WO | 2014163020 A1 | 10/2014 |
| WO | 2014164926 A1 | 10/2014 |
| WO | 2014170887 A2 | 10/2014 |
| WO | 2014176420 A1 | 10/2014 |
| WO | 2015004540 A2 | 1/2015 |
| WO | 2015012639 A1 | 1/2015 |
| WO | 2015012672 A1 | 1/2015 |
| WO | 2015040049 A1 | 3/2015 |
| WO | 2015052705 A1 | 4/2015 |
| WO | 2015083305 A1 | 6/2015 |
| WO | 2015104454 A1 | 7/2015 |
| WO | 2015114629 A1 | 8/2015 |
| WO | 2015137733 A1 | 9/2015 |
| WO | 2015155545 A1 | 10/2015 |
| WO | 2015157725 A1 | 10/2015 |
| WO | 2015170184 A1 | 11/2015 |
| WO | 2015179571 A1 | 11/2015 |
| WO | 2015196164 A2 | 12/2015 |
| WO | 2016005719 A1 | 1/2016 |
| WO | 2016049284 A1 | 3/2016 |
| WO | 2016059556 A1 | 4/2016 |
| WO | 2016116747 A1 | 7/2016 |
| WO | 2016137319 A1 | 9/2016 |
| WO | 2016140871 A1 | 9/2016 |
| WO | 2016183307 A1 | 11/2016 |
| WO | 2016183689 A1 | 11/2016 |
| WO | 2017002065 A1 | 1/2017 |
| WO | 2017055471 A1 | 4/2017 |
| WO | 2017066620 A1 | 4/2017 |
| WO | 2017103923 A1 | 6/2017 |
| WO | 2017106878 A1 | 6/2017 |
| WO | 2017153840 A1 | 9/2017 |
| WO | 2017159959 A1 | 9/2017 |
| WO | 2017160097 A2 | 9/2017 |
| WO | 2017176621 A1 | 10/2017 |
| WO | 2017189890 A1 | 11/2017 |
| WO | 2017191624 A1 | 11/2017 |
| WO | 2017196548 A1 | 11/2017 |
| WO | 2017212253 A1 | 12/2017 |
| WO | 2017212258 A1 | 12/2017 |
| WO | 2018006086 A1 | 1/2018 |
| WO | 2018008023 A1 | 1/2018 |
| WO | 2018044054 A1 | 3/2018 |
| WO | 2018044825 A1 | 3/2018 |
| WO | 2018047164 A1 | 3/2018 |
| WO | 2018052958 A1 | 3/2018 |

(56) References Cited

FOREIGN PATENT DOCUMENTS

| | | |
|---|---|---|
| WO | 2018075394 A1 | 4/2018 |
| WO | 2018075514 A1 | 4/2018 |
| WO | 2018098417 A1 | 5/2018 |
| WO | 2018121998 A2 | 7/2018 |
| WO | 2018122535 A1 | 7/2018 |
| WO | 2018132678 A1 | 7/2018 |
| WO | 2017160097 A3 | 9/2018 |
| WO | 2018208992 A1 | 11/2018 |
| WO | 2018221903 A2 | 12/2018 |
| WO | 2018235629 A1 | 12/2018 |
| WO | 2019021288 A1 | 1/2019 |
| WO | 2019083863 A1 | 5/2019 |
| WO | 2019099068 A1 | 5/2019 |
| WO | 2019111053 A2 | 6/2019 |
| WO | 2019117740 A2 | 6/2019 |
| WO | 2019118709 A1 | 6/2019 |
| WO | 2019120420 A1 | 6/2019 |
| WO | 2019126792 A1 | 6/2019 |
| WO | 2019142196 A1 | 7/2019 |
| WO | 2019144316 A1 | 8/2019 |
| WO | 2019145762 A1 | 8/2019 |
| WO | 2019150378 A1 | 8/2019 |
| WO | 2019154834 A1 | 8/2019 |
| WO | 2019154837 A1 | 8/2019 |
| WO | 2019154839 A1 | 8/2019 |
| WO | 2019164471 A1 | 8/2019 |
| WO | 2019166965 A1 | 9/2019 |
| WO | 2019173866 A1 | 9/2019 |
| WO | 2019183306 A1 | 9/2019 |
| WO | 2019183622 A1 | 9/2019 |
| WO | 2019193000 A1 | 10/2019 |
| WO | 2019212972 A1 | 11/2019 |
| WO | 2020002801 A1 | 1/2020 |
| WO | 2020035852 A2 | 2/2020 |
| WO | 2020041502 A1 | 2/2020 |
| WO | 2020041633 A1 | 2/2020 |
| WO | 2020044331 A1 | 3/2020 |
| WO | 2020053848 A1 | 3/2020 |
| WO | 2020065651 A1 | 4/2020 |
| WO | 2020072243 A1 | 4/2020 |
| WO | 2020092653 A1 | 5/2020 |
| WO | 2020142470 A1 | 7/2020 |
| WO | 2020144486 A1 | 7/2020 |
| WO | 2020174444 A1 | 9/2020 |
| WO | 2020183508 A1 | 9/2020 |
| WO | 2020190514 A1 | 9/2020 |
| WO | 2020194278 A1 | 10/2020 |
| WO | 2020208590 A1 | 10/2020 |
| WO | 2020227288 A1 | 11/2020 |
| WO | 2020251177 A1 | 12/2020 |
| WO | 2020264263 A1 | 12/2020 |
| WO | 2021003473 A1 | 1/2021 |
| WO | 2021013654 A1 | 1/2021 |
| WO | 2021102365 A1 | 5/2021 |
| WO | 2021232096 A1 | 11/2021 |
| WO | 2022019695 A1 | 1/2022 |
| WO | 2022019696 A1 | 1/2022 |
| WO | 2022041657 A1 | 3/2022 |
| WO | 2022065800 A1 | 3/2022 |
| WO | 2022085989 A1 | 4/2022 |
| WO | 2022099067 A1 | 5/2022 |
| WO | 2022118028 A1 | 6/2022 |
| WO | 2022119577 A1 | 6/2022 |
| WO | 2022122923 A1 | 6/2022 |
| WO | 2022128991 A1 | 6/2022 |
| WO | 2022144555 A1 | 7/2022 |
| WO | 2022171218 A1 | 8/2022 |
| WO | 2022182756 A1 | 9/2022 |
| WO | 2022197674 A2 | 9/2022 |
| WO | 2022246320 A1 | 11/2022 |
| WO | 2022256388 A1 | 12/2022 |
| WO | 2023003501 A1 | 1/2023 |
| WO | 2023281448 A1 | 1/2023 |
| WO | 2023010656 A1 | 2/2023 |
| WO | 2023011503 A1 | 2/2023 |
| WO | 2023066020 A1 | 4/2023 |
| WO | 2023080310 A1 | 5/2023 |
| WO | 2023108881 A1 | 6/2023 |
| WO | 2023118023 A2 | 6/2023 |
| WO | 2023130108 A1 | 7/2023 |
| WO | 2023175610 A1 | 9/2023 |
| WO | 2023238038 A1 | 12/2023 |
| WO | 2023238039 A1 | 12/2023 |
| WO | 2023238040 A1 | 12/2023 |
| WO | 2023238041 A1 | 12/2023 |

OTHER PUBLICATIONS

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Callaghan, M.J., et al., "Electric Muscle Stimulation of the Quadriceps in the Treatment of Patellofemoral Pain," Archives of Physical Medicine and Rehabilitation 85(6): 956-962, W.B. Saunders, United Staes (Jun. 2004).

Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).

Caress, J.B., et al., "A Novel Method of Inducing Muscle Cramps Using Repetitive Magnetic Stimulation," Muscle Nerve, 23(1):126-128, John Wiley and Sons, United States, (Jan. 2000).

Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.

Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.

Certain Non-Invasive Aesthetic Body Contouring Devices, Components Thereof, and Methods of Using the Same, Inv. No. 337-TA-1219, Complaint, Aug. 5, 2020, 93 pages.

Certain Non-Invasive Aesthetic Body Contouring Devices, Components Thereof, and Methods of Using the Same, Inv. No. 337-TA-1219, Joint Claim Construction Chart, Dec. 14, 2020, 15 pages.

Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.

Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.

Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.

Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.

Certain Non-Invasive Aesthetic Body Contouring Devices, Components Thereof, and Methods of Using the Same; Inv. No. 337-TA-1219, Joint Claim Construction Chart, Dec. 18, 2020, 15 pages.

Certain Non-Invasive Aesthetic Body Contouring Devices, Components Thereof, and Methods of Using the Same; Inv. No. 337-

(56) References Cited

OTHER PUBLICATIONS

TA-1219, Respondents' List of Proposed Claim Constructions and Their Intrinsic and Extrinsic Support, filed Dec. 15, 2020, 23 pages.
Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.
Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.
Certain Non-Invasive Aesthetic Body-Contouring Devices, Components Thereof, and Methods of Using the Same, Inv. No. 337-TA-1219, Order No. 21 (Initial Determination), Apr. 28, 2021, 5 pages.
Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.
Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.
Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.
Chattanooga Group of Encore Medical, L.P., "Intelect SWD 100 User Manual, Operation and Installation Instructions for Intelect SWD 00—Model 1600," All pages (2009).
Chesterton, L.S., et al., "Skin Temperature Response to Cryotherapy," Archives of Physical Medicine and Rehabilitation, 83(4):543-549, W.B. Saunders, United States (Apr. 2002).
Clinical Application of Electro Magnetic Stimulation, SALUS-TALENT, Korea Society of interventional Muscle and Soft Tissue Stimulation Therapy, CR Technology, 141 pages.
Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).
Colson, S., et al., "Re-Examination of Training Effects by Electrostimulation in the Human Elbow Musculoskeletal System," International Journal of Sports Medicine 21(4):281-288, Stuttgart, Thieme (May 2000).
Course in Physical Therapy, Presentation, Jan. 4, 2013, 156 pages.
CR Technologies, "Notification of medical device manufacturing item permission, Salus Talent Pop KFDA Approval Document" (English Translation), 3 pages (Sep. 2011).
CR Technologies, "Salus Talent Pop Manual KFDA First Approval Document" (English Translation), Nov. 25, 2011, 47 pages.
CR Technology Co, Ltd., "Salus-Talent DOUBLE Sales Brochure" 2 pages, (Oct. 2020).
CR Technology Co. Ltd., "Medical Laser Irradiator Salus-Talent-Pop User Manual Version 1.00" (Nov. 2020).
CR Technology Co. Ltd., Salus Talent Pop User Manual, Ver. 1.00, 32 pages, Approx. 2012.
CR Technology, SALUS-TALENT, Technical File of Electromagnetic Stimulator, Document No. TF-C05, 2008, 241 pages.
CR Technology, Technology for Health and Business for Human Being, investor relations, 2008, 21 pages.
CryoGenTech GmbH, Company Profile, Creating CRYO, Medica, 9 pages.
Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).
Cutera, truSculptflex, Brochure, dated 2019, 2 pages.
CynoSure, SculpSure TM, The New Shape of Energy-Based body Contouring, 2015, Cynosure Inc, 2 pages.
Cynosure, Smooth Shapes XV, Now with Smoothshape petite, Transforming non-invasive Body Shaping, Retrieved from the Internet: (www.cynosure.com), 2011, Cynosure Inc, 8 pages.
Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).
Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).
Department of Health and Human Services, 501 (k) Letter and Summary for K163415 SlimShape System Powered Muscle Stimulator, dated Apr. 20, 2017, 8 pages.
Department of Health and Human Services, 501 (k) Letter and Summary for K182106 BTL 799-2T Powered Muscle Stimulator, dated Oct. 23, 2018, 9 pages.
Department of Health and Human Services, 501 (k) Letter and Summary for K190456 BTL 799-2L Powered Muscle Stimulator, dated Jul. 5, 2019, 9 pages.
Department of Health and Human Services, 501 (k) Letter and Summary for K192224 BTL 899 Powered Muscle Stimulator, dated Dec. 5, 2019, 11 pages.
Depatment of Health and Human Services, 501(k) Letter and Summary for K092476 Body Control System 4M Powered Muscle Stimulator, dated May 7, 2010, 5 pages.
Depatment of Health and Human Services, 501(k) Letter and Summary for K160992 HPM-6000 Powered Muscle Stimulator, dated Oct. 21, 2016, 9 pages.
Doucet, B., et al., "Neuromuscular Electrical Stimulation for Skeletal Muscle Function," Yale Journal of Biology and Medicine 85:201-215, Yale Journal of Biology and Medicine, United States (Jun. 2012).
Dudley, G. and Stevenson, S., "Use of Electrical Stimulation in Strength and Power Training," Special Problems in Strength and Power Training :426-435 (2003).
Storz Medical Ag, K203710 510(k) Summary, Storz Medical MAGNETOLITH Muscle Stimulator, 7 pages (May 2021).
Struppler, A., et al., "Facilitation of Skilled Finger Movements by Repetitive Peripheral Magnetic Stimulation (RPMS)—A New Approach in Central Paresis.," NeuroRehabilitation 18(1):69-82, IOS Press, Amsterdam (2003).
Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).
Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).
Super Inductive System Seat, leaflet, 2 pages (2021).
Super Inductive System Seat, User's Manual, 20 pages (2019).
Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).
Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).
Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).
Taylor, J.L, "Magnetic Muscle Stimulation Produces Fatigue Without Effort," Journal of Applied Physiology (1985) 103(3):733-734, American Physiological Society, United States, (Sep. 2007).
Tesla Stym, Iskra Medical, Tone the inner muscle with FMS Functional Magnetic Stimulation, 2013, 4 pages.
The Burn Centre Care, Education, 3 pages, printed from internet Nov. 13, 2017.

(56) References Cited

OTHER PUBLICATIONS

The Magstim Company Ltd, K080499 510(k) Summary, Magstim Double 70mm Air Film Coil, All pages (Dec. 2008).
The Magstim Company Ltd., K130403 510(k) Summary, Magstim D702 coil, 8 pages (Aug. 2013).
Thermi Launches Arvati, powered by Thermi, with newest advances in True Temperature Controlled Radiofrequency Technology, 5 pages (2018).
Thermi Smooth TM 250, High Power Temperature Controlled Radio Frequency, Thermi Aesthetics, 25 pages.
Thompson, M.T., "Inductance Calculation Techniques—Part I: Classical Methods," Power Control and Intelligent Motion, 25(12):40-45, (Dec. 1999) http://www.pcim.com/.
Thompson, M.T., "Inductance Calculation Techniques—Part II: Approxmiations and Handbook Methods," Power Control and Intelligent Motion, 11 pages (Dec. 1999) http://www.pcim.com/.
Tomek, J., et al., "Magnetopneumography—Incorporation of optical position reference," Journal of Electrical Engineering, All pages (2012).
Torbergsen, T., "Abstracts of the International Course and Symposium in Single Fibre EMG and Quantitative EMG Analysis. Tromsø, Norway, Jun. 4-8, 1984," Muscle and Nerve 9(6):562-574, John Wiley and Sons, United States (Jul.-Aug. 1986).
TriLipo MED Procedure, http://download.lifvation.com/Maximus_TriLipoMED_Intro.pdf, Apr. 2013, 76 pages.
TSEM Med Swiss SA, Diamagnetic Therapy: A Revolutionary Therapy, CTU Mega 20 Catalogue, dated 2016, 24 pages, Lugano Switzerland.
Turley, J., "Agilent Technologies Announces 30 MHz Function/Arbitrary Waveform Generators with Unparalleled Signal Accuracy," Elec. Eng'g J., URL: <https://www.eejoumal.com/article/20100804-03> (Aug. 4, 2010), 8 pages.
U.S. Appl. No. 60/848,720, inventor Burnett, D., filed Sep. 30, 2006 (Not Published). 41 pages.
U.S. Appl. No. 62/331,060, inventor Schwarz, T., filed May 3, 2016 (Not Published). 32 pages.
U.S. Appl. No. 62/331,072, inventor Schwarz, T., filed May 3, 2016 (Not Published). 34 pages.
U.S. Appl. No. 62/331,088, inventor Schwarz, T., filed May 3, 2016 (Not Published). 38 pages.
U.S. Appl. No. 62/333,666, inventor Schwarz, T., filed May 9, 2016 (Not Published). 39 pages.
U.S. Appl. No. 62/351,156, inventor Schwarz, T., filed Jun. 16, 2016 (Not Published). 41 pages.
U.S. Appl. No. 62/357,679, inventor Schwarz, T., filed Jul. 1, 2016 (Not Published). 22 pages.
U.S. Appl. No. 62/440,905, inventors Schwarz, T. et al., filed Dec. 30, 2016 (Not Published). 32 pages.
U.S. Appl. No. 62/440,912, inventors Schwarz, T. et al., filed Dec. 30, 2016 (Not Published). 19 pages.
U.S. Appl. No. 62/440,922, inventor Schwarz, T., filed Dec. 30, 2016 (Not Published). 10 pages.
U.S. Appl. No. 62/440,936, inventor Schwarz, T., filed Dec. 30, 2016 (Not Published). 9 pages.
U.S. Appl. No. 62/440,940, inventor Schwarz, T., filed Dec. 30, 2016 (Not Published). 8 pages.
U.S. Appl. No. 62/441,805, inventor Prouza, O., filed Jan. 3, 2017 (Not Published). 26 pages.
U.S. Appl. No. 62/786,731, inventor Schwarz, T., filed Dec. 31, 2018 (Not Published). 115 pages.
Ultra Slim Professional, The very best body Contouring, Wardphotonics LLC, 2018, 16 pages.
Unique Multi-Treatment Platform for, Feminine Health, Venus Fiore, Jul. 24, 2018, 12 pages.
Urban, J., "Magnetotherapy and Physiotherapy," 40 pages.
URO Diagnostic Clinic, Now in UDC, Automated pelvic floor muscle training, QRS International AG, 16 Pages.
User Guide, Salus Talent Pro, REMED, High Intensity Electro magnetic Field Therapy—2 Channel, 2017, Version M-1.0.0, 45 pages.
User Guide, Salus Talent, REMED, High Intensity Electro magnetic Field Therapy, Version. M-1.0.0, 2017, 40 pages.
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Manual: Electro-magnetic Stimulator, SALUS-TALENT, Version 1.00, Rehabilitation Medical Company,2013, 34 Pages.
User Manual: Regenetron PRO, System Information, Regenetron PRO User Manual, Nov. 2014, 7 Pages.
User's Manual: BTL-6000, Super Inductive System Elite, BBTL Industries Ltd, United Kingdom, Sep. 2016, 36 pages.
Vance, C., et al., "Effects of Transcutaneous Electrical Nerve Stimulation on Pain, Pain Sensitivity, and Function in People with Knee Osteoarthritis," Physical Therapy 92:898-910 (2012).
Vanquish Operator's Manual, BTL, 2012, 48 Pages.
Venus Concept Ltd., K111670 510(k) Summary, Venus Freeze (MP)2, 6 pages (Mar. 2012).
Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).
DuoMAG Magnetic Stimulator, Alien Technik User Manuel, Jun. 26, 2012,48 pages, Version 2.1.
Dybek, T., et al., "Impact of 10 Sessions of Whole Body Cryostimulation on Aerobic and Anaerobic Capacity and on Selected Blood Count Parameters," Biology of Sport, 29(1):39-43 (Jan. 2012).
Dynatronics., "Better Rehab Solutions for Better Outcomes," Rehabilitation Products Guide 2.3, 2017, 52 pages.
Edoute, Scientific background Venus, Jan. 1, 2018, 2 pages.
Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--8928746.html), 2019, 5 pages.
Elamed, Magnetic Therapeutic Apparatus for Running Pulse Magfield small-sized ALMAG-01 Manual, 22 pages, 2020.
Eliminate Stubborn Fat without Surgery or Downtime and Feel Great From Every Angle, FEAR NO MIRROR®, Consultation Guide, Coolsculpting, 2014, 20 pages.
EndyMed PRO, 3 Deep, 3 Dimensional Control of the Target Zone, A Brilliant RadioFrequency Innovation, Eclipse Aesthetics, 7 Pages.
Energist Ltd—Acquired Chromogenez—Old Account, iLipo—Laser Liposuction (i-Lipo), Video Screenshots, Aug. 10, 2009, 5 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
European Commission, "Neurogenerative Disorders," 10 pages printed Dec. 27, 2016.
European Commission, Neuodegenerative Disorders, 10 pages printed Dec. 27, 2016.
European Patent Office, International Search Report and Written Opinion for International Application No. PCT/IB2016/053930, dated Dec. 12, 2016, 19 pages.
Exilis, Operator's Manual, BTL, 2012, 44 Pages.
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
FDA letter to Venus Legacy, Dec. 19, 2014, 7 pages.
File History for U.S. Appl. No. 62/812,123, to Caselino et al., filed Feb. 28, 2019.
File History for U.S. Appl. No. 62/884,099, to Caselino et al., filed Aug. 7, 2019.
File History for U.S. Appl. No. 62/908,741, to Caselino et al., filed Oct. 1, 2019.
Final Office Action mailed Sep. 12, 2016, in U.S. Appl. No. 14/873,110, Ladman, J., et al., filed Oct. 1, 2015.

(56) References Cited

OTHER PUBLICATIONS

Final Office Action mailed Apr. 18, 2016, in U.S. Appl. No. 14/700,349, Schwarz T., et al., filed Apr. 30, 2015.
Final Office Action mailed Aug. 12, 2016, in U.S. Appl. No. 14/926,365, Prouza, O., et al., filed Oct. 29, 2015.
Final Office Action mailed Dec. 1, 2016, in U.S. Appl. No. 14/789,658, Ladman, J., et al., filed Jul. 1, 2015.
Final Office Action mailed Jan. 27, 2017 in U.S. Appl. No. 15/060,375, Schwarz, T., et al., filed Mar. 3, 2016.
Final Office Action mailed Jan. 4, 2017, in U.S. Appl. No. 15/073,318, Schwarz, T., et al., filed Mar. 17, 2016.
Final Office Action mailed Jul. 1, 2016, in U.S. Appl. No. 14/870,713, Schwarz, T., et al., filed Sep. 30, 2015.
Final Office Action mailed Jul. 14, 2017, in U.S. Appl. No. 15/344,811, Schwarz, T., et al., filed Nov. 7, 2016.
Final Office Action mailed Jun. 22, 2017, in U.S. Appl. No. 15/151,012, Schwarz, T., et al., filed May 10, 2016.
Final Office Action mailed Jun. 26, 2017, in U.S. Appl. No. 15/099,274, Pribula, O., et al., filed Apr. 14, 2016.
Final Office Action mailed May 20, 2016, in U.S. Appl. No. 14/697,934, Zarsky, J., et al., filed Apr. 28, 2015.
Final Office Action mailed Nov. 4, 2016, in U.S. Appl. No. 14/951,093, Schwarz, T., et al., filed Nov. 24, 2015.
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fisher, R., et al., "ILAE Official Report: a Practical Clinical Definition of Epilepsy," Epilepsia, 55(4):475-482, Blackwell Science, United States (Apr. 2014).
FMS Tesla Stym—AKCE, Medila Cenova nabidika, Price offerc. 191, 24 pages.
Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003). 3 pages.
Geddes, L.A., "History of Magnetic Stimulation of the Nervous System," Journal of Clinical Neurophysiology 8(1):3-9, Lippincott Williams and Wilkins, United States (Jan. 1991).
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorgey, A., et al., "Effects of Electrical Stimulation Parameters on Fatigue in Skeletal Muscle," The Journal of Orthopaedic and Sports Physical Therapy 39(9):684-692, Williams and Wilkins, United States (Sep. 2009).
Gorodnichev, R.M., "Magnetic Stimulation of Muscles as New Method to Enhance Their Strength," Velikie Luki State Academy of Physical Culture and Sport, Velikie Luki, 2016, 5 pages.
Gorodnichev, R.M., et al., "The Effect of Electromagnetic Stimulation on the Parameters of Muscular Strength," Human Physiology 40:65-69 (2014).
Guangzhou HEMS Tech, PEMF Star, May 31, 2019, 5 pages.
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, B.H., et al., "Development of four-channel magnetic nerve stimulator," 2001 Proceedings of the 23rd Annual EMBS International Conference, pp. 1325-1327, Turkey (2001).
Han, T.R., et al., "Magnetic Stimulation of the Quadriceps Femoris Muscle: Comparison of Pain With Electrical Stimulation," American Journal of Physical Medicine and Rehabilitation, 85(7):593-599, Lippincott Williams and Wilkins, United States, (Jul. 2006).
Harkey, M.S., "Disinhibitory Interventions and Voluntary Quadriceps Activation: A Systematic Review," Journal of Athletic Training 49(3):411-421, National Athletic Trainers' Association, United States (2014).
Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Lin, V.W., et al., "Functional Magnetic Stimulation of the Respiratory Muscles in Dogs," Muscle and Nerve 21(8):1048-1057, John Wiley and Sons, United States (Aug. 1998).
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).
Linehan, C., et al., Brainwave the Irish Epilepsy Assoication, "The Prevalence of Epilepsy in Ireland" Summary Report, pp. 1-8 (May 2009).
Lotz, B.P., et al., "Preferential Activation of Muscle Fibers with Peripheral Magnetic Stimulation of the Limb," Muscle and Nerve, 12(8):636-639, John Wiley and Sons, United States (Aug. 1989).
*Lumenis Be Ltd. v. BTL Healthcare Technologies A. S.*, PTAB-IPR2021-01403, Declaration of Dr. Marom Bikson (EX1002), Sep. 13, 2021, 243 pages.
*Lumenis Be Ltd. v. BTL Healthcare Technologies A. S.*, PTAB-IPR2021-01403, U.S. Pat. No. 10,821,295 Petition for Inter Partes Review, Sep. 13, 2021, 84 pages.
*Lumenis Be Ltd. v. BTL Healthcare Technologies A. S.*, PTAB-IPR2021-01404, Declaration of Dr. MaromBikson (EX1002), Sep. 13, 2021, 245 pages.
*Lumenis Be Ltd. v. BTL Healthcare Technologies A. S.*, PTAB-IPR2021-01404, U.S. Pat. No. 10,124,187 Petition for Inter Partes Review, Sep. 13, 2021, 82 pages.
*Lumenis Be Ltd. v. BTL Healthcare Technologies A. S.*, PTAB-IPR2021-01405. U.S. Pat. No. 10,124,187 Petition for Inter Partes Review, Sep. 13, 2021, 86 pages.
*Lumenis Be Ltd. v. BTL Healthcare Technologies A.S.*, PTAB-IPR2021-01402, Declaration of Dr. Marom Bikson (EX1002), Sep. 13, 2021, 244 pages.
*Lumenis Be Ltd. v. BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd. v. BTL Healthcare Technologies A.S.*, PTAB-IPR2021-01405, Declaration of Dr. Marom Bikson (EX1002), Sep. 13, 2021, 247 pages.
*Lumenis Be Ltd. v. BTL Healthcare Technologies A.S.*, PTAB-IPR2022-00126, Declaration of Dr. Marom Bikson (EX1002), Nov. 10, 2021, 263 pages.
*Lumenis Be Ltd. v. BTL Healthcare Technologies A.S.*, PTAB-IPR2022-00126, U.S. Pat. No. 10,695,576 Petition for Inter Partes Review, Nov. 10, 2021, 83 pages.
*Lumenis Be Ltd. v. BTL Healthcare Technologies A.S.*, PTAB-IPR2022-00127, Declaration of Dr. Marom Bikson (EX1002), Nov. 10, 2021, 269 pages.

(56) References Cited

OTHER PUBLICATIONS

*Lumenis Be Ltd.* v. *BTL Healthcare Technologies A.S.*, PTAB-IPR2022-00127, U.S. Pat. No. 10,695,576 Petition for Inter Partes Review, Nov. 10, 2021, 84 pages.
*Lumenis Be Ltd.* v. *BTL Healthcare Technologies A.S.*, PTAB-IPR2022-00451, Declaration of Dr. Marom Bikson (EX1002), Jan. 24, 2022, 236 pages.
*Lumenis Be Ltd.* v. *BTL Healthcare Technologies A.S.*, PTAB-IPR2022-00451, U.S. Pat. No. 10,806,943 Petition for Inter Partes Review, Jan. 24, 2022, 87 pages.
*Lumenis Be Ltd.* v. *BTL Healthcare Technologies A.S.*, PTAB-IPR2022-00452, Declaration of Dr. Marom Bikson (EX1002), Jan. 24, 2022, 229 pages.
*Lumenis Be Ltd.* v. *BTL Healthcare Technologies A.S.*, PTAB-IPR2022-00452, U.S. Pat. No. 10,806,943 Petition for Inter Partes Review, Jan. 24, 2022, 81 pages.
*Lumenis Ltd.* v. *BTL Healthcare Technologies A.S.*, PTAB-IPR2021-01273, Declaration of Dr. MaromBikson (EX1002), Aug. 13, 2021, 225 pages.
*Lumenis Ltd.* v. *BTL Healthcare Technologies A.S.*, PTAB-IPR2021-01273, U.S. Pat. No. 10,478,634, Petition for Inter Partes Review, Aug. 13, 2021, 70 pages.
*Lumenis Ltd.* v. *BTL Healthcare Technologies A.S.*, PTAB-IPR2021-01275, Declaration of Dr. MaromBikson (EX1002), Aug. 5, 2021, 282 pages.
*Lumenis Ltd.* v. *BTL Healthcare Technologies A.S.*, PTAB-IPR2021-01275, U.S. Pat. No. 10,632,321, Petition for Inter Partes Review, Aug. 5, 2021, 92 pages.
*Lumenis Ltd.* v. *BTL Healthcare Technologies A.S.*, PTAB-IPR2021-01276, Declaration of Dr. MaromBikson (EX1002), Aug. 5, 2021, 241 pages.
*Lumenis Ltd.* v. *BTL Healthcare Technologies A.S.*, PTAB-IPR2021-01276, U.S. Pat. No. 10,965,575, Petition for Inter Partes Review, Aug. 5, 2021, 79 pages.
*Lumenis Ltd.* v. *BTL Healthcare Technologies A.S.*, PTAB-IPR2021-01278, Declaration of Dr. MaromBikson (EX1002), Aug. 13, 2021, 255 pages.
*Lumenis Ltd.* v. *BTL Healthcare Technologies A.S.*, PTAB-IPR2021-01278, U.S. Pat. No. 10,709,894, Petition for Inter Partes Review, Aug. 13, 2021, 85 pages.
*Lumenis Ltd.* v. *BTL Healthcare Technologies A.S.*, PTAB-IPR2021-01279, Declaration of Dr. MaromBikson (EX1002), Aug. 5, 2021, 258 pages.
*Lumenis Ltd.* v. *BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd.* v. *BTL Healthcare Technologies A.S.*, PTAB-IPR2021-01280, Declaration of Dr. MaromBikson (EX1002), Aug. 13, 2021, 235 pages.
*Lumenis Ltd.* v. *BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd.* v. *BTL Healthcare Technologies A.S.*, PTAB-IPR2021-01282, Declaration of Dr. MaromBikson (EX1002), Aug. 5, 2021, 267 pages.
*Lumenis Ltd.* v. *BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd.* v. *BTL Healthcare Technologies A.S.*, PTAB-IPR2021-01283, Declaration of Dr. MaromBikson (EX1002), Aug. 5, 2021, 241 pages.
*Lumenis Ltd.* v. *BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd.* v. *BTL Healthcare Technologies A.S.*, PTAB-IPR2021-01284, Declaration of Dr. MaromBikson (EX1002), Aug. 5, 2021, 279 pages.
*Lumenis Ltd.* v. *BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd.* v. *BTL Healthcare Technologies A.S.*, PTAB-IPR2021-01285, Declaration of Dr. MaromBikson (EX1002), Aug. 13, 2021, 249 pages.
*Lumenis Ltd.* v. *BTL Healthcare Technologies A.S.*, PTAB-IPR2021-01285, U.S. Pat. No. 10,709,894, Petition for Inter Partes Review, Aug. 13, 2021, 79 pages.
Lutronic Corporation, K213748 510(k) Summary, CoreLevee, 8 pages (Oct. 2022).
Madariaga, V.B., et al., "[Magnetic Stimulation of the Quadriceps: Analysis of 2 Stimulators Used for Diagnostic and Therapeutic Applications]," Archivos De Bronconeumologia, 43(7):411-417, Elsevier Espana, Spain, (Jul. 2007).
Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).
Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).
MAG and MORE Gmbh, Magnetic and Life Science System, Power Mag, 12 Pages.
MAG Expert, 2 pages.
Mag Venture, Magnetic Stimulation, Accessories Catalogue, Accessories Catalogue, 2011, 54 pages.
Hasala, O., et al., Case Study of Treating Acute Ankle Distortion Using TMS, Charles University, Faculty of Physical Education and Sports, Prague, Czech Republic, 4 Pages.
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Heisel, Jurgen, Physikalische Medizin, Stuttgart: Georg Thieme Verlag KG, 2005. ISBN 3-13-139881-7. p. 159.
Hera Estetik Medikal, "Lipostar Manyetik Incelme", accessed at https://www.heraestetik.com/en/urundetay/liposter-manyetik-incelme, accessed on Dec. 15, 2021.
Hera Estetik Medikal, "LIPOSTAR" dated Jul. 7, 2014, accessed at https://www.youtube.com/watch?v=-R7OnFIK9go, accessed on Dec. 15, 2021.
Hill, A., "The Influence of Temperature on the Tension Developed in an Isometric Twitch," Proceeding of the Royal Society B 138:349-354, (Sep. 1951).
Hirvonen, H.E., et al., "Effectiveness of Different Cryotherapies on Pain and Disease Activity in Active Rheumatoid Arthritis. A Randomised Single Blinded Controlled Trial," Clinical and Experimental Rheumatology, 24(3):295-301, Clinical and Experimental Rheumatology S.A.S, Italy (May-Jun. 2006).
Hovey, C. and Jalinous, R., "The Guide to Magnetic Stimulation" Magstim, Pioneers in Nerve Stimulation and Monitoring, pp. 1-44 (2016).
Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
I-Lipo by Chromo genex, i-Lipo Ultra is the Intelligent, Non-Surgical Alternative to Liposuction, 2011, 2 pages.
Increasing Physiotherapy Presence in Cosmetology, Spa Inspirations, Jan. 2012, pp. 34-35.
InMode Ltd., K191855 K10(k) Summary, Em Face Device, 10 pages (Oct. 2019).
InMode Ltd., K210877 K10(k) Summary, Evolve System with the T3 Applicator, 18 pages (Oct. 2023).
InMode Ltd., K231495 K10(k) Summary, The Evolve System with the Transform Applicator, 9 pages (Oct. 2023).
Irazoqui P., Post Grant Review of U.S. Pat. No. 10,695,576, PTAB-PGR2021-00024, filed as EX1085, Dec. 14, 2020, 25 pages.
Iskra Medical, "TESLA Stym—Functional Magnetic Stimulation FMS," Nov. 2013, http://ww.iskramedical.eu/magneto-therapy-medical/tesla-stym, 5 pages.
Iskra Medical, Magneto System, 2012, 2 pages.

(56) References Cited

OTHER PUBLICATIONS

Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).

Jacob, C., et al., "High Intensity Focused Electro-Magnetic Technology (HIFEM) for Non-Invasive Buttock Lifting and Toning of Gluteal Muscles: A Multi-Center Efficacy And Safety Study," Journal of Drugs in Dermatology 17(11):1229-1232, Physicians Continuing Education Corporation, United States (Nov. 2018).

Jacob, C.I., et al., "Safety and Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).

Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used for Abdominal Body Shaping," American Society for Laser Medicine and Surgery, 2018 Electronic Posters (ePosters) Town Hall and ePosters, 369, p. 1, Wiley Periodicals, Inc. (2018).

Jalinous, R., "Technical and Practical Aspects of Magnetic Nerve Stimulation," Journal of Clinical Neurophysiology 8(1):10-25, Lippincott Williams and amp; Wilkins, United States (Jan. 1991).

Jeanrenaud, B., "Lipid components of adipose tissue," Handbook of Physiology, Adipose Tissue, Chapter 15, Published online Jan. 2011, 8 Pages.

Johari Digital Healthcare Ltd., 510(k)—K062439 Powertone Letter from Department of Health and Humane Services Summary, Public Health Service, Jan. 8, 2007, 6 pages.

Johari Digital Healthcare Ltd., "510(k)—K131291 Torc Body Letter from Department of Health and Humane Services", Public Health Service, Jun. 14, 2013, 10 pages.

Johari Digital Healthcare Ltd., K131291 510(k) Summary, TorcBody, All pages (Jun. 2013).

Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).

Katuscakova, Z.L., et al., High Induction Magnet Therapy in Rehabilitation, Department of Physiactric Rehabilitation, 2012, 72 pages.

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams and Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).

Kim, Y.H., et al., "The Effect of Cold Air Application on Intra-Articular and Skin Temperatures in the Knee," Yonsei Medical Journal, 43(5):621-626, Yonsei University, Korea (South) (Oct. 2002).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Korman, P., et al., "Temperature Changes in Rheumatoid Hand Treated With Nitrogen Vapors and Cold Air," Rheumatology International, 32(10):2987-2992, Springer International, Germany (Oct. 2012).

Kotz, Y., "Theory and Practice of Physical Culture," Training of Skeletal Muscle With Method of Electrostimulation, 64-67 (Mar. 1971).

Kotz, Y., "Theory and Practice of Physical Culture," Training of Skeletal Muscle With Method of Electrostimulation, 66-72 (Apr. 1971).

Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Langford, J. and Mccarthy, P.W., "Randomised controlled clinical trial of magnet use in chronic low back pain; a pilot study," Clinical Chiropractic 8(1):13-19, Elsevier (Mar. 2005).

Lanzamiento de BTL Vanquish ME en Argentina, BTL Aesthetics Int., 2018 at 0:33, 0:34; available at: https://www.youtube.com/watch?v=5yb51%20MmN76Q&ab_channel=BTLAestheticsInt, downloaded Jul. 12, 2023; 2 pages.

Lee, P.B., et al., "Efficacy of Pulsed Electromagnetic Therapy for Chronic Lower Back Pain: a Randomized, Double-blind, Placebcontrolled Study," The Journal of International Medical Research 34(2):160-167, Cambridge Medical Publications, England (Mar.-Apr. 2006).

Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).

Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).

Letter from Department of Health and Human Services, Public Health Service, Dec. 19, 2014, 7 pages.

Letter from US Food & Drug Administration to Johari Digital Healthcare Ltd. regarding K212866, attaching 510(K) summary; Dec. 3, 2022; 17 pages.

Kocbach et al., A Simulation Approach to Optimizing Performance of Equipment for Thermostimulation of Muscle Tissue using COMSOL Multiphysics, Biophysics & Bioeng. Letters, 4(2), (2011) (26 pages).

Maximus Non-invasive Body Shaping System User Manual, http://download.lifvation.com/ Maximus_UserManual.pdf, May 2012 (44 pages).

Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.

Notice of Allowance dated Aug. 23, 2021 for U.S. Appl. No. 15/678,915 (pp. 1-5).

Office Action (Notice of Allowance and Fees Due (PTOL-85)) dated Sep. 18, 2023 for U.S. Appl. No. 17/498,610 (pp. 1-7).

Office Action dated Dec. 24, 2020 for U.S. Appl. No. 15/678,915 (pp. 1-6).

(56) References Cited

OTHER PUBLICATIONS

Office Action dated Jul. 10, 2020 for U.S. Appl. No. 15/678,915 (pp. 1-9).
Office Action dated Oct. 7, 2019 for U.S. Appl. No. 15/678,915 (pp. 1-8).
Trifractional FAQs, http://pollogen.lifvation.com/FAQ/TriFractional%20FAQs.pdf, Aug. 2011 (4 pages).
TriLipo MED Procedure, http://download.lifvation.com/Maximus_TriLipoMED_Intro.pdf, Apr. 2013 (66 pages).
Venus Swan, http://www.medicom.cz/UserFiles/File/LekarskeNenue/020Swan%20EN.pdf, Apr. 2016 (2 pages).
Wanitphakdeedecha et al., Treatment of abdominal cellulite and circumference reduction with radiofrequency and dynamic muscle activation, J. Cosmetic and Laser Therapy, 17:5, 246-251 (2015).
2018 Cutera University, Clinical Forum, Cutera 20, 26 pages.
501(k) K030708 Slendertone FLEX Letter from Department of Health and Humane Serivces, Public Health Service, Jun. 25, 2003, 6 pages.
501(k) K163165 AM-100 Letter from Department of Health and Human Services, Public Health Service, Feb. 16, 2017, 9 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Agilent Technologies, Inc., "Agilent 33500 Series 30 MHz Function / Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: (Aug. 3, 2010), 8 pages.
*Allergan, Inc. et al* v. *BTL Healthcare Technologies A. S.*, PTAB-PGR2021-00015, Paper 16 (Decision Denying Institution of Post-Grant Review), Jun. 17, 2021, 20 pages.
*Allergan, Inc. et al* v. *BTL Healthcare Technologies A. S.*, PTAB-PGR2021-00017, Paper 16 (Decision Denying Institution of Post-Grant Review), Jun. 16, 2021, 33 pages.
*Allergan, Inc. et al* v. *BTL Healthcare Technologies A. S.*, PTAB-PGR2021-00018, Paper 16 (Decision Denying Institution of Post-Grant Review), Jun. 16, 2021, 42 pages.
*Allergan, Inc. et al* v. *BTL Healthcare Technologies A. S.*, PTAB-PGR2021-00020, Paper 16 (Decision Denying Institution of Post-Grant Review), Jun. 16, 2021, 35 pages.
*Allergan, Inc. et al* v. *BTL Healthcare Technologies A. S.*, PTAB-PGR2021-00021, Paper 17 (Decision Denying Institution of Post-Grant Review), Jun. 16, 2021, 33 pages.
*Allergan, Inc. et al* v. *BTL Healthcare Technologies A. S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
*Allergan, Inc. et al* v. *BTL Healthcare Technologies A.S.*, PTAB-PGR2021-00016, Paper 16 (Decision Denying Institution of Post-Grant Review), Jun. 17, 2021, 20 pages.
Alma Lasers., "Accent Radiofrequency System, Operator's Manual," Wellbeing Through Technology, 2008, Chapters 1-8, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M and Harry, R.S., "Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Baranov, A., Krion, Whole Body Cryotherapy, Russia, 19 Pages.

Barker, A.T, "An Introduction to the Basic Principles of Magnetic Nerve Stimulation," Journal of Clinical Neurophysiology, 8(1):26-37, Lippincott Williams and Wilkins, United States, (Jan. 1991).
Barker, A.T., "The History and Basic Principles of Magnetic Nerve Stimulation," Electroencephalography and Clinical Neurophysiology 51:3-21, Elsevier, Netherlands (1999).
Barker, A.T., et al., "Non-Invasive Magnetic Stimulation of Human Motor Cortex," Lancet 1(8437):1106-1107, Elsevier, England (May 1985).
Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Basic Protocol of Salus, Talent with Incontinence Chair, REMED, 1 page.
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beijing ADSS Development Co., Ltd., K231318 510(k) Summary, Electromagnetic Stimulator Device (Models: EM Contouring and Tesla Duet), 11 pages (Jul. 2023).
Beilin, G., et al., "Electromagnetic Fields Applied to the Reduction of Abdominal Obesity," Journal of Cosmetic and Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams and Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).
Binder-Macleod, S.A., et al., "Use of a Catchlike Property of Human Skeletal Muscle to Reduce Fatigue," Muscle and Nerve 14(9):850-857, John Wiley and Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," 36 pages (Apr. 2006).
Bio-Medical Research Ltd., K010335, 510(k) Summary, Slendertone Flex, 933 pages (Sep. 2001).
Bio-Medical Research Ltd., K022855 510(k) Summary, Slendertone, 1-6 (Mar. 2003).
Bios s.r.l., K201239 510(k) Summary, NuEra Tight Family, EMS Model, 9 pages (Dec. 2020).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical and Biological Engineering and Computing 28(2):196-198, Springer, United States (Mar. 1990).
*BTL Industries, Inc.* v. *Allergan Ltd. et al* DDE-1-20-cv-01046, Complaint for Patent Infringement and Exhibits 1-38, 821 pages (Aug. 2020).
*BTL Industries, Inc.* v. *Allergan Ltd. et al* DDE-1-20-cv-01046, Order Granting Motion to Stay Pending Resolution of Proceedings at the International Trade Commission (Unopposed), 2 pages (Oct. 2020).

(56) References Cited

OTHER PUBLICATIONS

*BTL Industries, Inc.* v. *Allergan Ltd. et al.,* DDE-1-20-cv-01046, Order Adminstratively Closing Case, Jul. 26, 2021, 1 page.
*BTL Industries, Inc.* v. *Allergan PLC et al* DDE-1-19-cv-02356, Complaint for Patent Infringement and Exhibits 1-34, 375 pages (Dec. 2019).
*BTL Industries, Inc.* v. *Allergan PLC et al* DDE-1-19-cv-02356, Order Granting Stipulation to Stay, Oct. 1, 2020, 1 page.
*BTL Industries, Inc.* v. *Allergan USA, Inc. et al.,* DDE-1-19-CV-02356, Order Administratively Closing Case, Jul. 26, 2021, 1 page.
BTL Industries, Inc., K163165 510(k) Summary, AM-100, All pages (Feb. 2017).
BTL Industries, Inc., K180813 510(k) Summary, Emsculpt, 9 pages (Mar. 2018).
Buenos Aires, Oct. 14, 2014, Venus Concept, Provision No. 7246, 56 pages (With Machine Translation).
Burge, S.M and Dawber, R.P., "Hair Follicle Destruction and Regeneration in Guinea Pig Skin After Cutaneous Freeze Injury," Cryobiology, 27(2):153-163, Elsevier, Netherlands (Apr. 1990).
Pribula, O., et al., "Optical Position Sensor Based on Digital Image Processing: Magnetic Field Mapping Improvement," Radioengineering 20 (1):55-60, (Apr. 2011).
Pribula, O., et al., "Real-Time Video Sequences Matching Spatio-Temporal Fingerprint," IEEE, 911-916 (Jun. 2010).
Prouza, O., "Ex-Post Analyza Spot Rebnich Dani," 58 pages, (2008).
Prouza, O., "Targeted Radiofrequency Therapy for Training Induced Muscle Fatigue—Effective or Not?," International Journal of Physiotherapy 3(6):707-710 (Dec. 2016).
Prouza, O., et al., "High-Intensity Electromagnetic Stimulation Can Reduce Spasticity in Post-Stroke Patients," International Journal of Physiotherapy 5(3):87-91 (2018).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-TALENT-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, Doc No. MK-004 A, 2008, 53 Pages.
Remed Co Ltd K202031 510(k) Summary, Talent-Pro Electromagnetic Stimulator, 11 pages (May 2021).
Reshaping the Future of Your Practice, Cool sculpting, A Revolution in Aesthetic Fat Reduction, 2011, 10 Pages.
Riehl., M., "Chapter 3: TMS Stimulator Design" The Oxford Handbook of Transcranial Stimulation, Wasserman, E.M., ed., pp. 13-23, Oxford University Press, 26 pages, United Kingdom (2008).
Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).
Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams and Wilkins, United States (Apr. 2003).
Russian excerpt of Werner, R., Magnetotherapy, Pulsating energy resonance therapy, 41-67 (Jun. 2007).
Rutkove, S., "Effects of Temperature on Neuromuscular Electrophysiology," Muscle and Nerve 24(7):867-882, John Wiley and Sons, United States (Jul. 2001).
Salus Talent Pop, The first sales bill, Authorization No. 20120221-41000096-66667961, 2 pages, (Feb. 2012).
Salus Talent Pro, Specification, 2 pages.
Salus Talent-A, Remed, User Guide, High Intensity Electro Magnetic Field Therapy, 2017, 37 pages.
Salus Talent-Pop DOUBLE, 2 pages. Dated Nov. 18, 2020.
Salus Talent, a Vertice ad Talos, Drott, 6 pages.
Salus Talent, Deep Penetrating Electro-Magnetic Stimulator, CR Technology, 4 pages.
Salus Talent, Deep Penetrating Electro-Magnetic Stimulator, Rehabilitation Medical Company, New choice, new satisfaction, Talent, 4 pages.
Salus Talent, Electro Magnetic Stimulator, CR Technology, 9 Pages.
Salus-Talent, Device for Deep Electromagnetic Stimulation, Nowosc, Fizjoterapia, 6 Pages.
Salus, Talent Pro, The Birth of Salus Talent Pro inspired by 10 Years of Experience, Specification, Rehabilitation Medical Company, Slimon, 2 pages.
Salus, Talent Pro, The World's 1st Development 3 Tesla, 2Channel Magnetic field Therapy, Slimon , 10 pages.
Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).
Schaefer, D.J., et al., "Review of Patient Safety in Time-Varying Gradient Fields," Journal of Magnetic Resonance Imaging 12:20-29, Wiley-Liss, United States (Jul. 2000).
Shenzhen KeLiTongDa Industrial Co., Ltd., K231136 510(k) Summary, Fitness Belt (Model: KLT-07), 3 pages, (Jun. 2023).
Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).
Silinskas, V., et al., "Effect of Electrical Myostimulation on the Function of Lower Leg Muscles," Journal of strength and Conditioning Research 31(6):1577-1584, Human Kinetics Pub, United States (2017).
Sport-Elec S.A., K061914 510(k) Summary, Sport-Elec, 5 pages (Jul. 2007).
Sport-Elec S.A., K081026 510(k) Summary, Sport-Elec, 5 pages (Nov. 2008).
Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).
Starbelle, PEMF Shape, Webpage, dated Feb. 10, 2020, 3 pages, available at http://www.starbelle.cn/info/PEMFShape.html.
Stedman, T.L., "Aponeurosis—Apparatus," in Stedman's Medical Dictionary, 27th Edition, Pugh, M.B., ed., pp. 113-114, Lippincott Williams and Wilkins, Baltimore, MD (2000).
Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams And Wilkins, United States (Jan. 2004).

(56) References Cited

OTHER PUBLICATIONS

Venus Concept Ltd., K111784 510(k) Summary, Venus Swan System, 5 pages (Oct. 2011).
Venus Concept Ltd., K140629 510(k) Summary, Venus Swan (MP)2 System, 7 pages (Jun. 2014).
Venus Concept Ltd., K143554 510(k) Summary, Venus Legacy CX, 6 pages (Aug. 2015).
Venus Concept Ltd., K182094 510(k) Summary, Family of Venus RF Systems—Heal, 7 pages (May 2018).
Venus Concept Ltd., K191065 510(k) Summary, Venus Viva Device, 12 pages (Apr. 2020).
Venus Concept Ltd., K191528 510(k) Summary, Venus Legacy Pro Device, 9 pages (Sep. 2019).
Venus Concept Ltd., K201164 510(k) Summary, Venus Viva MD Device, 9 pages (Jun. 2020).
Venus Concept Ltd., K211461 510(k) Summary, Family of Venus RF Systems—Venus Freedom, 8 pages (Oct. 2021).
Venus Concept Ltd., K232192 510(k) Summary, Venus Versa Pro System, 11 pages (Sep. 2023).
Venus Concept Ltd., VenusFreeze MP2, User Manual, dated Jun. 2012, 46 pages.
Venus Concept Ltd., VenusViva, User Manual, dated Aug. 2013, 51 pages.
Venus legacy manual, May 24, 2013, 49 pages.
Venus Legacy, 2013, 24 pages.
Venus, Venus legacy marca argentina, Oct. 14, 2014, 20 pages.
VenusFreeze, Experience the Energy, Venus Concept, Delivering the Promise, 2 pages.
Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).
Wada, K., et al., "Design and Implementation of Multi-Frequency Magnetic Field Generator Producing Sinusoidal Current Waveform for Biological Researches," IEEE, 9 pages (2016).
Wanitphakdeedecha, R., et al., "Treatment of Abdominal Cellulite and Circumference Reduction With Radiofrequency and Dynamic Muscle Activation" Journal of Cosmetic and Laser Therapy 17(5):246-251, Informa Healthcare, England (2015).
Ward, A.R. and Shkuratova, N., "Russian Electrical Stimulation: The Early Experiments," Physical therapy 82(10):1019-1030, Oxford University Press, United States (2002).
Wasilewski, M.L., Academy of Aesthetic and Anti-Aging Medicine, Application of magnetic fields with deep stimulation in the fight against local obesity of lower limbs, BTL, 2012, 4 pages.
Web MD, what is normal body temperature? 3 pages, printed Mar. 4, 2019.
Weight to volume aluminum, 2 pages. printed from internet Sep. 25, 2018.
Weight to volume copper, 2 pages printed from internet Sep. 25, 2018.
Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).
Weng, O., "Electromagnetic Activation of the Calf Muscle Pump," UMI Dissertation Publishing (2014). 267 pages.
Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).
Woehrle, J., et al., "Dry Needling and its Use in Health Care—A Treatment Modality and Adjunct for Pain Management," J. Pain & Relief, 4(5): 1-3 (Aug. 2015).
World Health Organization, "Neurological Disorders—Public Health Challenges", pp. 1-115 (2006).
World Health Organization, "The Atlas: Epilepsy Care in the World", pp. 1-96 (2005).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
Z Wave, Instructions for Use, Zimmer Aesthetic Division, Version 5, 44 pages.
ZAO OKB RITM, Electroneurostimulants, Transdermal Scenar-NT Instructions, 24 Pages (Nov. 2013).
ZAO OKB RITM, Percutaneous Electrical Stimulators With Individual Biofeedback Dosing Impact on Reflex Zones, 43 pages (Feb. 2, 2017).
Zelickson, B., et al., "Cryolipolysis for Noninvasive Fat Cell Destruction: Initial Results From a Pig Model," Dermatologic Surgery 35(10):1462-1470, Hagerstown, MD Lippincott, Williams and Wilkins, United States (Oct. 2009).
ZELTIQ System User Manual—Print and Binding Specifications, ZELTIQ Aesthetics, Inc, Mar. 2011, 88 pages.
Zerona R-Z6 by Erchonia, Specifications, Retrieved from the Internet: (www.myzerona.com), 2015, 1 page.
Zerona, Reveal your True Shape, Product Fact Sheet, 3 pages.
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013). 326 pages.
Zhu, Y., et al., "Magnetic Stimulation of Muscle Evokes Cerebral Potentials by Direct Activation of Nerve Afferents: A Study During Muscle Paralysis," Muscle and Nerve 19(12):1570-1575, John Wiley and Sons, United Sates (Dec. 1996).
Zimmer MedizinSysteme GmbH, K192940 510(k) Summary, Cooltone, 14 pages (Nov. 2019).
Zimmer MedizinSysteme GmbH, K203488 510(k) Summary, emField, 9 pages (Feb. 2021).
Zimmer MedizinSysteme GmbH, K220601 510(k) Summary, CoolTone, 11 pages (Apr. 2022).
Notice of Allowance dated Jul. 21, 2021 for U.S. Appl. No. 17/087,850 (pp. 1-8).
Notice of Allowance dated May 6, 2020 for U.S. Appl. No. 16/194,800 (pp. 1-8).
Notice of Allowance dated Oct. 8, 2019 for U.S. Appl. No. 15/603,162 (pp. 1-8).
Notice of Allowance dated Mar. 24, 2021 for U.S. Appl. No. 17/087,850 (pp. 1-8).
Novickij, V., et al., "Compact Microsecond Pulsed Magnetic Field Generator for Application in Bioelectronics," Elektronika ir Elektrotechnika 19(8):25-28 (Oct. 2013).
Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).
Novickij, V., et al., "Magneto-Permeabilization of Viable Cell Membrane Using High Pulsed Magnetic Field," IEEE Transactions on Magnetics 51(9), All pages (Sep. 2015).
Novickij, V., et al., "Programmable Pulsed Magnetic Field System for Biological Applications," IEEE Transactions on Magnetics 50(11):5 (Nov. 2014).
NPF Electroapparat, Amplipulse-5Br Manual, allegedly accessed on Nov. 18, 2020, All pages.
Nuerosoft Ltd., "Neurosoft—Neuro-MS Transcranial Magnetic Simulator Technical Manual," All pages (Nov. 2014).
Obsluze, "Apparatus for High Induction Magnetic Stimulation," 2016, 42 pages.
Obsluze, N.K., Usage Instructions, User's Manual, Device for high-induction magnetic stimulation of type designation: Saluter Moti, 2016, 88 Pages.
Office Action dated Aug. 15, 2019 for U.S. Appl. No. 16/194,800 (pp. 1-12).
Office Action dated Jun. 14, 2021 for U.S. Appl. No. 15/786,303 (pp. 1-13).
Office Action dated Jun. 28, 2021 for U.S. Appl. No. 16/727,458 (pp. 1-11).

(56) References Cited

OTHER PUBLICATIONS

Oliveira, P.DE., et al., "Neuromuscular Fatigue After Low- and Medium-frequency Electrical Stimulation in Healthy Adults," Muscle and Nerve 58(2):293-299, John Wiley and Sons, United States (Aug. 2018).
Operating Manual, MAGSTIM R Air-Cooled Double 70mm Coil System, 1600-23-04, The Magstim Company Limited, 1999, 18 Pages.
Operating Manual, MAGSTIM, Model 200, P/N 3001-01, Double 70mm, Remote Coil, P/N 3190-00, The Magstim Company Limited, 2006, 32 pages.
Operating Manual: Magstim® $200^2$, P/N 3001-23-04, The Magstim Company Limited, Mar. 18, 2005, 34 pages.
Operating Manual: Magstim $D70^2$ Coil, MOP06-EN, Revision 01, The Magstim Company Limited, Feb. 2012, 14 Pages.
Operating Manual: Magstim Magstim $200^2$, MOP01-EN, Revision 01, The Magstim Company Limited, Sep. 2011, 25 Pages.
Operating Manual: Magstim R, 2nd, Generation Coil Family, 3100-23-02, Magstim Coils, The Magstim Company Limited, Nov. 2002, 14 Pages.
Operating Manual: Magstim R, Bistim System, P/N 3234-23-01, The Magstim Company Limited, Nov. 2004, 30 Pages.
Operating Manual: Magstim R, Coils and Accessories, 1623-23-07, Magstim Coils and Accessories, May 2010, 24 Pages.
Operating Manual: Magstim, Magstim Alpha Coil Range, MOP11-EN, Revision 01, Oct. 2012, 18 Pages.
Operating Manual: Magstim, Magstim $Bistim^2$, MOP02-EN, Revision, The Magstim Company Limited, 01, Sep. 2011, 27 Pages.
Operating Manual: MAGSTIM, RAPID2, P/N 3576-23-09, The MAGSTIM Company LTD, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, U.S., et al., "Subcutaneous Adipose Tissue Thickness Alters Cooling Time During Cryotherapy," Archives of Physical Medicine and Rehabilitation, 83(11):1501-1505, W.B. Saunders, United States (Nov. 2002).
Pain Management Technologies, "Pain Management Technologies Product Catalog," (2012). 24 pages.
Papimi, For Scientific Research, Pap Ion Magnetic Inductor, Presentation, Magnetotherapeutic Device, Nov. 2009, 61 Pages.
Pascual-Leone, A., et al., "Handbook of Transcranial Magnetic Stimulation," Chapters 1-4, 58 pages, Arnold Publishers, England (2002).
Periso SA, CTU mega Diamagnetic Pump 20: Device for Diamagnetic Therapy, CTU Mega 20 Manual, dated Aug. 28, 2019, 44 pages, Pazzallo Switzerland.
Photograph, Alleged Photograph of Components of a Salus Talent Pop Double Device with an Aalleged Manufacture date of Nov. 14, 2012, 1 page.
Physiomed, MAG-Expert, Physiomed Manual, Dec. 19, 2012, 63 pages.
Physiomed, Physiomed Mag-Expert, Physiomed Catalog, pp. 81-83. 2020.
Platil, A., "Magnetopneumography Using Optical Position Reference," Sensor Letters 11(1):69-73, ResearchGate (2013).
Podebradsky.K., et al., Clinical study of high-inductive electromagnetic stimulator SALUS talent, 2010, 8 pages.
Pohanka, J., et al., "An Embedded Stereovision System: Aspects of Measurement Precision," 12th Biennial Baltic Electronics Conference, pp. 157-160 (Oct. 2010).
Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.
Polkey M.I., et al., "Functional Magnetic Stimulation of the Abdominal Muscles in Humans," American Journal of Respiratory and Critical Care Medicine 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve 19(5):549-555, John Wiley and Sons, United States, (May 1996).
Pollegen, K200545, Legend Pro DMA, Indications for use, dated Oct. 20, 2021,11 pages.
Pollegen, Trilipo MED Procedure, Brochure, dated Apr. 7, 2021, 76 pages.
Pollegen, Maximus Non-invasive body shaping System, User Manual, dated May 1, 2012, 44 pages, http://download.lifvation.com/Maximus_UserManual.pdf.
Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).
Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).
Pribula, O. and Fischer, J., "Real Time Precise Position Measurement Based on Low-Cost CMOS Image Sensor," IEEE, 5 pages (2011).
Pribula, O., et al., "cost-effective Image Acquisition System for Precise Pc-based Measurements," Przeglad Elektrotechniczny (Electrical Review), 2011, pp. 259-263.
Magneris—ASTAR—Magnetotherapy Unit, 2010 at 1:16, 1:35, 1:40 and 1:50 available at: https://www.youtube.com/watch?v=1o01LYnaq4g&ab_channel=Astar-aparatydlafizjotera, downloaded Jul. 12, 2023; 2 pages.
Magstim Company Limited, K051864 510(k) Summary, Magstim Rapid and Magstim Super Rapid, All pages (Dec. 2005).
Magstim Company US, LLC, K060847 510(k) Summary, Magstim Model 200-2 with Double 70mm Remote Coil, All pages (Sep. 2006).
Magstim Corporation US, K992911 510(k) Summary, Magstim Rapid, 3 pages (Jan. 2000).
MagVenture, MagPro® by MagVenture®, Versatility in Magnetic Stimulation, World Leading Transcranial Magnetic Stimulation Systems, 2011, 6 Pages.
Man, W.D-C., et al., "Magnetic Stimulation for the Measurement of Respiratory and Skeletal Muscle Function," The European Respiratory Journal 24(5):846-60, European Respiratory Society, England (2004).
Manstein, D., et al.,"Selective Cryolysis: A Novel Method of Non-Invasive Fat Removal," Lasers in Surgery and Medicine, 40(9):595-604, Wiley-Liss, United States (Nov. 2008).
Mantis Theramagnetic Compact: the compact that guarantees utmost efficiency and maximum performance, theramagnetic, 2020, 8 pages.
Mantis, The non-invasive solution that restores natural beauty, improves health, and offers a renewed psychophysical sense of balance, MR991 theramagnetic, 2020, 8 pages.
Mantovani, A., et al., "Applications of Transcranial Magnetic Stimulation to Therapy in Pyschiatry," Psychiatric Times 21(9), Intellisphere, 29 pages (Aug. 2004).
Marek Heinfarth, "Lipostar" dated Jan. 9, 2013, accessed at https://www.youtube.com/watch?v=hZurkn8iU_U, accessed on Dec. 15, 2021.
Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).
Moon, Chi-Woong "Study on the Pulsed Electromagnetic Fields Effect of Adipocyte Decomposition" Final Report of a Middle-grade Researcher Support Project, Inje University, 2017. 107 pages.

(56) References Cited

OTHER PUBLICATIONS

Morrissey. M., "Electromyostimulation from a Clinical Perspective," Sports Medicine 6(1):29-41, Springer International, New Zealand (Aug. 1988).

Mulholland, R.S., "Synergistic Multi-polar Radiofrequency and Pulsed Magnetic Fields in the Non-Invasive Treatment of Skin Laxity and Body Contouring," 4 pages.

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).

Nanjing Vishee Medical Technology Co., Ltd., K222875 510(k) Summary, MagGraver F200, 12 pages (Mar. 2023).

Nanjing Vishee Medical Technology Co., Ltd., K230767 510(k) Summary, Pelvic Floor Muscle Stimulator, 7 pages (Sep. 2023).

Nassab, R., "The Evidence Behind Noninvasive Body Contouring Devices," Aesthetic Surgery Journal, 35(3):279-293, Oxford University Press, England (Mar. 2015).

National Institute of Neurological Disorders and Stroke, Epilepsy Information Page, www.ninds.nih.gov/disorders/epilepsy/epilepsy.htm, pp. 1-6 (Feb. 1, 2016).

Neotonus, Inc., K973096 510(k) Summary, Neotonus Model 100 Muscle Stimulator System, (Jun. 1998) 4 pages.

Neotonus, Inc., K973929 510(k) Summary and FDA Correspondence, Neotonus, 5 pages (May 1998).

Neuro Star, TMS Therapy, Bringing Hope to Patients with Depression, 2013, 6 Pages.

Neurosoft, Ivanovo, Since 1992, Magnetic Stimulator, NEUROMS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams and Wilkins, United States (Sep. 1995).

Non Final Office Action mailed Dec. 1, 2016, in U.S. Appl. No. 15/151,012, Schwarz, T., et al., filed May 10, 2016.

Non Final Office Action mailed Dec. 12, 2016, in U.S. Appl. No. 15/099,274, Pribula, O., et al., filed Apr. 14, 2016.

Non Final Office Action mailed Dec. 17, 2015, in U.S. Appl. No. 14/697,934, Zarsky, J., et al., filed Apr. 28, 2015.

Non Final Office Action mailed Feb. 10, 2016, in U.S. Appl. No. 14/873,110, Ladman, J., et al., filed Oct. 1, 2015.

Non Final Office Action mailed Feb. 11, 2016, in U.S. Appl. No. 14/926,365, Prouza, P., et al., filed Oct. 29, 2015.

Non Final Office Action mailed Feb. 25, 2016, in U.S. Appl. No. 14/870,713, Schwarz, T., et al., filed Sep. 30, 2015.

Non Final Office Action mailed Jun. 16, 2016, in U.S. Appl. No. 15/073,318, Schwarz, T., et al., filed Mar. 17, 2016.

Non Final Office Action mailed Jun. 23, 2017, in U.S. Appl. No. 15/473,390, Schwarz, T., et al., filed Mar. 29, 2017.

Non Final Office Action mailed Jun. 27, 2017 in U.S. Appl. No. 15/601,719, Schwarz, T., et al., filed May 22, 2017.

Non Final Office Action mailed Jun. 28, 2017, in U.S. Appl. No. 15/073,318, Schwarz, T., et al., filed Mar. 17, 2016.

Non Final Office Action mailed Jun. 29, 2017, in U.S. Appl. No. 14/789,156, Ladman, J., et al., filed Jul. 1, 2015.

Non Final Office Action mailed Jun. 30, 2017, in U.S. Appl. No. 15/471,946, Schwarz, T., et al., filed Mar. 28, 2017.

Non Final Office Action mailed Mar. 24, 2017, in U.S. Appl. No. 15/396,073, Schwarz, T., et al., filed Dec. 30, 2016.

Non final Office Action mailed Mar. 28, 2017, in U.S. Appl. No. 15/344,811, Schwarz, T., et al., filed Nov. 7, 2016, 11 pages.

Non Final Office Action mailed May 9, 2016, in U.S. Appl. No. 14/789,658, Ladman, J., et al., filed Jul. 1, 2015.

Non Final Office Action mailed May 9, 2016, in U.S. Appl. No. 14/951,093, Schwarz, T., et al., filed Nov. 24, 2015.

Non Final Office Action mailed Nov. 4, 2015, in U.S. Appl. No. 14/700,349, Schwarz T., et al., filed Apr. 30, 2015.

NonFinal Office Action mailed May 4, 2016, in U.S. Appl. No. 14/873,110, Ladman, J., et al., filed Oct. 1, 2015.

\* cited by examiner

TREATMENT DEVICE

CROSS-REFERENCE TO RELATED APPLICATION(S)

This application is a continuation of U.S. patent application Ser. No. 17/498,610, filed Oct. 11, 2021, now pending, which is a continuation of U.S. patent application Ser. No. 15/678,915, filed Aug. 16, 2017, which issued on Oct. 12, 2021 as U.S. Pat. No. 11,141,219, which claims priority to and benefit of U.S. Provisional Application No. 62/375,796 filed Aug. 16, 2016, all of which are incorporated herein by reference in their entireties.

TECHNICAL FIELD

The field of the invention is an apparatus and methods with a high degree of modularity directed to a self-operated device for aesthetic treatment using a combination of one or more treatment applicators that may provide one or more types of treatment energy to the patient's tissue.

BACKGROUND

Human skin is tissue which is commonly treated in order to improve its visual appearance. Skin is composed of three basic elements: the epidermis, the dermis and the hypodermis or so called subcutis. The outer and also thinnest layer of skin is the epidermis. The epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of fat cells. Fat cells create lobules which are bounded by connective tissue, fibrous septa (retinaculum cutis).

Another part of adipose tissue located in the peritoneal cavity is known as abdominal obesity. The visceral fat layer forming visceral white adipose tissue (VWAT) is located between the parietal peritoneum and the visceral peritoneum, closely below muscle fibers adjoining the hypodermis layer.

Excess adipose tissue in the subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been linked to various cardiovascular diseases and diabetes.

Undesirable skin appearance (e.g. topographic skin appearance) may also be caused by changes in the dermal or sub-dermal layer of the skin, especially by excessive quantity or volume of fat cells, weakening of fibrous septas, loss of elasticity, collagen structural or volume changes and/or limited lymph flow, which may result in the accumulation of toxins.

Pigment inhomogeneity caused by structural changes in the epidermis, by pigment granules contraction, expansion, or pigment migration in the skin may also lead to low self-confidence in people with this skin condition.

Current devices for aesthetic use have limited modularity. An operator may have to use two or more different applicators and provide separate treatments one at a time in order to achieve the most desirable results. This is time consuming and expensive and therefore some patients may not be able to afford it. No device and/or method in the current state of art is able to provide large scale of treatment therapies during one treatment session, with a large treatment area and large range of hardware modularity. Current state of art systems are not able to change hardware patterns during one session, cannot connect to another device during treatment and cannot operate without an operator. No device of the current state of art can resist obsolescence like the presented modular device and method of use. Self-operated devices have several benefits e.g.: fast reaction under changing therapy conditions, preventing human mistakes, time saving, saving data from previous treatments and learning from them etc. Multiple therapies also improve the effect and safety of the treatment. Operator guided treatment applicators are not able to simultaneously provide multiple different therapies across the large patient surface. There is a need for apparatus and methods that allow an operator to choose several treatment types that can treat with minimal intervention by the user.

Current state of art apparatuses providing complex treatments are very expensive, which results in high prices for treatment sessions. The price of current state of art apparatuses may be also the reason why a purchaser hesitates when choosing between a cheap lower quality apparatus and an apparatus of high quality, which is very expensive.

One solution for reducing the initial cost of high quality apparatuses may be renting a device adapted to these needs.

SUMMARY

Described herein is a device and method of its use for aesthetic treatment with multiple types of treatment energy that may be delivered into various body parts including e.g.: bra fat area, buttocks, saddlebags, love handles, abdomen, hips, thighs, arms, limb, back, cervical body part, also a muscle or muscle group of the mentioned body parts and/or any other tissue. Treatment energy may be delivered to the tissue of the patient in a sequential and/or simultaneous manner. Different aesthetic skin and/or body treatment effect are provided, e.g.: wrinkle reduction, skin tightening, skin rejuvenation, skin viability, removing of unwanted hair, removing of pigment and/or other skin imperfections (e.g.: atopic eczema, psoriasis, erysipelas, dermatomyositis, lupus, hives, acne, skin veins and/or scars, collagen inhomogeneity, etc.), removing of cellulite, body shaping, muscle stimulation, fat removing, anti-edema and anti-erythema effect, improving blood and lymph circulation, and/or accelerating body metabolism.

In one aspect the device is designed as a mother case with one or more treatment units ensuring control and/or generation of treatment energy, one or more applicators directing the treatment energy into the body and a belt for positioning the applicators into a pattern in proximity to the patient's body. The mother case may be modularly modified by adding and/or removing one or more parts of the device (e.g.: applicators, treatment units) before and/or during the treatment.

Treatment applicators may provide different types of treatment energy e.g.: radio-frequency therapy (RF therapy), plasma therapy, ultra-sound therapy, acoustic wave, shock wave therapy, light (coherent, non-coherent) therapy, heating, cooling, electro-therapy, therapy by generated magnetic field (including muscle stimulation), positive or negative pressure therapy, vibration therapy and/or massage therapy. Treatments may be performed completely without manual operation or even attendance of the operator and/or treatment procedures may by modified during the treatment. One or more treatment applicators may communicate with each other and/or with one or more control units via cables, wireless and/or via a connection through the belt. The communication may provide information about the location and/or type of the applicator, treatment protocol, treatment parameters and other information.

The invention is characterized by a method and modular apparatus with a belt and/or arrangement of applicators enabling multiple treatment procedures and/or therapies at the same time. This improves the effectiveness of the treatment and/or reduces the time needed for the treatment and improves homogeneity and safety. The combination also provides treatments for the same or different tissue structures which may result in synergistic improvement of treatment results.

The belt is designed to fit any type and size of treated patient body area. In one preferred embodiment the belt is created by a supporting matrix with attached applicators in an arbitrary 2D or 3D hardware pattern. The belt is in touch with the patient's body surface and matches the curvature of the patient's body. The belt is designed in order to fit one or more applicators providing at least two different types of treatment energy. The size of the belt may be variable by stretching and/or by plugging and/or removing of one or more parts of the supporting matrix part and/or applicators. The supporting matrix enables placement of the applicator at a working distance at an arbitrary location on the patient's body.

In another embodiment the belt may be considered as a block of at least two treatment applicators attached at an optimal working distance to the patient's body.

The modular apparatus may operate without any manual operation or even without and/or with slight attendance of an operator, which saves time and money. One operator may supervise more than one treated patient. The apparatus may prevent mistakes during treatment caused by human factors. The apparatus may also have a better response to changed treatment conditions and/or may provide more homogenous and precise treatment which improves results and safety of the treatment. With the apparatus controlled by a computer, responses to changed conditions are improved because the apparatus can react on e.g.: movement of the patient or structural changes in the soft tissue, etc.: faster than 0.1 seconds, where human response is at least 0.5 seconds.

The modular apparatus with a belt provides an easy way to change treatment procedures and parameters before and/or during the treatment. The modular system provides various patterns of treatment based on treatment applicators connected to the belt. The modular system may provide to the operator a suggestion of applicator displacement in the belt system based on treatment effect, age, sex and or other parameters. Such modularity enables personalized treatment for each patient.

The present invention solves the problem of device obsolescence due to large scale modularity. The device and method enable hardware and/or treatment pattern changes. The belt may or may not contain a supporting matrix. The belt may be flexible, whole or partly elastic and may be adapted to a patient surface of arbitrary size and shape. This characteristic helps to provide optimal energy transfer from an applicator to the patient soft tissue. Improved contact with the patient skin or surface may decrease or prevent an edge effect, backscattering of delivered energy and/or provides better conditions for collecting feedback information. The supporting matrix may also be connected to upper side of the applicator, may keep one or more applicators in touch with the patient surface, and may not be in touch with the patient.

In another embodiment the device may comprise several treatment units. Each treatment unit ensures control and/or generation of treatment energy for at least one treatment applicator. The separation of treatment units decreases the price of the device and a customer may add (purchase or rent) additional treatment units according to his needs and improve the functionality of the device. In an alternative embodiment the treatment units may be plugged into a mother case. Modularity may also protect the presented device against obsolescence.

One treatment unit may be specialized for providing particular treatment energies and particular treatment effects. In order to achieve the necessary scale of treatment effects another treatment unit may be specialized for providing different treatment energies and different treatment effects. The treatment units may include different components and/or different technological level of components which may allow only the therapies the operator needs.

In one embodiment the device may contain a master unit and one or more therapy generators.

In still another embodiment one or more of the applicators may include its own control unit which may cooperate with one or more control units of the respective treatment unit and/or with a central control unit. The device also may include billing and rental systems for renting of the device, treatment units and/or applicators and billing the user by the treatment procedure or length of rental. A customer may improve its use of the device by renting only the modules necessary for his needs, allowing for reductions in cost, improving accessibility to doctors and clinics.

In another embodiment the presented method and device may include emulator software and/or hardware parts that allow interconnecting arbitrary external devices, treatment units, or applicators in order to communicate and participate in the treatment pattern.

The device may include a communication system that enables communication between external devices e.g. PC, laptop, mobile and others.

According to one embodiment the belt may be wearable and the mother case with treatment unit/s may be part of the wearable belt.

GLOSSARY

Tissue includes skin, muscles, fat, fibrous tissue, nervous tissue (e.g. neurons, motor neuron, and neuromuscular junction), connective tissue, bone tissue and other human or animal tissue.

A patient is a biological material, mainly a human or an animal body.

DETAILED DESCRIPTION

Figure 1:
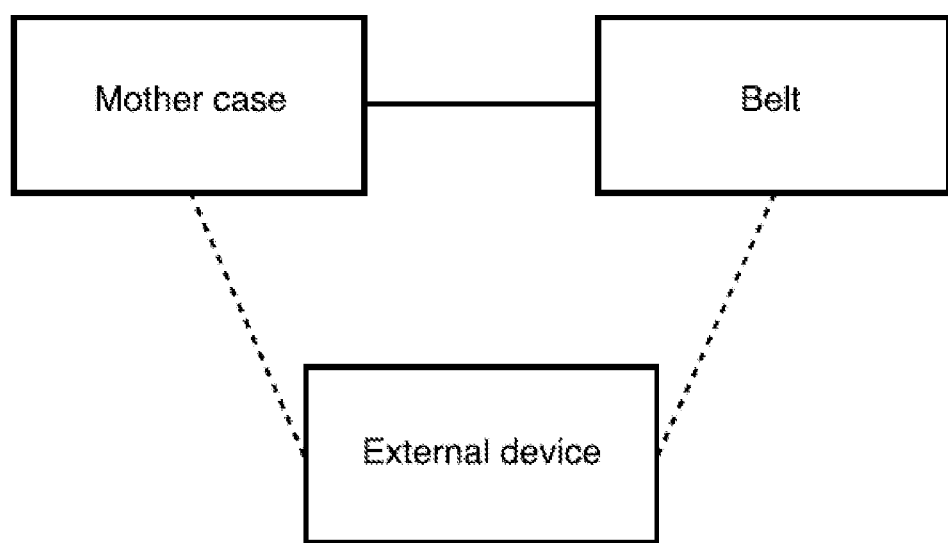
FIG. 1 is schematic diagram representing main segments of the device and communication between them.

FIG. 1 is a schematic diagram representing main segments of the device and communication between them. The device is designed as a mother case with one or more treatment units ensuring control and/or generation of treatment energy, and a belt with one or more applicators directing the treatment energy into the body. The belt displaces the applicators into the pattern in proximity of the patient's body. The mother case may be alternatively connected with an external device connected with the belt by its own separate applicator. According to another embodiment the mother case may be substituted by one or more treatment units and/or external device(s).

Figure 2:
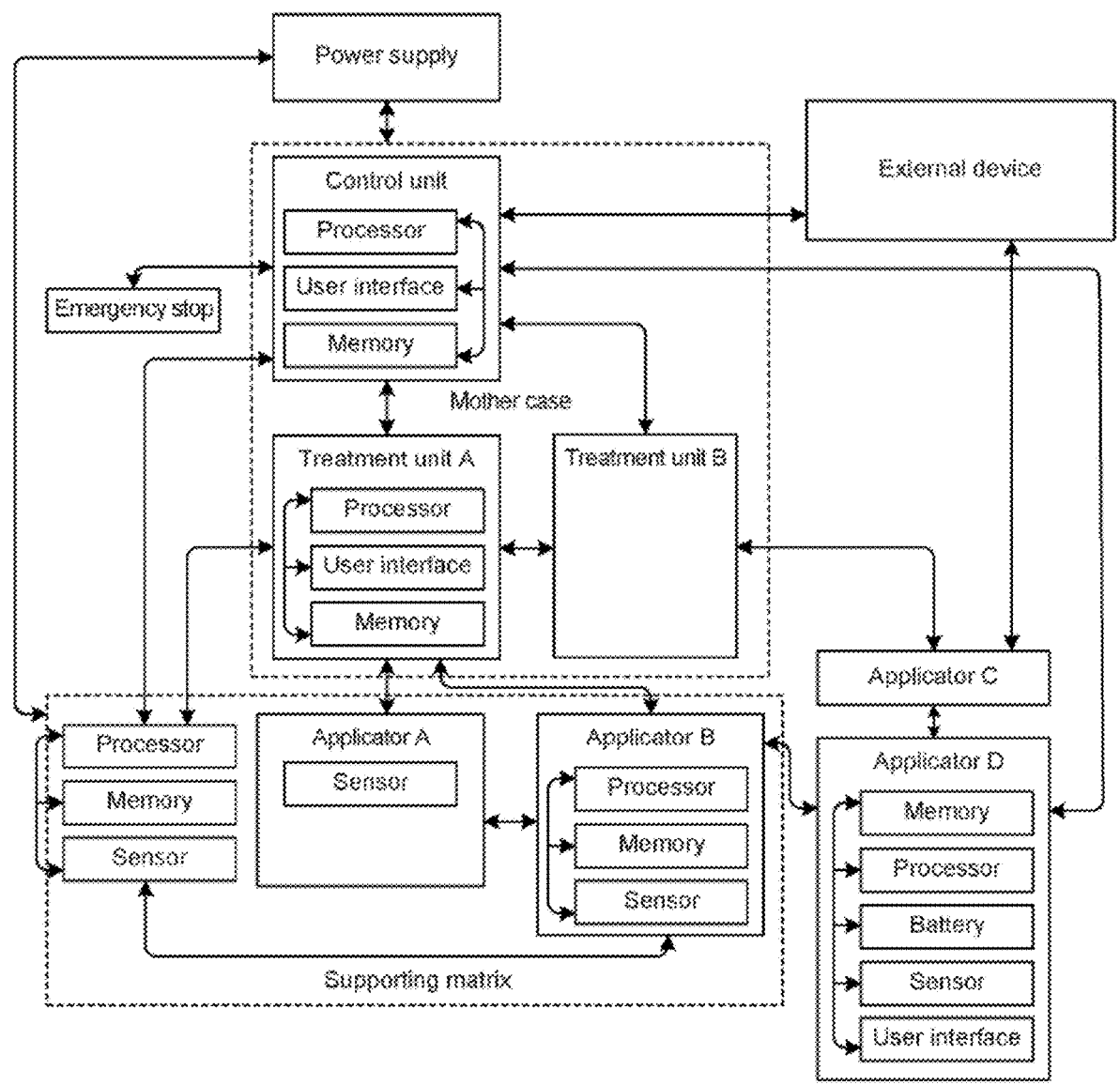
FIG. 2 is a schematic diagram of one possible embodiment of the device and communication between its individual parts.

FIG. 2 is a schematic diagram of one possible embodiment of the device and communication between its individual parts. The device is powered by a power supply. The power supply may be electricity from an external source e.g. electrical power grid; and/or from batteries included in any part of the device. Part of the device such as: a mother case, a control unit, a belt (e.g. supporting matrix), one or more treatment units, one or more external devices and/or one or more applicators may include a direct connection with the power supply and/or may include batteries. Any part of the device may be powered through a connection between other part(s) of the device. For example, the applicator may be powered by the treatment unit, by the supporting matrix, by the mother case and/or by another part of the device. Also one or more treatment units may be powered e.g. by the mother case, external device, supporting matrix and/or directly by connection to the power grid.

According to one of possible embodiment illustrated in FIG. 2, A supporting matrix may be powered by the power supply and then be used as power supply for several applicator(s) attached to the supporting matrix.

The mother case described in detail later in this document may include the control unit and/or one or more treatment units which may have different specifications. Treatment units and applicators may be specialized to provide specific type(s) of treatment therapies by one or more treatment energies and/or may cause one or more treatment effect(s). The control unit may process treatment parameters, protocols and/or other information based on binary code.

The treatment unit may include hardware and/or software components that may modify incoming electric signals and/or communication signals to the treatment unit. Such modified electric signals and/or communication signals may be provided into the applicator(s), supporting matrix, external device and/or another part of the device in order to provide treatment energy from one or more specific treatment energy sources. The applicator(s) may also modify the delivered electrical signal and/or process communication information.

As illustrated in the FIG. 2, some parts of the device e.g. treatment unit B, may not include a processor, a memory, a sensor, a battery, a user interface and/or other feature. The missing features may be substituted by other parts of the device including such features.

As illustrated in the FIG. 2, the device may include a processor and may process information individually and/or in cooperation with other parts including the processor. In one embodiment any processor may receive stored information from any memory of one or more parts of the device.

The belt may be designed as a supporting matrix with attached applicators at an optimal working distance from the patient's body. The optimal working distance may be different for different types of the applicators and/or different treatment energy sources. For example, the optimal working distance for a muscle stimulating electrode may be direct contact with the patient's surface. On the other hand, the optimal working distance for an RF electrode for heating of a patient's adipose tissue may be several millimeters. The optimal working distance of the applicator(s) and/or treatment energy source(s) may be set by the design of the applicator(s), a supporting matrix, a spacing object and/or a fastening member. The applicator(s) may be in contact with patient's surface and/or in proximity to patient's surface and separated from the patient's surface by any material and/or air gap.

According to another embodiment, the belt may consist of a hardware pattern of treatment energy sources where at least two of the energy sources provide different types of treatment energy. The hardware pattern of treatment energy sources may be predefined from the factory and/or, according to another embodiment, may be rearranged according to individual needs of the patient. The belt, according to said embodiment, may be wearable during the day, wherein the mother case (e.g frame with GUI) with treatment unit(s) may be incorporated inside the wearable belt. According to said embodiment, the patient may choose one of several predefined treatment protocols from a list of treatment protocols. Protocols may be based on one or more desired treatment effect(s), treated body part(s), the hardware pattern of the belt and/or other features. The belt according to such an embodiment may be remote controlled, by the patient and/or by any other educated competent user. The belt, according to said embodiment, may be wireless and may be powered by batteries. According to still the same embodiment the belt may be in wireless communication with an external device.

The support matrix may include a processor, memory and/or a sensor for monitoring and/or evaluating at least one treatment parameter and/or may send feedback information to any connected part of the device e.g.: the control unit, the treatment unit(s), the external device(s) and/or the applicator(s). Some of the applicators may not be attached to the supporting matrix but may communicate with the supporting matrix. Applicators may also communicate between each other.

Any part of the device may include a manual and/or a virtual emergency stop button. The emergency stop button may immediately stop any and/or all delivery of treatment energies to the patient's body.

Figure 3:
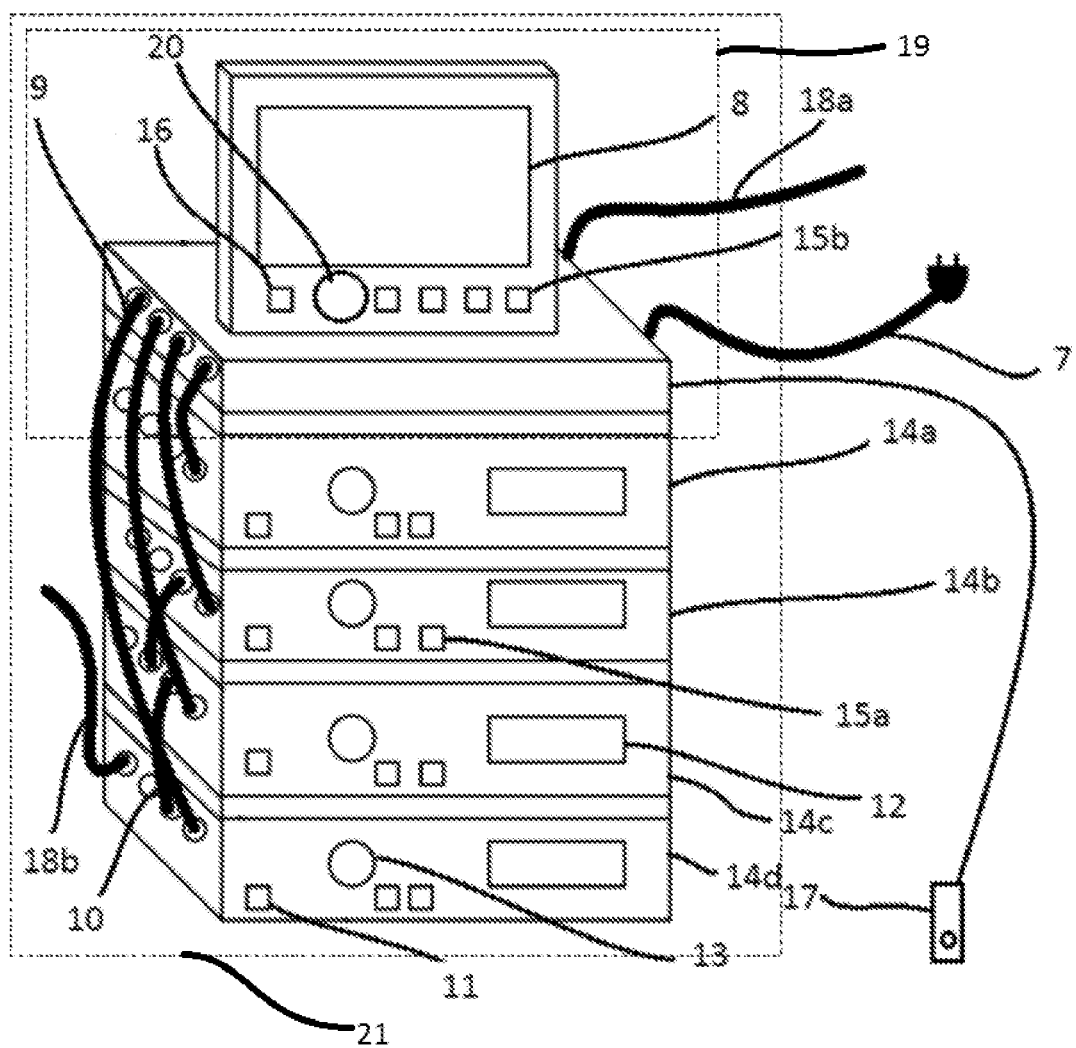
FIG. 3 illustrates a mother case with a control unit and multiple treatment units.

FIG. 3 depicts a mother case with a control unit and multiple treatment units. The mother case may include the control unit 19 of the mother case 21 and one or more treatment units (14a-14d) that may be added according to treatment needs. Individual treatment units (14a-14d) may be designed to provide one or more specific treatment effects and/or one or more treatment energies e.g. RF waves, an electrical current, a magnetic field, acoustic waves, a shock wave, ultrasound waves, light waves, applied lower/higher pressure, friction, plasma, heating, cooling and/or any other treatment energy. The control unit 19 may include a user interface in the form of a touch display 8, several buttons 15a, 15b, a circular control element 20, and a switch button 16. Also, each of the individual treatment units (14a-14d) may include its own user interface that may communicate with an external device, between other treatment units and/or with the control unit 19. The control unit 19 may include the processor and the memory in order to guide the treatment process, store information about treatment including feedback information consumption of individual parts of the device and/or may also include a billing system. The mother case 21, the control unit 19, the treatment units (14a-14d), and the external device or server may also include a black box (e.g. memory) for storing data of the treatment history, communication between individual parts of the device, data for a billing system and/or may store many other types of data.

The mother case 21 may include slots for the treatment units (14a-14d). The treatment unit may be fixed in the right position by a specific type of fastening mechanism that is described below. A fastening mechanism used to fix and/or connect treatment units (14a-14d) to the mother case 21 may by different for different types of treatment units (14a-14d) and/or may be universal for all of the treatment units (14a-14d)

Recognition of the treatment unit may be through the specific impedance of the connected part, an RFID tag, pins, a sequence of specific electrical and/or electromagnetic pulses, measuring of a magnetic field in/near the connection that may be specific for the individual type of the treatment unit, software recognition, a specific binary ID, by recognition of a connected optical signal from the treatment unit and/or through any other of one or more mechanisms. The described system for recognition of the treatment unit may also be used for recognition of individual applicator(s) and/or external device(s). Connection/communication between the mother case, treatment unit(s), the control unit, applicator(s), the supporting matrix and/or external device(s) may be performed wirelessly, by cable 9, by contact pins, by one or more magnets, by one or more conductive parts and/or by a chassis.

The treatment units (14a-14d) may guide treatment provided by one or more applicators independently of the control unit 19 or in cooperation with control unit 19. Some of the treatment units (14a-14d) may not include a processor, memory and/or a user interface and may be just means of connecting to one or more applicators and their management. The treatment units (14a-14d) may be also interconnected. The treatment units may be interconnected between each other.

The respective treatment units may be connected and fixed in the correct slot position of the mother case in a plug and play regime. The treatment unit may include an energy socket or pin connectors to be plugged into the mother case. At least one connector may ensure the energy charge, data communication and/or fluid communication (e.g. in case of cooling, or use of plasma) with the mother case. Alternatively, the data communication between mother case and treatment unit may be performed wirelessly, by cable, or one or more magnets. Recognition of the treatment unit may be through specific impedance, an RFID tag, pins, a sequence of specific electrical and/or electromagnetic pulses, measuring of a magnetic field that may be specific for the individual type of the treatment unit, software recognition and/or through any other of one or more mechanisms. The treatment unit may further include at least one socket/pin for the applicator. The treatment units and also the slots for the treatment units in the mother case may include electromagnetic shielding, vibration shielding, thermal shielding and electrical insulation. The plug and play modular device for individual connection of treatment units provides a large scale of modularity which decreases the cost for the device, requires less space for the device and increases versatility in order to fit all users.

Applicators directing the treatment energy into the body may be connected and/or communicate between each other, with the supporting matrix, with one or more treatment units, with the control unit 19 and/or with an external device. The applicator may include one or more of: treatment energy sources, processors, sensors and/or memory.

The external device may be used to provide and/or control at least part of the treatment. The external device may guide and/or communicate with at least one of: an applicator, a treatment unit and/or the control unit. The external device may be any treatment device able to provide a treatment energy source. The external device may be also be a device (e.g. computer, tablet, smartphone) that is not able to provide a treatment energy source but communicates with the device and is able to monitor treatment and/or adjust treatment parameters.

Communication between individual parts of the device may be based on peer-to-peer and/or master-slave communication. During peer-to-peer communication the individual parts of the device have the same priority of commands and communicate directly between each other. Peer-to-peer communication may be used during initial recognition of connected individual parts of the device. Peer-to-peer communication may be also used between some parts of the device during a treatment. Before and/or during each treatment master-slave communication is used at least for a short time.

During master-slave communication, one part of the device provides commands with highest priority. The part of the device that provides commands with the highest priority at that time is called the master unit.

According to one embodiment, a master unit may be determined by choice of a user before and/or during the treatment. The user may determine the master unit e.g.: the control unit, one of the treatment unit(s) or one or more external device(s) (e.g. laptop, tablet).

According to another embodiment the master unit may be determined automatically based on the predetermined priority value of connected parts of the device. For example, a treatment unit A may be the master unit but after connection of a treatment unit B or an external device to the mother case, the treatment unit B or the external device become the master unit.

At least two parts of the device and/or features may communicate with each other and/or with an external device by optical cable, conductive cable, by other conductive connection and/or wirelessly. Wireless communication may be provided by internet network, local network, RF waves, acoustic waves, optical waves, 3G, 4G, LTE networks, Bluetooth and/or any other.

FIG. 4-7 illustrates several possible master-slave communication schemes. According to the schemas in FIG. 4-7 a therapy generator generates a modified electrical signal in order to provide it to the treatment energy source and provide a treatment effect. Therapy generators may be e.g. a treatment unit, or one or more applicator(s).

The master unit according to the previous definition includes a processor and provides commands with highest priority.

Boxes labelled "Security" according to FIG. 4-7 may symbolize coding of the information used in communication and/or antivirus protection to prevent intrusion of unwanted binary code into the device and/or its communications. The security may also correct mistakes created during communications. The security may also the block connection of an unauthorized/unwanted external device to the device. According to FIG. 4 the security may be located in the communication diagram between the master unit and the communication interface. The security may also be part of a user, a service and/or a sale. According to another possible embodiment the security may be located also between the communication interface and a communication medium, between the master unit and a therapy generator and/or may be part of them.

The communication interface may include hardware and/or software. The communication interface allows transfer of communication signals between at least two different parts of the device or between one part of the device and the communication medium. The communication interface may translate the communication signal into readable form for both of the communicating sides. The communication interface may be e.g. a modem providing communication between the device and online network or server. According to some embodiments, the communication interface may be part of the master unit, the therapy generator, and/or other parts/features of the device.

The communication medium may be a medium for transferring communication data. The communication medium may be used in communication between the device and the user, the service and/or the sale. The communication medium may be e.g. wire, any conductive connection, server, some kind of network based on the principles of e.g.: RF waves, acoustic waves, optic waves, GSM, 3G, 4G, HUB switch, Bluetooth, Wi-Fi which may include one or more servers.

Communication data/information may be redirected to individual parts of the device and/or to individual end users like e.g. the user, the service and/or the sale; by the master unit, the communication medium, the therapy generator and/or individual end user(s). For example a server may filter select data for the user and filter other communication information that will be redirected to e.g. the server, control unit and/or other parts of the device.

Figure 4:
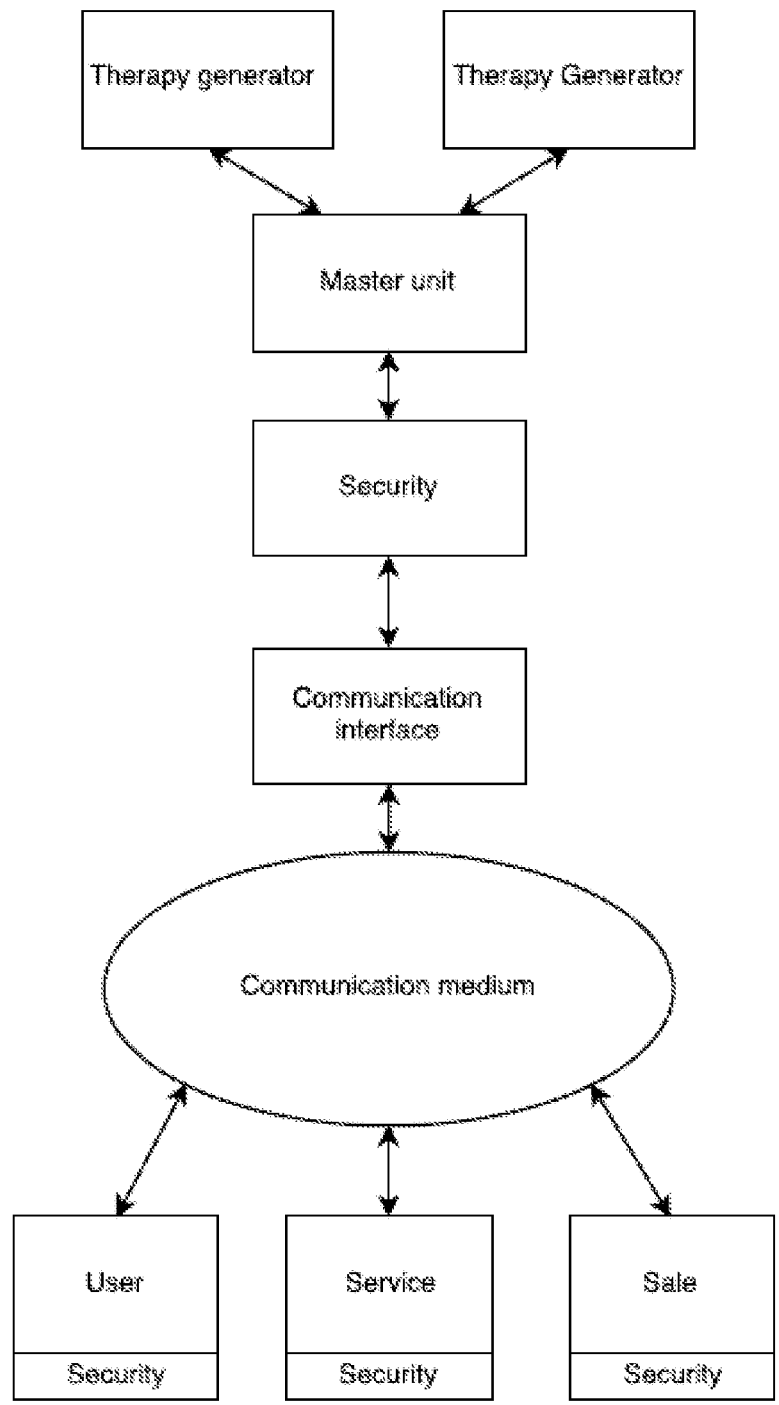
FIG. 4 is a schematic illustration of one possible communication between parts of the device and also external devices with remote access.
Figure 5:
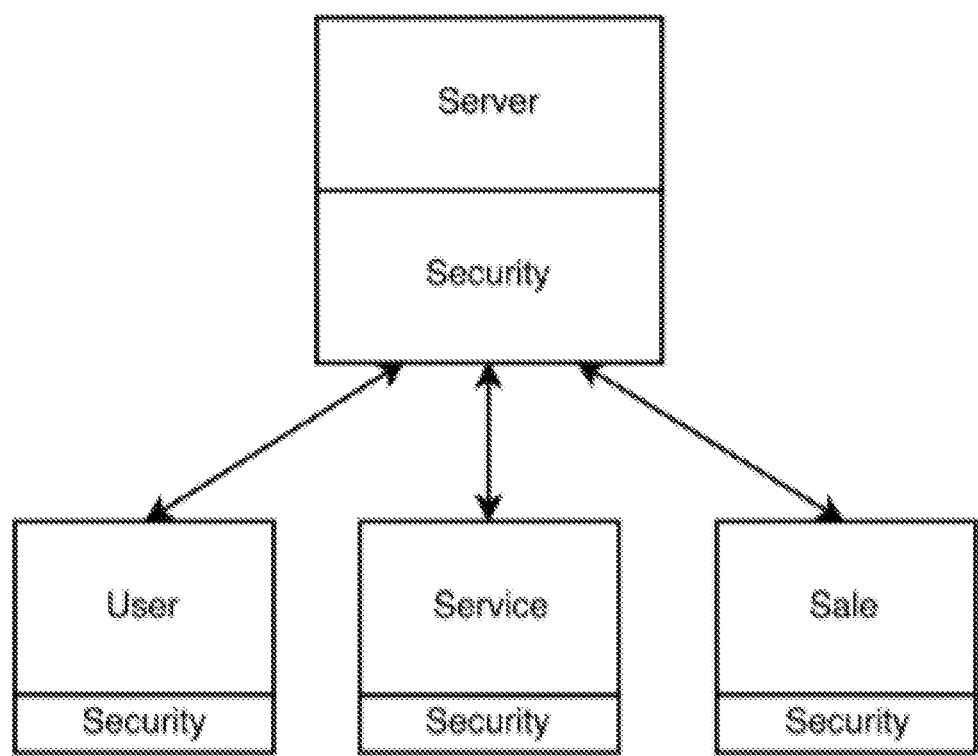
FIG. 5 is a schematic illustration of one possible communication diagram between server and part of the device.

According to FIG. 4-5, the box labelled "User" represents a user's communication device (laptop, mobile, tablet, etc.) that may send information to the device and/or receive information from the device. Information provided by this communication channel may be e.g. the type of treatment protocol, the treatment effect, treatment parameters, feedback information, the schedule of treatments, recommendations of behavior before and after the treatment and/or any other. Some of the user's information may be sent to the operator and some to the patient e.g. by an app device for mobile, tablet or laptop.

The app for a patient may be downloaded to any external device e.g. smartphone, tablet, computer and/or other. The app may communicate with the device and according to the protocol defined by user and/or provider of the device, the patient may display some of treatment protocol information e.g. progress of the treatment, the treated body part, the remaining time of the treatment, heart rate, temperature of the patient's body, provided type(s) of treatment energy, the desired treatment effect, and a comparison of patient's body parameters against previous treatment (like body fat percentage). The app for the patient(s) may inform about the schedule of treatments, recommendations of behavior before and after the treatment e.g. a drinking regimen, proposed exercises and their frequency and/or other.

According to FIG. 4 the box labelled "Service" represents a service department's communication device (laptop, mobile, tablet, etc.) that has authorized access to information about the device. The service department may be e.g. a service department of the device provider company. Information provided by this communication channel may be wear of the device and/or consumption of the device and its components, possible software optimization/actualization of the device, errors in the device, apps for connection of other external devices and/or other.

According to FIG. 4 the box labelled "Sale" represents a sales department's communication device (laptop, mobile, tablet, etc.) with authorized access to information about the device. Exchanged information may be e.g.: number of, time of and/or type of applied treatment. The sale department may send information about e.g.: the renting price of the device, billing for the treatment (described later as a billing system), special offers, the possibility of extending parts of the device, apps for the patients personal smart phones and/or other.

The device may also include a black box storing data of the treatment history, communications between individual parts of the device, and data for a billing system. The data may be accessible to the sale or to the service via the communication medium (e.g. a storage cloud and/or server). The system may manage charges for using the device or respective modules of treatment units and provide this information to the provider in order to prepare the invoice for renting.

The data from the black box may be downloaded only by a verified authorized person e.g. service technician, accountant. Verification of the authorized person may be e.g.: by a specific key, by a password, by a software code of several bits and/or by a specific interconnecting cable.

According to another embodiment the billing system may be based on credit subtracting from the user account. A user's credit may be predefined by the provider of the device e.g. the producer of the device; and/or may be recharged during the time of use. Credits may be subtracted according to the chosen treatment protocol. The credit value for treatment selected by the user may be displayed to the user before treatment starts, during the treatment and/or after the treatment. If the credits in the user account run out the device may not enable any further treatment until credit is recharged. As it is illustrated on the FIG. 4 communication between individual boxes may be bidirectional. According to FIG. 4 secured access of User, Service, and/or Sale may be used to input and/or receive information. Such information may be transferred and/or may be also processed through a Communication medium (e.g. in the server) and/or communication interface and/or master unit where each piece of information is sorted and a decision is made as to where it should be transferred or stored.

The connection between the User, Service, Sale and Communication medium and/or connection between the Therapy generator and Master unit may be secured by Security to provide safe communication and eliminate errors. Security may be also implemented between the Master unit and the Communication interface and/or between the Communication medium and the Communication interface.

Another possible communication between the User, the Service and/or the Sale to the device may be provided by a server (communication medium) illustrated in FIG. 5. The server may have implemented security. The security may or may not be also implemented upon individual access of the User, Service and/or Sale.

Figure 6:
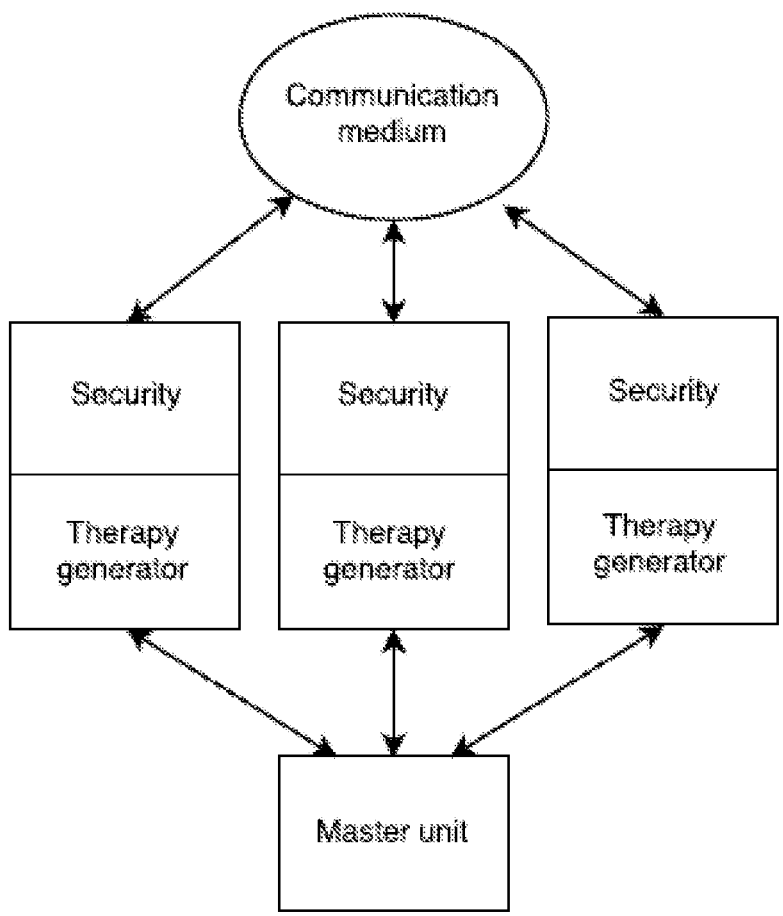
FIG. 6 illustrates communication between a communication medium, therapy generator and master unit.
Figure 7:
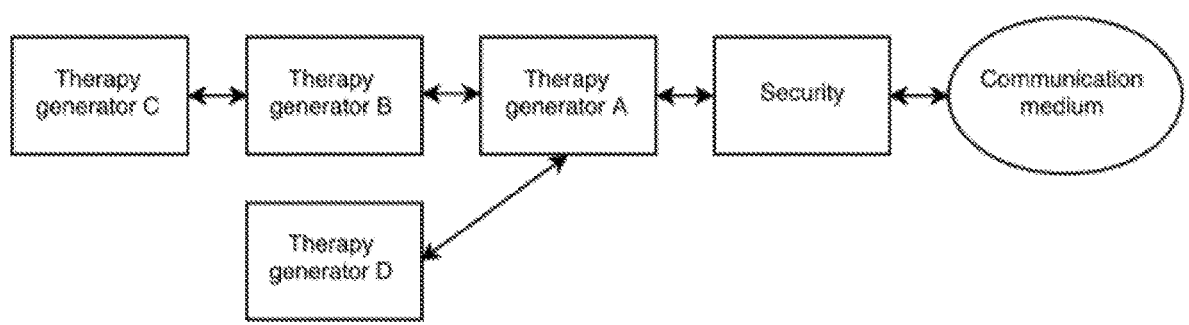
FIG. 7 is schematic diagram of serial communication between a communication medium and a therapy generator.

According to another embodiment depicted in FIG. 6 the communication medium may communicate with Therapy generator(s) and Therapy generator(s) may communicate with the Master unit. According to said embodiment communication information from the communication medium may be verified by the security before the therapy generator sends communication information to the master unit. FIG. 7 is schematic diagram of serial communication between a communication medium and therapy generators. The therapy generator A may communicate with at least one more therapy generator. Subsequent therapy generator B may also communicate with one or more therapy generator(s) e.g. a therapy generator C that does not directly communicate with the therapy generator A.

The device includes one or more applicators for directing the treatment energy into the body and a belt for positioning the applicators into a hardware pattern in proximity to the patient's body. Each applicator may provide one or more different type of treatment energy and/or treatment effect mentioned above and may also include a mechanism for cooling and/or heating of the patient surface and/or any part of the device. For example any applicator may cool itself and/or also part of the supporting matrix. Heating and/or cooling of the patient surface may create thermal gradient across the tissue. Controlled cooling and/or heating may create a volume with the highest/lowest temperature on the surface of the patient or may create a volume with the highest/lowest temperature located under the surface of the patient.

The applicator may include one or more sensors providing feedback information processed by processor and/or external device.

The applicators may have different sizes and shapes. Some of the applicators may have several square millimeters of active surface. The active surface is the side of the applicator oriented to the patient's surface and it is the part of the applicator which directs the treatment energy into the patient's body. The active surface of the applicator may be more than 10, 40, 50, 100, 200, 300, 500 square centimeters.

Applicators may have different shapes. Some of them may have an active surface with a symmetrical shape (e.g.: square, circular, elliptical, triangular, teardrop, rectangular, spidery and/or other types) and some of them may have an asymmetrical shape of the active surface.

The curvature of the active surface of the applicator may be different than the curvature of other parts of the applicator. The active surface of the applicator may have a regular curvature (e.g.: convex, concave, flat, partially elliptical etc.) and/or irregular curvature (e.g.: partly spherical, pointy, wavy, with some ridges etc.). The curvature of the active surface may also be a composition of several different curvatures. The active surface of the applicator may have at some area of active surface a different curvature than the curvature at another specific area of the same applicator. The curvature may create a specific shape on the active surface of the applicator. Some types of applicator's curvature may improve contact with the patient surface, may modify the provided treatment energy delivered to the patient, may increase the treatment comfort, may increase treatment efficiency e.g. (a design providing massage of the patient's surface) and/or may improve collecting of feedback information (e.g. a protruding sensor). The curvature of the active surface may also set the working distance of the applicator and/or may enable air (and/or liquid) to flow under the applicator. In some embodiments the applicator curvature across its active surface may be changeable during the time and/or a curvature may be used in order to provide massage of the patient.

Massage of the patient's soft tissue may be also provided by e.g.: a suction mechanism that creates different air pressure above the patient skin, by mechanical pressure of at least one massage element, massage by switching between parts of the device that creates mechanical pressure, massage by stimulation of neuromuscular plaque and/or muscle fibers, and massage by acoustic waves and/or ultrasound waves. In order to provide a patient's massage and/or other treatment effect the design of the applicator's active surface may be adapted to the specific treatment energy source.

According to a preferred treatment pattern massage may be provided in order to stimulate lymph and/or blood flow in the direction toward the lymph node and/or in the direction toward the heart.

A massage element is a part of the device that creates mechanical pressure on the patient's surface e.g. a protrusion on the applicator's active surface that may be movable.

The active surface of the applicator may be designed from material that is able to adapt to any curvature of the body (e.g.: memory foam, an elastic active surface of the applicator, and/or any other material).

The active surface of the applicator may be modified. Such modification of applicator's active surface may be provided by interchangeable attachments and/or by different exchangeable types of spacing objects located between patient's body and applicator's active. Modification of the applicator's active surface may be provided before, during and/or after treatment. A spacing object may be also part of the supporting matrix.

The active surface of the applicator may also contain one or more apertures of different sizes and shapes. The size and shape of one or more apertures may by variable during the time of the treatment. The apertures may be used to e.g.: provide air and/or liquid flow, may cool/heat patient's surface, and/or supply active substances as it is described in U.S. Provisional Application No. 62/331,060 incorporated herein by reference.

Also, the sizes and shapes of individual treatment energy sources may be variable e.g. RF electrodes as a source of RF treatment energy may have a variable surface as it is described in U.S. patent application Ser. No. 15/584,747 incorporated herein by reference.

One or more electrodes may have different sizes and shapes that influence the size of the treated area, the focus of the treatment, parameters of provided treatment energy and/or homogeneity of the treatment. Electrodes may be formed by conductive wire or a system of wires, by a conductive plate and/or other conductive or semi-conductive object. Shapes of electrodes may be asymmetrical or at least partially symmetrical e.g.: oval, elliptical, planar, square, wavy, convex, concave, spiral and/or other shape of electrode and/or shape of electrode surface. The electrode may consist of one or more pieces. An electrode with rounded edge(s) may minimize edge effects and prevent creation of hot spots. According to a preferred embodiment an RF electrode has a circular contour in a longitudinal cross section and at least partly elliptical shape of a lower part of the electrode 402a in vertical cross section, as shown in FIG. 16.

Figure 16:
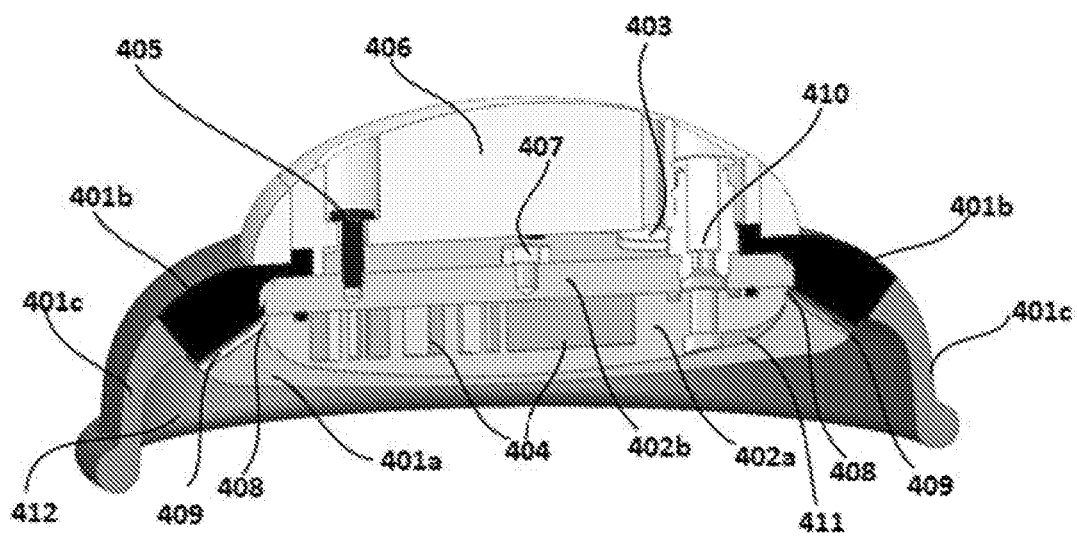
FIG. 16 illustrates an applicator embodiment.

A diameter of the RF electrode in FIG. 16 may be in the range from 0.6 cm to 40 cm or from 6 cm to 30 cm or from 6 cm to 15 cm or may have any other diameter.

The RF electrode of the device may have different sizes and shapes. A surface size of the RF electrode contacting the patient (see lower part of the electrode 402a in FIG. 16) may be in a range between 1 $cm^2$ to 1200 $cm^2$ or between 10 $cm^2$ to 800 $cm^2$ or between 30 $cm^2$ to 300 $cm^2$ or 30 $cm^2$ to 100 $cm^2$.

Figure 11:
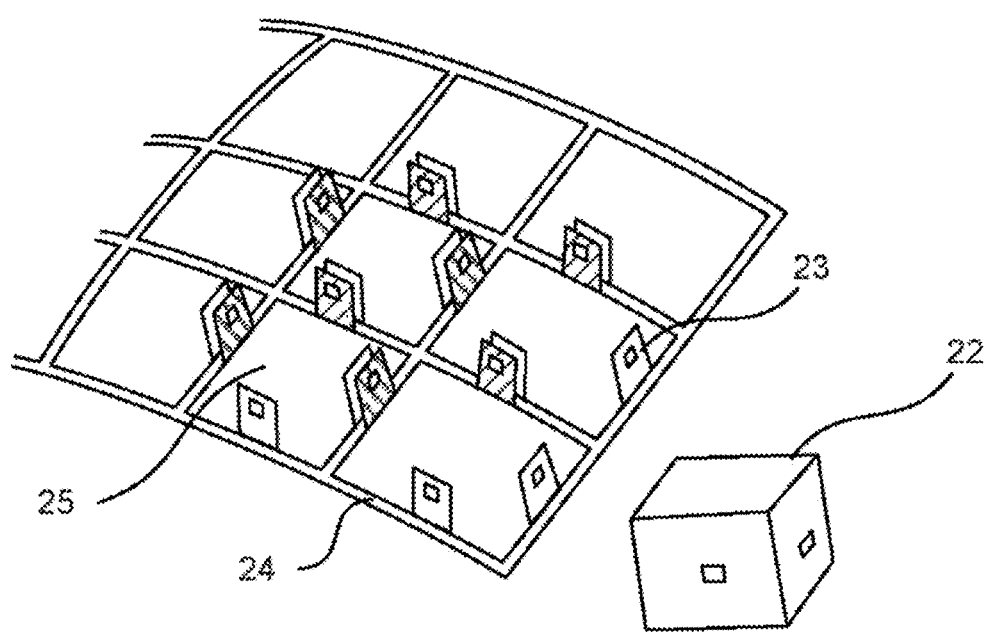
FIG. 11 illustrates one example of a supporting matrix and one applicator.

FIG. 11 illustrates one example of a supporting matrix and one applicator. The applicator 22 may have different sizes and shapes and may be attached by fastening member 23 to the supporting matrix 24 across one or more applicator spots 25. As a result, so-called plug and play methods may be used to modify the hardware pattern of the applicators attached to the patient and/or to the supporting matrix (sorting and/or choosing of the applicators). This plug and play method provides a large scale of modularity. The supporting matrix and/or any processor may recognize which applicator is positioned or fixed in which slot in the supporting matrix. Feedback sensor(s) and/or the user may also determine which body part is going to be treated.

In an exemplary embodiment the applicator, after connection to the supporting matrix, is identified by the master unit and the master unit is capable of recognizing applicator parameters including at least one of: the kind of treatment energy source(s) in the applicator, parameters adjustable for treatment, wear of the applicator, wear of components in the applicator, and the location of the applicator in the support matrix.

According to some embodiments the applicator's spot size and/or shape may be adjusted according the applicator design before and/or during the treatment. Some types of supporting matrix may enable an attached applicator to be arbitrarily positioned without limitation of the placed applicator's spots. Such a supporting matrix may fix applicator(s) to arbitrary applicator spots by a removable fastening member and/or chemical, magnetic, electrical, and/or suction mechanisms, by inserting an applicator into a pocket in the support matrix, by Velcro, by loop tape, by magnet, by tacks and/or by any other of one or more types of fastening member. Such a supporting matrix may also include multiple holes that enables mechanical fastening with a fastening member to an applicator fitted with a specific protrusion.

According to some embodiments the supporting matrix may not be divided by any applicator spots.

Some parts of the supporting matrix may be made of flexible, elastic and/or rigid materials e.g.: polymeric materials, ceramics, textile materials, conductive parts and/or other materials. The supporting matrix may be at least partially flexible and/or elastic to provide improved contact with the patient body and/or set an appropriate working distance for one or more applicators.

The support matrix may also contain apertures of different sizes and shapes. The support matrix may include a system for moving the applicator to move across the belt area, one or more sensors, a processor and/or memory. In some embodiments a mechanism of moving attached applicators and/or treatment energy sources may be provided according to a defined pattern. A trail for the applicator may be created by some system of rails for moving one or more component of the supporting matrix (e.g: applicator may be moved along them by mechanical forces based on pressure and/or tensile forces) and/or by a rail created from conductive elements, and applicators may be moved along them by electric, magnetic and/or electromagnetic forces caused by powering such conductive elements.

Movement of one or more applicators and/or treatment energy sources across the patient body may also be provided by movement of the supporting matrix. Movement of the supporting matrix may be provided by expansion and/or shrinking of some parts of the supporting matrix and/or by moving the supporting matrix along a spacing object (e.g. by mechanical, electrical, magnetic and/or combination of these forces) and/or by attaching the supporting matrix to any other movable parts of the device (e.g.: mechanical arm, construction on rails etc.)

The supporting matrix may include conductive parts that may provide communication between e.g.: applicators, applicators and the control unit, applicator(s) and treatment units and/or applicator(s) and external devices. Conductive parts in the supporting matrix may also provide a power supply to the applicator(s). Applicator(s) may include one or more rechargeable batteries as a source of energy. These batteries may be recharged through the supporting matrix and/or through the spacing object.

According to another embodiment the supporting matrix may also determine the applicator(s) e.g.: location in the supporting matrix, type, contact with the supporting matrix, and distance from the patient's surface. The supporting matrix may also provide feedback information and/or other features.

This sheet may contain conductive components. A hardware pattern may be created by placement of the applicators into the belt (e.g. supporting matrix) attached to patient's body. According to one embodiment the master or control unit may propose ideal hardware and/or treatment patterns based on the selected treatment protocol in order to optimize selected treatment effect(s) of selected body part(s). The master or control unit may also take into account supportive information parameters of the patient like age, sex, weigh, height, BMI, skin type and others.

The master unit and/or control unit may also propose one or more treatment effects, treatment protocols and/or treatment patterns according to the hardware pattern of the belt. According to a specific embodiment the device may be able to select the treated body part and/or the device may be able to determine the body part according feedback information from at least one sensor.

A treatment pattern may be created in several possible ways. A treatment pattern may be created by movement of at least one treatment energy source(s) and/or applicator(s) across the patient's surface. Means of moving the treatment energy source(s) may be provided within the applicator and/or by moving one or more applicators. Means of moving the applicators may be provided e.g. within the supporting matrix that may include movable parts. Means of moving the applicator(s) and/or treatment energy sources across the patient's surface may be provided e.g.: by a movable component of the applicator and/or the supporting matrix pushed by air/liquid pressure, by electromotor, by electric and/or magnetic forces causing movement of a movable part of the applicator, movement of the supporting matrix, and/or movement of the entire applicator. Movement of the treatment energy source and/or the applicator may be based upon principles described in U.S. patent application Ser. No. 15/433,210 incorporated herein by reference.

According to a preferred embodiment the treatment pattern may be created by switching on/off or varying intensity of delivered treatment energy between individual and/or groups of treatment energy sources. Switching between treatment energy sources or varying intensity of delivered treatment energy between treatment energy sources may simulate movement of at least one treatment energy source guided by operator. The creation of said treatment pattern may be based on principles described in U.S. patent application Ser. No. 15/433,210 incorporated herein by reference.

Figure 17:
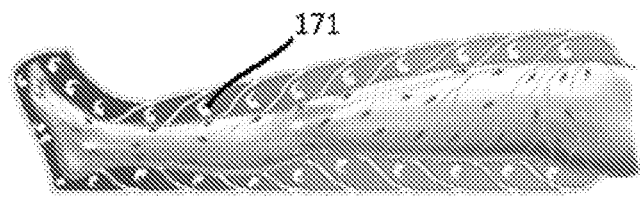
FIG. 17 illustrates influence of pressure on lymph and blood circulation.
Figure 18:
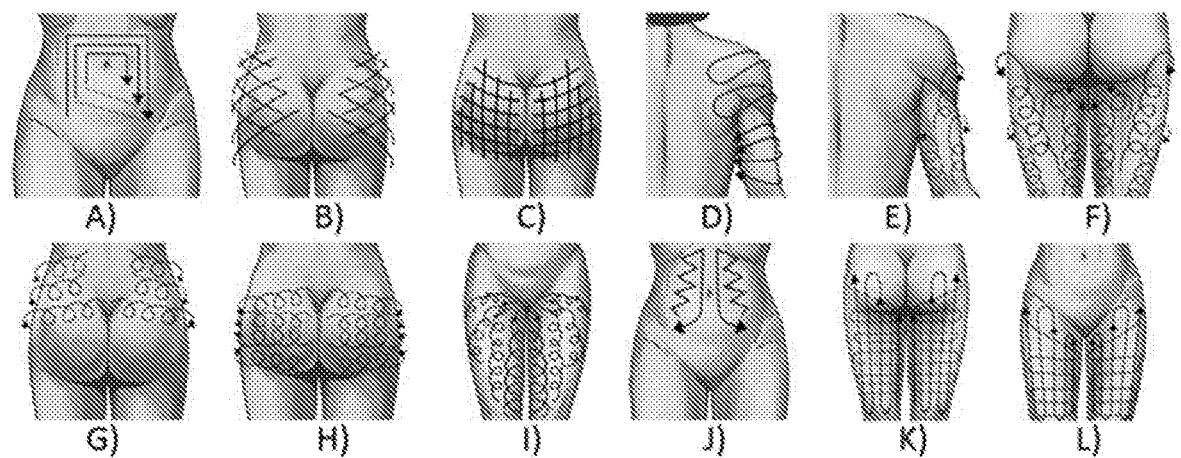
FIG. 18 illustrates treatment/massage patterns.

Massage and or other therapy may be provided in a pattern that is created by switching between previous and successive treatment energy sources. For example, in FIG. 17 a massage unit with pressure cells may create pressure individually, simultaneously, sequentially and/or with overlay in cooperation with one or more other elements changing pressure value. A treatment protocol may include information about a massage/treatment pattern e.g. which, when and/or for how long massage unit(s)/treatment unit(s) are switched on/off. Other characteristics of the treatment protocol for a defined massage/treatment pattern are parameters of delivered treatment energy source(s) and/or pressure parameters of the massage unit or group of massage units that are activated (switched on/off) according defined contiguity. A treatment pattern may simulate movements with an activated treatment energy source. FIG. 18 shows various treatment patterns. Treatment patterns may simulate: linear moves that may overlap e.g. as shown in FIG. 18A)-C); curvilinear moves e.g. as shown in FIG. 18D); curvilinear moves that may imitate progressive circular moves e.g. as shown in FIG. 18E)-I) and/or a combination of these as shown in FIG. 18J)-L).

Massage/treatment patterns in some treatment protocols may simulate massage/treatment provided by a physiotherapist and may enhance massage/treatment provided by a physiotherapist. The present apparatus and methods are not limited to just the two hands of a physiotherapist, or by the strength and fatigue of a physiotherapist. Massage provided by the present designs may also be provided in a different manner than applied mechanical pressure e.g. acoustic waves that may be more targeted and/or may selectively provide massage of deep soft tissue layers without influencing upper soft tissue layers that a physiotherapist is not able to provide. This massage/treatment pattern may change during the treatment.

Various treatment patterns and pressure gradients may be achieved by a treatment sleeve comprising a plurality of treatment energy sources and/or elements changing pressure value arranged in e.g. a line or matrix by providing successive therapy. Successive and previous treatment energy sources may be any kind of treatment energy sources. The successive and the previous treatment energy sources and/or equivalently successive and previous elements changing pressure value must comply with the prescribed requirements:

The successive and the previous treatment energy sources provide variable output power during treatment; the successive treatment energy source provides the same treatment therapy as the previous treatment energy source; the successive treatment energy source is included in the same treatment sleeve as the previous treatment energy source; and the successive treatment energy source is the source which starts to increase the output power value after the previous treatment energy source increases its output power value.

According to one embodiment more than one successive treatment energy source may increase output power at the same time.

It is possible to designate more than one treatment energy source as the previous treatment energy source that is distinguished from the previous treatment energy source for one specific successive treatment energy source and it is the one with the shortest distance from the successive treatment energy source.

Designation of a previous and successive treatment energy source is changing during switching on/off or changing output power between individual treatment energy sources in order to simulate movement of the treatment energy during the therapy.

When a successive treatment energy source is activated, a previous treatment energy source may or may not be still activated.

A treatment energy source is considered as activated when it is providing any wanted treatment energy type (any treatment therapy) to the patient's soft tissue.

Successive therapy creates a pattern and may be defined relative to successive therapy speed. The successive therapy speed describes a speed of moving, changed intensity of treatment energy source/elements, and changing pressure value along the treatment pattern. Successive treatment therapy may be provided by switching between previous and successive treatment energy sources and/or changing output power between previous and successive treatment energy sources. The successive therapy speed is then counted as a division of distance between central parts of previous and successive treatment energy sources and time delay between starts of output energy rising of previous and successive treatment energy sources. The successive therapy may also be provided by moving the treatment energy source relative to the patient's surface. Then the successive therapy speed is moving speed of the treatment energy source. According to still another embodiment the successive therapy may be achieved by changing spatial coordinates of a focal spot across the treated body area (changing of focus depth in the soft tissue is not included). Then successive therapy speed is speed of moving a center of the focal spot across the patient soft tissue. The successive therapy speed is measured in units of $cm \cdot s^{-1}$.

Average successive therapy speed may be in range between $0.1$ $cm \cdot s^{-1}$ and $50$ $cm \cdot s^{-1}$ or more preferably in range between $1$ $cm \cdot s^{-1}$ to $30$ $cm \cdot s^{-1}$ or the most preferably in range between $5$ $cm \cdot s^{-1}$ to $15$ $cm \cdot s^{-1}$.

The treatment pattern created by at least one, but more preferably, at least two types of treatment energies by at least two treatment energy sources is characterized by at least one, more preferably, at least two target spots of specific and/or different treatment energy sources that may vary treatment energy intensities with respect to time and/or spatial coordinates—usually located within the patient's tissue. The target spot is a location where treatment energy is delivered, and which has an absolute value of provided treatment energy intensity above zero. The target spot may be created by providing focused and/or non-focused treatment energy. The center of a target spot is a spatial coordinate where the absolute value of the provided treatment energy intensity is the highest (e.g. center of the treatment energy source). In one embodiment the treatment pattern may be created by a continuous or discontinuous trajectory of the target spot(s) across spatial coordinates. The target spot(s) may vary intensity of delivered treatment energy during the trajectory described by the treatment pattern. Movement of the target spot may be provided by movement of at least one treatment energy source that usually creates the continuous trajectory of target spot(s) and/or by varying treatment energy intensities between at least two treatment energy sources wherein the target spots may overlap and create continuous trajectory and/or may not overlap that creates a discontinuous trajectory of the target spot described by treatment pattern. Changing spatial coordinates of the center(s) of target spot(s) across patient's tissue during the time may be described by the treatment pattern speed. The treatment pattern speed may be also described as a ratio of the target spot's distance and time delay. A spot's distance is the distance between the centers of the target spots of at least two of the nearest treatment energy sources reaching maximum treatment energy intensity during shortest time delay. The time delay may be described as a time delay between above mentioned centers of target spots reaching their absolute maximum values of treatment energy intensities. The average treatment pattern speed may be in the range between 0.1 cm·s$^{-1}$ and 50 cm·s$^{-1}$ or more preferably in a range between 1 cm·s$^{-1}$ to 30 cm·s$^{-1}$ or most preferably in a range between 2 cm·s$^{-1}$ to 15 cm·s$^{-1}$.

The treatment pattern speed may be constant and/or may vary during one treatment pattern.

The treatment pattern provided by a first type of treatment energy may be also accompanied by other types of one or more treatment energies provided to the patient's tissue. Such other treatment energies may follow the treatment pattern of the first treatment energy with the same or a different treatment pattern speed and/or may follow different treatment pattern(s).

Treatment patterns may also be created by varying treatment energy intensities of multiple treatment energy sources that reach their maximums of absolute value of treatment energy intensities at the same time. According to such an example, the treatment pattern speed may be described, as was described above, as a ratio of a target spot's distance and time delay.

The treatment pattern may change during one treatment based on one or more treatment protocols.

During one treatment, a patient may be provided one or more treatment patterns simultaneously and the treatment pattern may also overlap and/or build on itself.

Figure 8:
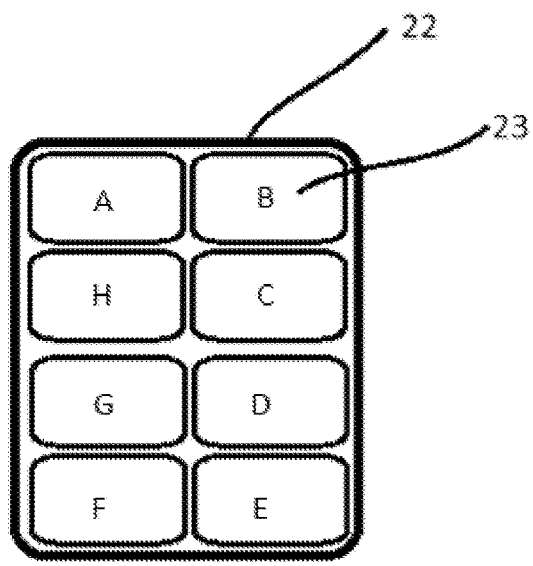
FIG. 8 illustrates the active surface of an applicator with multiple treatment energy sources.

An applicator including more than one treatment energy source may create its own small treatment pattern by switching between individual treatment energy sources. The small treatment pattern created by one applicator may be part of bigger treatment pattern created by switching between individual applicators. In FIG. 8 where 22 symbolizes the applicator's active surface with multiple treatment energy sources A-H and 23 symbolizes one of the treatment energy sources. The applicator may contain treatment energy sources with different shapes. The number of treatment energy sources in one applicator is not limited. Switching on/off between treatment energy sources, changing of the treatment energy intensity between treatment energy sources and/or movement of the treatment energy sources during the treatment may be defined by treatment protocol. The treatment energy sources of at least one applicator can work simultaneously, with some overlay and/or sequentially during the treatment. Also one or more treatment parameters of the procedure may be adjusted before and/or during the treatment.

The applicator and/or the treatment energy source may provide multiple treatment effects. According to one embodiment one applicator may include treatment energy sources producing one or more types of treatment energies e.g. one treatment energy source may produce shock waves, ultrasound and/or acoustic waves during one treatment.

Time intervals between the power amplitudes of delivering treatment energy to the patient's body by individual treatment energy sources may overlay and/or may be divided by a pause time interval in the range between 01 ms to 15 s or 1 ms to 5 s or 100 ms to 3 s.

Figure 15:
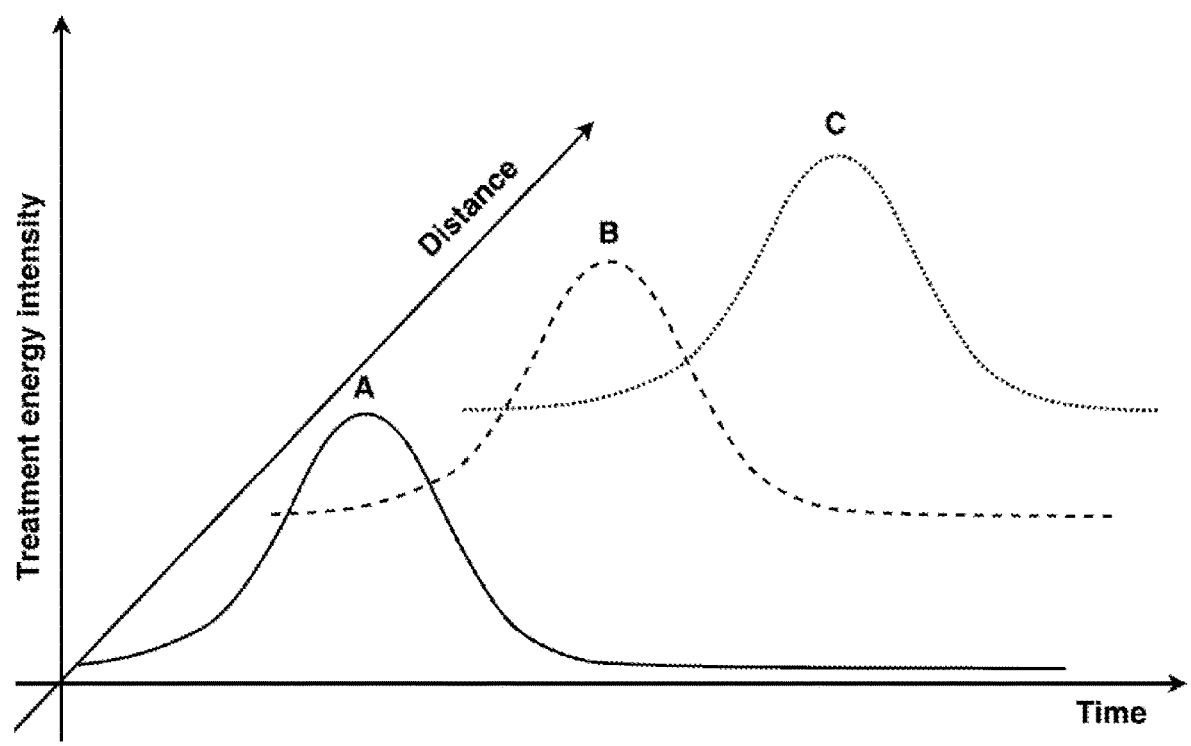
FIG. 15 illustrates a possible example of three time-domain functions of treatment energy intensities provided by individual treatment energy sources arranged in a hardware pattern.

FIG. 8 describes one possible positioning of treatment energy sources. The respective treatment energy sources may provide a treatment pattern by varying intensity of delivered treatment energy between the respective treatment energy sources as depicted in FIG. 15. Treatment energy source A may temporarily increase intensity of provided treatment energy A to patient's body (see peak A). After treatment energy intensity A rises above the initial treatment energy intensity value, treatment energy intensity B provided by treatment energy source B (see peak B) may also start to temporarily rise. The same principle as was described for treatment energy source A and B may be repeated for treatment energy sources C (see peak) and D, E, F, G, and H and that may create a circular treatment pattern with a clockwise direction that may be repeatedly used. The treatment pattern speed between treatment energy sources A and B according to FIG. 15 may be quantified as the distance between maximums of peaks A and B in a ratio with the time delay between when peak A and peak B reach their maximums.

The various other treatment patterns as described in this document may be used.

According to another embodiment peaks A, B and/or C in the FIG. 15 may represent different types of treatment energies e.g.: RF, ultrasound and/or shock wave. Peaks A, B and/or C may have the same and/or different profiles, maximal values and/or integral values. A treatment energy intensity peak may have no overlap and/or may at least partially overlap in terms of spatial coordinates and/or time.

According to the treatment pattern in FIG. 15, the peak of the first treatment energy intensity (peak A) may start to decline sooner, at the same time or after the second treatment energy intensity (peak B) starts to decline and/or reaches its maximum intensity value.

Also target spots created by the same and/or different treatment energy types during a treatment pattern may have no overlap and/or may at least partially overlap in the patient's tissue.

According to one preferred embodiment a pattern with at least two different energy sources providing different treatment energy may be used.

Figure 9:
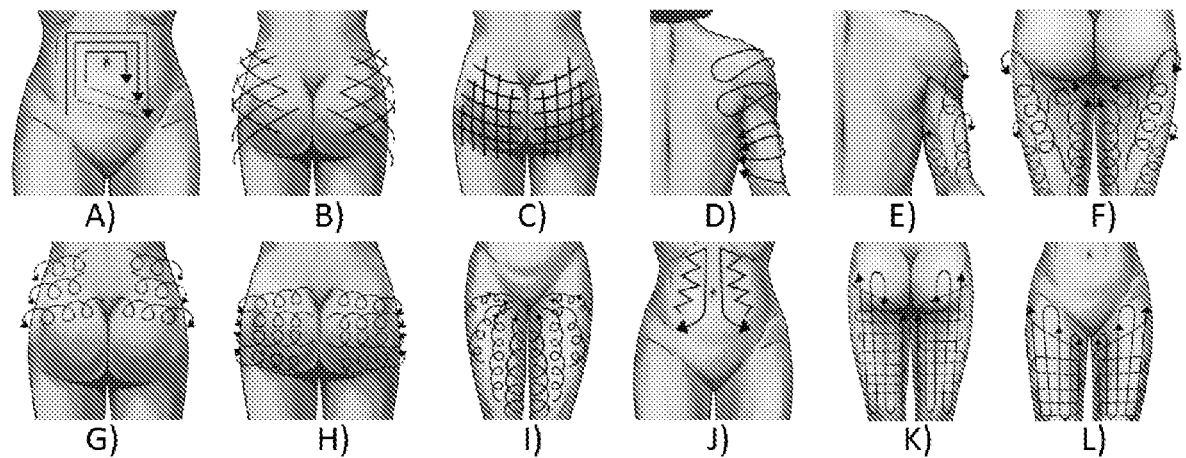
FIG. 9 demonstrates several treatment patterns provided across the patient's surface.

The pattern with at least two different energy sources providing different treatment energies may provide a synergistic effect by influencing the treatment results. One illustrative example of such synergy may be a pattern consisting of RF and focused ultrasound energy sources where the ultrasound energy source provides heating in the target spot and then the RF is more readily absorbed by the preheated tissues, while continually simulating movement according to the chosen pattern Possible treatment patterns (see FIG. 9) may simulate linear movements of treatment energy source(s) across the patient's surface (See FIG. 9A-C). FIG. 9D simulates curvilinear movements, FIG. 9E-I simulates several types of circular movements, and/or FIG. 9J-L simulates a combination of linear and curvilinear movements.

The treatment pattern may not be limited only by movement of the treatment energy target spot in two dimensional movements with respect to patient's surface. The treatment pattern may determine the depth of the treatment energy target spot. One illustrative example may be a pattern consisting of RF and focused ultrasound energy sources where the focused ultrasound energy source provides heating in the target spot at one depth and then the RF is more readily absorbed by the preheated tissues, while continually simulating the movement according to the chosen pattern, which simulates movement of the target spot in tissue in one, more preferably two, or most preferably three dimensions. The depth and planar location of the target spot may vary in time based on selected treatment protocol.

Figure 10:
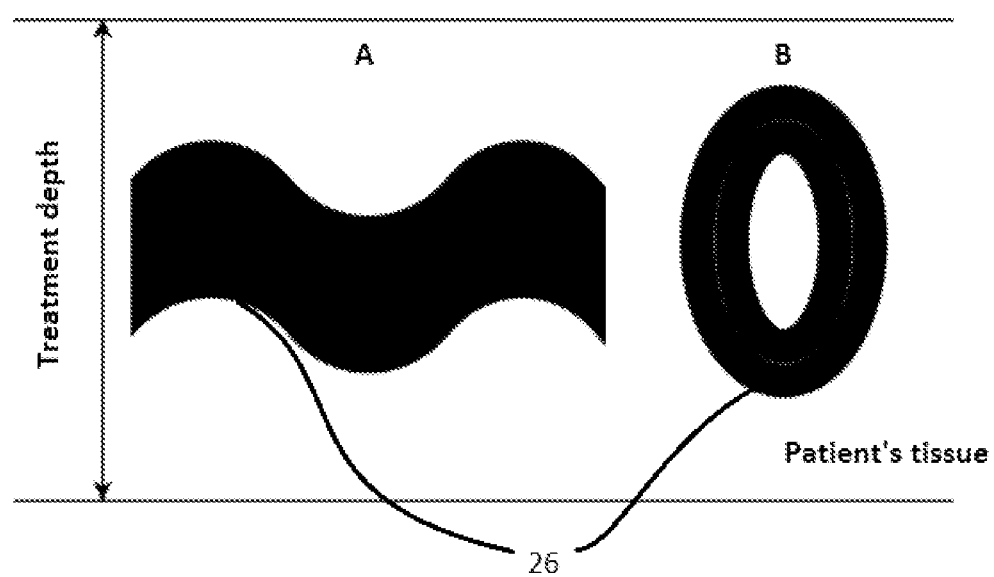
FIGS. 10A and B illustrate treatment patterns provided into a depth of the patient's tissue.

A treatment pattern with and/or without a defined treatment depth pattern may be cyclically repeated. FIG. 10A illustrates one possible example of a short sequence of treatment patterns with varied treatment energy focus depths 26 by changing the horizontal coordination of a treatment energy target spot in the patient's tissue. Horizontal coordinates are parallel to patient's surface curvature under the belt at every space coordinate under the belt. For example horizontal coordinates in the patient's hip area according to some patients' body types may be described as a convex surface area in Cartesian coordinates. FIG. 10B illustrates one possible example of a treatment pattern with varied treatment energy focus depth 26 by changing the horizontal coordination in the patient's tissue over time. Treatment energy focus depth 26 may be also varied during the time of the treatment without regard to changing horizontal coordinates of the treatment energy target spot. The depth of the treatment energy target spot may be varied also for non-focused treatment energy e.g. by changing the intensity of delivered treatment energy, changing the wavelength, polarization of treatment energy, changing the distance between electrodes providing RF treatment energy and/or by changing other parameters of delivered treatment energy to the patient's body.

The depth of a treatment energy target spot may be varied also by changing parameters of patient's tissue for example by providing another treatment energy e.g. heating or cooling of the patient's tissue that may increase penetration of the RF waves, or by applying an electric field that may influence dielectric behavior of the patient's tissue.

Various kinds of treatment patterns may be provided by various kinds of hardware patterns. Cooperation of a hardware pattern and a treatment pattern may significantly improve treatment result(s), shorten treatment time and/or may increase treatment safety. Exemplary variants of hardware patterns providing a treatment pattern are provided below. According one exemplary variant, one option may be sequential and/or simultaneous application of one or more treatment energies heating the patient's tissue and/or damage tissue cells with treatment energy that accelerates metabolism, blood flow, lymph flow and/or accelerates the removal of damaged cells. A simulated movement trajectory may be like what is illustrated in FIG. 9A-L. An example of such a treatment pattern may be alternately placing treatment energy sources providing e.g.: RF, shock waves, ultrasound, light; and treatment energy sources providing massage and/or muscle stimulation like e.g. a suction mechanism, a muscle stimulating magnetic field, a muscle stimulating electrode, a movable massage element providing mechanical pressure and/or any other.

According to one exemplary variant, one option may be using one or more treatment energy that heats patient's tissue and/or damaged tissue cells in combination with at least one treatment energy that accelerates metabolism, blood flow, lymph flow and/or accelerates the removal of damaged cells. The combination of such at least two different treatment energies may be simultaneous, with some overlay, sequential and/or may be applied in close proximity to allow the synergistic effect of at least two different types of treatment energies. An applicator and/or treatment energy sources in an applicator may be distributed in a 2D and/or 3D matrix. For example applicators including different types of treatment energy sources may be placed in close proximity to the supporting matrix and/or to the patient's body and coordinated variation of treatment energy intensities may simulate movement of at least one applicator as it is illustrated in the FIG. 9A-L.

An example of such a treatment pattern may be alternately placing treatment energy sources providing e.g.: RF, ultrasound, shock wave or light in combination with treatment energy sources providing e.g.: acoustic wave, massage and/or muscle stimulation by a suction mechanism, a magnetic field, a current, a movable massage element providing mechanical pressure and/or any other.

Figure 13:
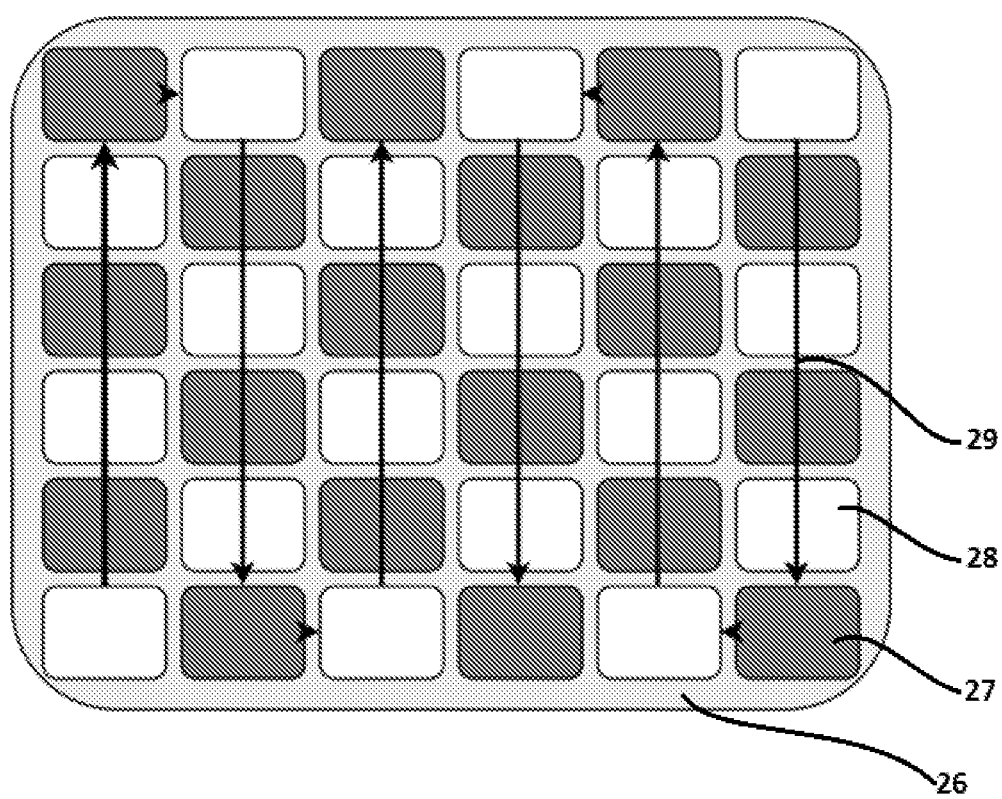
FIG. 13 illustrates one possible symmetric hardware and treatment pattern.
Figure 14:
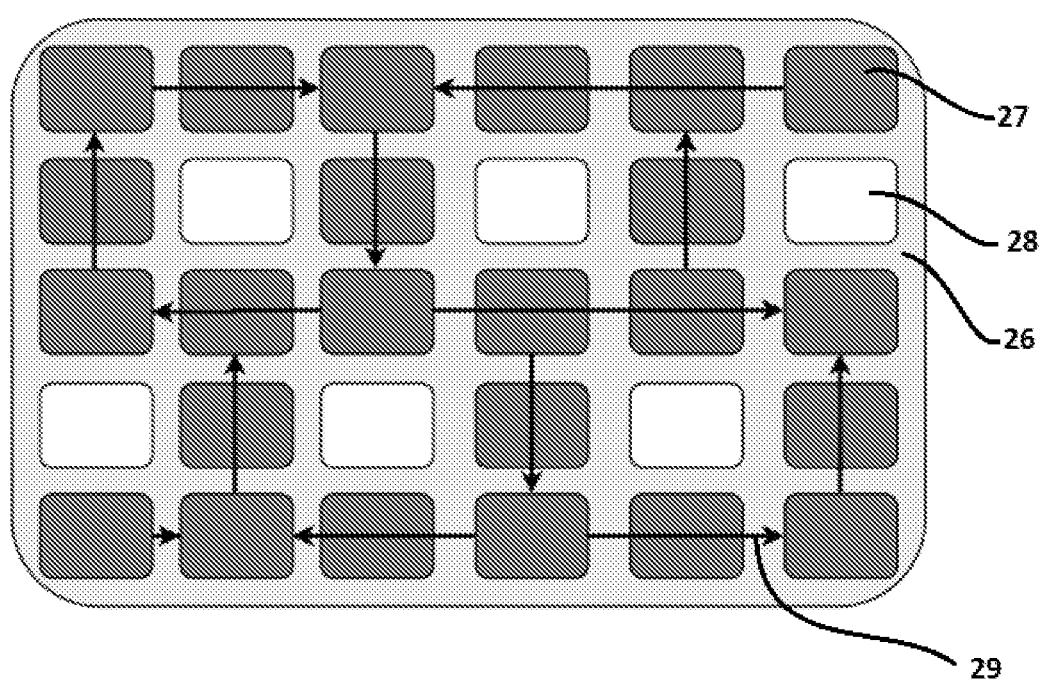
FIG. 14 illustrates one possible symmetric hardware pattern and asymmetric treatment pattern.

The placement of different treatment energy sources/applicators may be one of the most important parameters of the treatment. FIGS. 13 and 14 illustrate two types of treatment patterns. FIG. 13 illustrates alternately placed treatment energy sources 27 providing heating of the patient's tissue, creating cell damage and/or tissue structural damage e.g. by: RF, ultrasound, shock wave or light etc. in combination with treatment energy sources 28 providing acoustic wave, massage, stimulation of lymph flow, blood flow and/or metabolism stimulation. Treatment energy sources 27 and 28 may be attached to a supporting matrix 26. Arrows 29 symbolize the direction of the treatment pattern and orientation of the speed of the treatment pattern therapy.

FIG. 13 provides a symmetric treatment pattern simulating linear movement of two treatment energy sources. According to another example treatment energy sources 27 may be placed around the treatment energy sources 28 (see FIG. 14). Symmetric placement of treatment energy sources and/or applicators may create also asymmetric and/or partially symmetric treatment patterns depending on the resulting pattern created by varying intensities between multiple treatment energy sources at the same time (see arrows 29). The resulting pattern according to arrows 29 in the FIG. 14 imitate partial symmetric circular movement by multiple treatment energy sources.

According to FIG. 14 treatment energy intensities provided by treatment energy sources 27 may simulate circular movements and treatment energy sources 28 may provide continual and/or pulsed blood, lymph and/or metabolism stimulation.

According to another embodiment the treatment pattern(s) may also be created by treatment energy sources that change the location of treatment energy target spots in the patient's tissue by its movement. The changes may also be target spot volume, target spot depth, target spot shape and/or target spot coordinates according to the horizontal plane in the patient's tissue.

The treatment patterns described in FIGS. 13 and 14 are not limiting examples.

According to one exemplary variant one or more treatment energies may provide treatment of hypodermal tissue and one or more different treatment energies may provide treatment of epidermal or dermal tissue. The combination of such at least two different treatment energies may be simultaneous, with some overlay, or sequential, ensuring faster treatment of more than one tissue problem. An example of such a treatment pattern may include use of a treatment energy source providing hypodermal treatment by RF, ultrasound, shock wave, light or magnet and a treatment energy source providing epidermal or dermal treatment by light, plasma, or RF.

According to another exemplary variant one or more treatment energies may provide treatment of epidermal tissue and one or more different treatment energies may provide treatment of dermal tissue. The combination of such at least two different treatment energies may be simultaneous, with some overlay, or sequential, ensuring faster treatment of more than one tissue problem. One example of such treatment a pattern may include use of treatment energy source providing epidermal treatment by light or plasma; and a treatment energy source providing epidermal or dermal treatment by RF, ultrasound, shock wave, or light.

The described variants may also damage cells and/or tissue structure by a first treatment energy source and accelerate healing of the tissue by the second treatment energy source.

Attachment of the applicator to the belt or the belt to the patient may be provided by: gravitational force, by roughness of contact surfaces, by electrical forces, by magnetic forces, by chemical bonds (e.g. interaction between polar molecular groups on at least one of the contact surfaces), via fastening member(s) e.g. working on a clam mechanism and/or any combination thereof. A fastening member may be a permanent or removable part of any applicator, supporting matrix, spacing object and/or any other part of the device (e.g. treatment unit(s) and/or mother case). A fastening member may be an adhesive polymer or copolymer (e.g. poly(styrene/ethylene/butylene) which is located at one or more contact sides of the fastening member. A fastening member may also be designed as: rails, a sticky layer between two contact sides, elastic, partially elastic and/or non-elastic strips, lace, Velcro, a zipper, a snap, a clamp, tacks, a member creating lower air pressure between contact surfaces e.g.: by a suction mechanism, by a layer providing interaction between polar and/or non-polar groups on the contact surfaces and or a member using physical means (e.g.: electric, magnetic forces), chemical means, or a mechanical interaction between fastening member(s), parts of the device and/or between patient surface.

Fastening members may have different sizes, shapes and in one embodiment may be a combination of different types of fastening members.

The applicator(s) may be attached at the optimal working distance by a fastening member designed as one or more strips located on the front and/or back side of the applicator. Suitable elastic materials are elastomers or also elastic fabrics. The elastic belt material also adapts to respiratory movements and/or other movements of the patient. The fastening member designed as strips may also include conductive component(s) that may be connected and/or communicate with the supporting matrix and/or other part(s) of the device. Such conductive components may also recharge one or more applicator(s) and/or the supporting matrix.

The supporting matrix may hold one or more applicators in close contact with patient's body surface and/or it may also hold one or more applicators at an optimal working distance from the patient surface. The patient's surface is typically the epidermis of the patient. However, the patient's surface may alternatively be some spacing object e.g.: clothing worn over the skin, a sheet, a pad or other thin (0.1-2 mm) covering over the skin, and/or a thicker spacing object. The spacing object may provide a suitable working distance for the applicators, may provide heating/cooling of the patient body, may provide massage of patient's soft tissue, may provide several modifications of delivered signal to the patient soft tissue (e.g.: polarization), filtration of a provided signal to the soft tissue, better transfer of a signal to the soft tissue, changed direction of the pointing vector of a provided electromagnetic field, prevention of an edge effect and/or any others as described in U.S. Provisional Application No. 62/331,072, incorporated herein by reference. A spacing object may be located between any parts of the device e.g. between the supporting matrix and applicator(s) and/or between the patient and parts of the device (e.g. between the patient and supporting matrix and/or between the patient and applicator(s)). Because of mechanical, structural, physical and/or chemical properties of this spacing object, the spacing object may provide and/or improve attachment of any parts of the device and/or parts of the device and the patient body surface together.

A filler of the spacing object may be gaseous, liquid and/or from solid material. A spacing object may be composed of any kind of ceramic, plastic material, rubber, textile material, metal, polymeric materials and/or any other material that improves any therapy parameter(s). In some embodiments it may be important to choose a material and/or construction of the object to provide a stable form and/or shape of the spacing object. A spacing object may be flexible and/or rigid and may imitate curves of the body contour.

Treatment by electromagnetic field and spacing object enabling changing of temperature and/or other parameters (permittivity, permeability, conductivity and/or their parameters) and/or its one or more component may create temperature gradients across the soft tissue of the patient. This is very important because tissue dielectric parameters (e.g. impedance, conductivity and/or other related dielectric parameters) change with different temperature and frequency of applied electromagnetic waves. Targeting of thermal gradient by applied electromagnetic field and continuous but more preferably sequential heating and/or cooling of the patient surface by the spacing object may improve the effect of the treatment and minimize health risk.

Filler of the spacing object may provide polarization and/or reflection and/or may focus delivered electromagnetic energy and/or may be used as a filter of electromagnetic waves and/or may adjust an orientation of the wave vector of the electromagnetic wave as was mentioned below. Polarization of the electromagnetic wave has a different impact on different molecules and environments, so polarization may influence absorption, dispersion, penetration, targeting and/or reflection of the electromagnetic wave. Polarization of the electromagnetic wave may be created by anisotropic arrangement of dielectric films (e.g. by poly (vinyl alcohol) doped by iodine or other substances based on dichroic polarizers principle) and/or by principle of the phase retardation plate and/or by material and/or geometry of the antenna. Some polarization and reflection elements may have crucial influence to prevent creating hot spots due to changing of the orientation of the wave vector and selective modification of the component of the electromagnetic wave.

Cooling or heating of tissue may be ensured by a spacing object filled with a suitable substance (mostly liquid or gaseous substances e.g. water, water doped NaCl, ethanol, air, $N_2$, $CO_2$, air and others). The parameters of the substance such as temperature, viscosity, flow etc. may be monitored by one or more sensors (e.g. temperature and/or viscosity sensors and/or sensor measure inducted currents or chemical changes of the substance).

Figure 19:
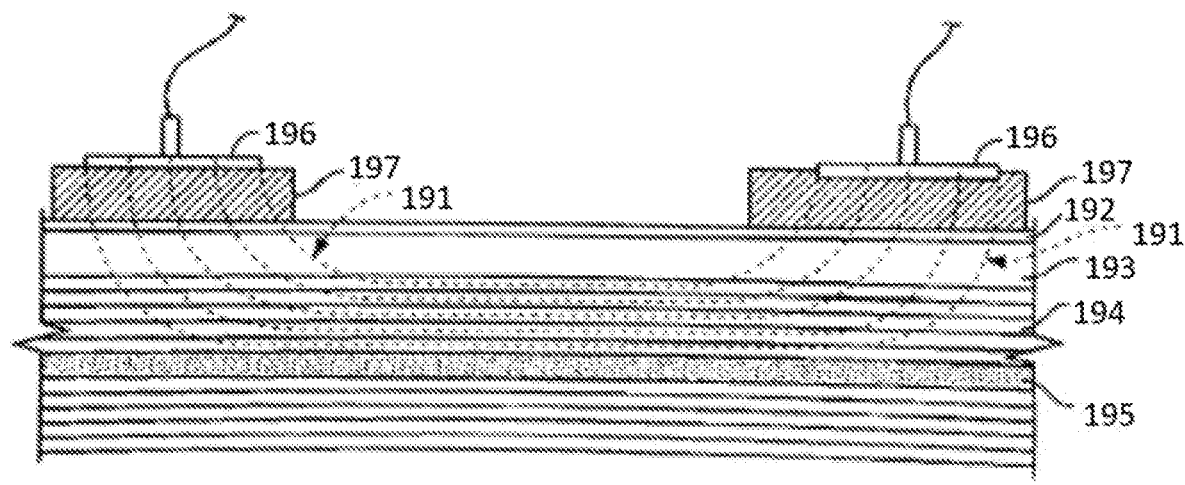
FIG. 19 is a schematic diagram of a system for controlled deep heating of sub dermal tissues.

FIG. 19 is a schematic representation of a heat distribution under the skin. One or more applicators 196 create an electromagnetic field. This electromagnetic field crosses through the skin 192, subcutaneous fat 193 and muscle 194 or the bone 195. Capacitive applicators 196 provide deep heating, which heats selectively only structures with low volume of water. A spacer 197 such as an object, towel, gauze pad, foam pad, cloth pad or other porous or air permeable materials may be placed on the skin, with the applicator then placed on top of the spacer 197. The spacer may be made from a three-dimensional material with high air permeability formed by two square fabrics with preferably low square densities connected by tough filaments. This automatically sets the separation distance between the applicator and the skin, and prevents the applicator from touching the skin. The spacer 197 may be made of various dielectric or electrically non-conductive materials. The spacer 197 is typically dry in use. Alternatively, a reusable or a disposable spacer may be attached to the applicator. For example, the spacer may comprise posts, a frame, or other structure on the applicator that contacts the skin, while keeping the active surface of the applicator spaced apart from the skin. As described and claimed here, such spacing elements are additional elements and not part of applicator. The methods may be performed with no part or surface of the actuator in contact with the skin.

The belt may at least partly encircle any part of the patient's torso and/or limb.

Feedback information may be collected by different types of sensors and may have different characteristics (e.g.: biological, chemical, physical etc). One or more sensors may be located in the supporting matrix, in one or more applicator(s) and/or may be located externally outside of the belt (e.g.: optical, sonic and/or others located around a patient). One or more sensors may control treatment parameters (e.g.: the intensity of delivered energy into the tissue, the sequence of applied treatment energy, changed parameters of the delivered signal, switching on/off of different treatment energy sources and/or others). The device may contain different types of sensors for monitoring device parameters, monitoring of the body via biological, physical, chemical and/or other parameters (e.g. an electrochemical sensor, a biosensor, a biochemical sensor, a temperature sensor, a sensor for measuring the distance of an applicator from the patient surface, from some area of the patient soft tissue and/or from other applicator, a sensor to determine the position of the device with regard to patient's body part, a sensor for recognition of the applicator orientation in 3D space, a rotational orientation sensor, a sorption sensor, a pH sensor, a voltage sensor, a detector of moving velocity and/or a change of treatment energy source position, a sensor to detect a change of focus target area of the treatment energy, a photo sensor, a sensor measuring fluid viscosity, a camera, a sensor for measuring fluorescence of the patient surface, a sound detector, a current sensor, a sensor for measuring of specific heat capacity of human/animal tissue, a sensor for measuring the value of a magnetic field, a sensor for measuring impedance, permittivity, conductivity, or susceptibility). The device may also contain any suitable sensor or sensors for measuring biological parameters and/or any combination thereof (e.g.: a sensor for measuring dermal tensile forces; a sensor for measuring the activity of the muscle; a sensor for measuring muscle contraction forces; a sensor for measuring pulse of the patient; a sensor for measuring skin elasticity). The device may also include at least one contact sensor for monitoring applicator contact with the body surface of the patient. The supporting matrix may also recognize the type and/or location of one or more of the different applicators attached to the supporting matrix.

The applicator(s) may be able to communicate with each other and/or other parts of the device (e.g. an external device, a control unit, a treatment unit and/or others) as was mentioned above. This communication may provide information from feedback sensors, about position of one or more applicators, 3D orientation of the applicator(s), information about contact of the applicator(s) with the patient and/or the supporting matrix, distance from the patient surface, parameters of the treatment protocol, parameters of each applicator and/or other information from one or more sensors. Data from the different applicators and/or types of sensors may provide complex information about the treatment and/or the treated soft tissue. Information from the sensors may be used to determine which part of the patient is treated, determine the exact composition of treated tissue and/or changes in the patient's tissue during the time of the treatment. These sensors may cooperate with one or more treatment energy sources provided and may be used as an imaging device of the surface and/or deeper layers of the patient soft tissue. The imaging system of the soft tissue before and/or during the treatment may improve safety of the treatment, determine when the treatment is complete, monitor treatment process and/or progress of the treatment. This processed data may be used for adjusting parameters of the treatment procedure, may activate other treatment energy source(s) and/or one or more treatment protocols (e.g. activate massage, cooling, heating and/or others) and/or change any other parameter of the treatment protocol. This data may also warn the operator and may be used as a prevention of health risk and/or may prevent damage to any part of the device.

The treatment protocol may include several instructions that define treatment of one or more treatment energy sources and/or applicator(s). The treatment protocol may include information about e.g.: the treatment pattern, the treatment pattern speed, which treatment energy source(s) are switched on/off and/or parameters of individual treatment energies produced by individual treatment energy source(s). The treatment protocol may also include information about applicator(s) and/or the treatment energy source hardware pattern. The treatment protocol may also include information about the system of collecting feedback information e.g. which sensors communicate with which part of the device. According to some embodiments the treatment protocol may also include information on how parts of the device communicate with each other, how information will be processed during the treatment, or which parts of the device and/or treatment protocol may also define priority of commands during device communications. Other examples of information that may be included in treatment protocol include: applied treatment effect(s), shapes and types of a delivered signal of treatment energy into the tissue (symmetrical; asymmetrical; polarized; non-polarized; continual or sequences of signal pulses; timing of the delivered signal; shape of the signal: sine, square, triangle, saw tooth and/or others), the defined pulse sequence intensity of delivered energy, polarization of a delivered electro-magnetic signal, the remaining time of treatment procedure, threshold parameters, the time and/or sequence of heating/cooling of the soft tissue and/or other parameters that influence treating of the soft tissue by one applicator (e.g.: geometry and position if it is possible to change this parameter and/or other parameters).

Figure 12:
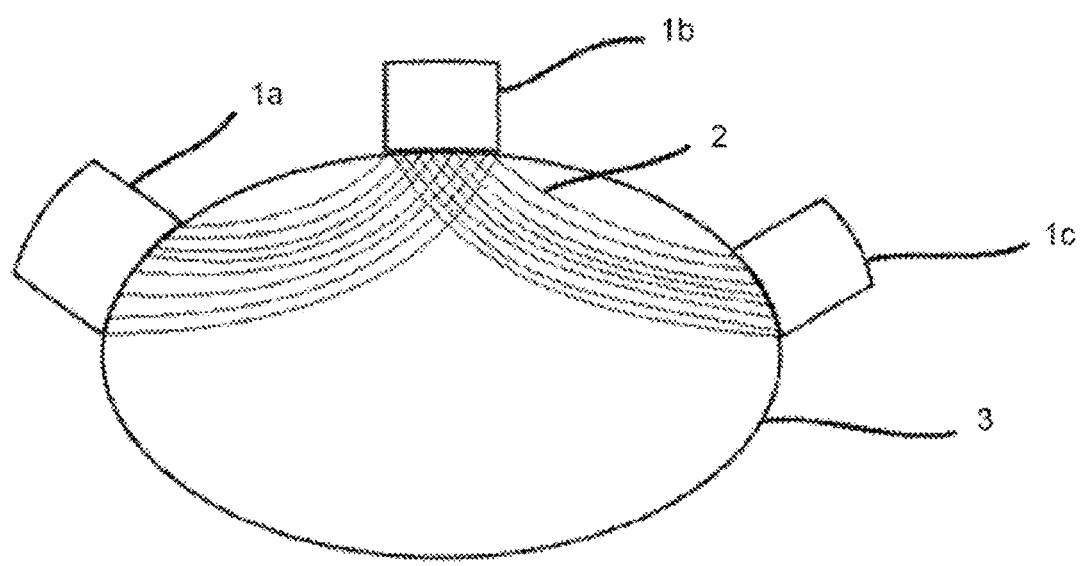
FIG. 12 illustrates a multipolar treatment of three cooperating applicators.

Several applicators may cooperate with each other. FIG. 12 describes cooperation of multiple applicators 1a, 1b, 1c that may provide treatment energy or energies (e.g. multipolar RF therapy symbolized by field lines 2) to the patient 3. Cooperation of treatment energy sources providing different treatment energies (e.g.: RF, ultrasound, light, acoustic wave, shock wave, plasma, mechanical massage, cooling/heating, electric field, electric current, magnetic field and/or other treatment energy sources) may be used for better targeting of the delivered therapy, better focusing of a delivered signal, the creation of some gradient in the soft tissue (e.g. thermal gradient, etc.), or better homogeneity of provided therapy across a large patient area and/or volume of the soft tissue.

According to one embodiment, the cooperation of multiple applicators and/or treatment energy sources may increase treatment variability (e.g. treatment depth, focusing, preventing hot spots) and may provide lower intensity of treatment energy without lowering treatment result, since the electrode of each applicator and/or treatment energy source represents one pole of a multipolar treatment.

Cooperation between applicators and/or treatment energy sources may include transferring of treatment energy or communication information and/or one applicator may provide a power supply to one or more other applicators.

The presented description of the device is not intended to limit the invention to these embodiments, but rather to enable any person skilled in the art to make and use this invention.

The invention claimed is:

1. A treatment device for improvement of a visual appearance of a patient, comprising:
   a mother case, comprising:
      a first treatment unit configured to generate a radio-frequency (RF) energy;
      a second treatment unit configured to generate an electric current;
      a user interface configured to provide one or more treatment protocols to be selected by a user of the device; and
      a control unit comprising a processor and a memory and configured to control the first treatment unit and the second treatment unit according to the selected one or more treatment protocols;
   a plurality of applicators removably connected to the mother case and configured to be attached to a body part of the patient, each applicator of the plurality of applicators comprising:
      a plurality of electrodes configured to apply the RF energy to the body part to cause a heating of an adipose tissue of the body part and to apply the electric current to the body part to cause muscle stimulation of a muscle within the body part;
      wherein each electrode of the plurality of electrodes has a surface area in a range of 1 cm$^2$ to 1200 cm$^2$; and
   a spacing object comprising a polymeric material configured to be positioned between the applicator and the body part and configured to provide better transfer of the RF energy and/or the electric current to the body part; and
   a belt configured to encircle the body part and to attach the plurality of applicators to the body part;
   wherein the body part comprises an abdomen, buttocks, thigh or arm.

2. The device of claim 1, further comprising an emergency stop button configured to stop delivering treatment energies to the body part of the patient.

3. The device of claim 1, wherein the control unit is configured to communicate with the first treatment unit and the second treatment based on a master-slave communication;
   wherein the control unit is a master unit;
   wherein the first treatment unit is a first slave unit;
   wherein the second treatment unit is a second slave unit; and
   wherein the communication is provided via an electrically conductive connection.

4. The device of claim 1, further including a billing system based on a credit subtracting, the credit predefined by a provider of the device.

5. The device of claim 1, wherein the user interface comprises a touch display, a button, a circle control element, or a switch button.

6. The device of claim 1, wherein each applicator of the plurality of applicators has an active surface in a range of 10 cm$^2$ to 500 cm$^2$.

7. The device of claim 1, wherein the control unit is configured to provide the RF energy and the electric current via the plurality of electrodes simultaneously.

8. The device of claim 1, wherein each applicator of the plurality of applicators has a symmetrical shape.

9. A treatment device for improvement of a visual appearance of a patient, comprising:
   a mother case, comprising:
      a first treatment unit configured to generate a first energy;
      a second treatment unit configured to generate a second energy different than the first energy;
      a user interface configured to provide one or more treatment protocols to be selected by a user of the device;
      a control unit comprising a processor and a memory and configured to control the first treatment unit and the second treatment unit according to the selected one or more treatment protocols; and
      a communication interface configured to transmit and receive information between the treatment device and an external device via a network connection;
   a plurality of applicators configured to be removably connected to the mother case and configured to be attached to a body part of the patient, each applicator of the plurality of applicators comprising:
      a plurality of electrodes configured to apply the first energy to the body part to cause a heating of a tissue of the body part and to apply the second energy to the body part to cause muscle stimulation of a muscle within the body part; and
      a plurality of temperature sensors configured to measure a temperature of the plurality of electrodes and configured to provide the measured temperature to the control unit;
   a plurality of electrically conductive cables configured to connect the plurality of applicators to the mother case and configured to provide a connection between the plurality of temperature sensors, the plurality of electrodes, and the control unit; and a belt configured to encircle the body part and to attach the plurality of applicators to the body part;

wherein the control unit is configured to recognize connected applicators from the plurality of applicators and provide the treatment via the connected applicators in order to improve the visual appearance of the patient.

10. The device of claim 9, wherein the communication interface comprises one of a Bluetooth, Wi-Fi, 3G, or 4G communication interface.

11. The device of claim 9, wherein the communication interface comprises a Global System for Mobile (GSM) interface.

12. The device of claim 11, wherein the external device is a server of a service department or a sales department of the treatment device.

13. The device of claim 12, wherein the information comprises one of: a number of applied treatments, time of applied treatments, a type of applied treatment, wear of the treatment device or its components, consumption of the device or its components, or errors in the treatment device.

14. The device of claim 13, wherein the communication interface is configured to communicate with the server bidirectionally and is configured to update a software of the treatment device based on data received from the service department or sales department.

15. The device of claim 9, wherein the first energy is a radio-frequency energy, wherein the second energy is an electric current, and wherein the control unit is configured to provide the radio-frequency energy and the electric current via the plurality of electrodes sequentially.

16. A treatment device for improvement of a visual appearance of a patient, comprising:

a mother case, comprising:

a first treatment unit configured to generate a radio-frequency (RF) energy;

a second treatment unit configured to generate an electric current;

a user interface configured to provide one or more treatment protocols to be selected by a user of the device; and a control unit comprising a processor and a memory and configured to control the first treatment unit and the second treatment unit according to the selected one or more treatment protocols;

an applicator configured to be removably connected to the mother case and configured to be attached to a body part of the patient, the applicator comprising:

an electrode configured to apply the RF energy to the body part to cause a heating of a skin of the body part and to apply the electric current to the body part to cause muscle stimulation of a muscle within the body part;

wherein the electrode has a diameter in a range of 0.6 cm to 40 cm;

a polymeric material configured to be positioned between the applicator and the body part and configured to improve transfer of the RF energy and/or the electric current to the body part; and a belt configured to encircle the body part and to attach the plurality of applicators to the body part;

wherein the body part comprises an abdomen, buttocks, thigh or arm; and wherein the control unit is configured to provide the treatment by the RF energy and the electric current in order to provide a skin tightening of the body part of the patient.

17. The device of claim 16, wherein the applicator has a symmetrical shape.

18. The device of claim 17, wherein the applicator has an active surface area in a range of 10 cm$^2$ to 100 cm$^2$.

19. The device of claim 16, further comprising a cable connection configured to connect the applicator with the mother case.

20. The device of claim 16, wherein the control unit is configured to provide the RF energy and the electric current sequentially.

* * * * *